US008722072B2

(12) United States Patent
Fischer et al.

(10) Patent No.: US 8,722,072 B2
(45) Date of Patent: May 13, 2014

(54) ACARICIDAL AND/OR INSECTICIDAL ACTIVE INGREDIENT COMBINATIONS

(75) Inventors: Reiner Fischer, Monheim (DE);
Veronica Companys, Langenfeld (DE);
Estuardo Jara Dominguez, Pulheim (DE); Heike Hungenberg, Langenfeld (DE); Peter Meisner, Niederkassel (DE)

(73) Assignee: Bayer Intellectual Property GmbH, Monheim (DE)

( * ) Notice: Subject to any disclaimer, the term of this patent is extended or adjusted under 35 U.S.C. 154(b) by 35 days.

(21) Appl. No.: 13/010,590

(22) Filed: Jan. 20, 2011

(65) Prior Publication Data

US 2011/0229582 A1  Sep. 22, 2011

Related U.S. Application Data

(60) Provisional application No. 61/297,395, filed on Jan. 22, 2010.

(30) Foreign Application Priority Data

Jan. 22, 2010  (EP) .................................... 10151415

(51) Int. Cl.
| | | |
|---|---|---|
| *A01N 25/08* | (2006.01) | |
| *A01N 25/00* | (2006.01) | |
| *A01N 43/12* | (2006.01) | |
| *A01N 43/26* | (2006.01) | |
| *A01N 43/04* | (2006.01) | |
| *A01N 63/00* | (2006.01) | |

(52) U.S. Cl.
CPC .............. *A01N 25/08* (2013.01); *A01N 25/006* (2013.01); *A01N 43/12* (2013.01); *A01N 43/26* (2013.01); *A01N 43/04* (2013.01); *A01N 63/00* (2013.01)
USPC ............. 424/409; 424/405; 424/406; 514/30; 514/462; 119/6.6; 119/6.7

(58) Field of Classification Search
CPC ..... A01N 25/08; A01N 25/006; A01N 43/12; A01N 43/26; A01N 43/04; A01N 63/00
See application file for complete search history.

(56) References Cited

U.S. PATENT DOCUMENTS

| | | |
|---|---|---|
| 3,272,854 A | 9/1966 | Covey et al. |
| 3,835,176 A | 9/1974 | Matsuo et al. |
| 4,310,519 A | 1/1982 | Albers-Schonberg et al. |
| 4,761,373 A | 8/1988 | Anderson et al. |
| 5,013,659 A | 5/1991 | Bedbrook et al. |
| 5,084,082 A | 1/1992 | Sebastian |
| 5,141,870 A | 8/1992 | Bedbrook et al. |
| 5,198,599 A | 3/1993 | Thill |
| 5,262,383 A | 11/1993 | Fischer et al. |
| 5,273,894 A | 12/1993 | Strauch et al. |
| 5,276,268 A | 1/1994 | Strauch et al. |
| 5,304,732 A | 4/1994 | Anderson et al. |
| 5,331,107 A | 7/1994 | Anderson et al. |
| 5,378,824 A | 1/1995 | Bedbrook et al. |
| 5,434,283 A | 7/1995 | Wong et al. |
| 5,463,175 A | 10/1995 | Barry et al. |
| 5,561,236 A | 10/1996 | Leemans et al. |
| 5,605,011 A | 2/1997 | Bedbrook et al. |
| 5,637,489 A | 6/1997 | Strauch et al. |
| 5,646,024 A | 7/1997 | Leemans et al. |
| 5,648,477 A | 7/1997 | Leemans et al. |
| 5,712,107 A | 1/1998 | Nichols |
| 5,731,180 A | 3/1998 | Dietrich |
| 5,739,082 A | 4/1998 | Donn |
| 5,767,361 A | 6/1998 | Dietrich |
| 5,773,702 A | 6/1998 | Penner et al. |
| 5,776,760 A | 7/1998 | Barry et al. |
| 5,824,790 A | 10/1998 | Keeling et al. |
| 5,840,946 A | 11/1998 | Wong et al. |
| 5,866,782 A | 2/1999 | Iwabuchi et al. |
| 5,908,810 A | 6/1999 | Donn |
| 5,908,975 A | 6/1999 | Caimi et al. |
| 5,928,937 A | 7/1999 | Kakefuda et al. |
| 5,965,755 A | 10/1999 | Sernyk et al. |
| 5,969,169 A | 10/1999 | Fan |
| 6,013,861 A | 1/2000 | Bird et al. |
| 6,040,497 A | 3/2000 | Spencer et al. |

(Continued)

FOREIGN PATENT DOCUMENTS

| | | |
|---|---|---|
| AU | B-86631/91 | 9/1994 |
| CA | 2 561 992 A1 | 3/2007 |

(Continued)

OTHER PUBLICATIONS

Elbert et al Pflanzenschutz-Nachrichten—58(3), pp. 441-468—2005—Abstract.*
Buschman et al arthropod management tests 30, F12-2005AB-STRACT—2006:1204685 HCAPLUS # 146:268341.*
Barry, G., et al., "Inhibitors of Amino Acid Biosynthesis: Strategies for Imparting Glyphosate Tolerance to Crop Plants," *Current Topics in Plant Physiology* 7:139-145, American Society of Plant Physiologists, USA (1992).

(Continued)

*Primary Examiner* — Neil Levy
(74) *Attorney, Agent, or Firm* — Sterne, Kessler, Goldstein & Fox P.L.L.C.

(57) ABSTRACT

The present invention relates to active ingredient combinations which are composed of a known dihydrofuranone derivative on the one hand and of other known active pesticidal ingredients on the other hand, and are suitable for controlling animal pests from the families of the Aleyrodidae, Thripidae, Psyllidae and Agromyzidae, and also, more particularly, from the order of the Acari. The invention also relates to combinations which consist of the abovementioned active ingredient combinations on the one hand and of beneficial species on the other hand and which are suitable for controlling animal pests.

20 Claims, No Drawings

(56) References Cited

U.S. PATENT DOCUMENTS

| | | |
|---|---|---|
| 6,063,947 A | 5/2000 | DeBonte et al. |
| 6,130,367 A | 10/2000 | Kossmann et al. |
| 6,162,966 A | 12/2000 | Kossmann et al. |
| 6,169,190 B1 | 1/2001 | Lanuza et al. |
| 6,207,880 B1 | 3/2001 | Kossmann et al. |
| 6,211,436 B1 | 4/2001 | Kossmann et al. |
| 6,229,072 B1 | 5/2001 | Burns et al. |
| 6,245,968 B1 | 6/2001 | Boudec et al. |
| 6,255,561 B1 | 7/2001 | Kossmann et al. |
| 6,255,563 B1 | 7/2001 | Emmermann et al. |
| 6,268,549 B1 | 7/2001 | Sailland et al. |
| 6,270,828 B1 | 8/2001 | DeBonte et al. |
| 6,284,479 B1 | 9/2001 | Nichols |
| 6,294,712 B1 | 9/2001 | Kleine et al. |
| 6,307,124 B1 | 10/2001 | Kossmann et al. |
| 6,323,392 B1 | 11/2001 | Charne |
| 6,436,988 B1 | 8/2002 | Wachendorff-Neumann |
| 6,465,203 B2 | 10/2002 | Nichols |
| 6,566,585 B1 | 5/2003 | Quanz |
| 6,566,587 B1 | 5/2003 | Lebrun et al. |
| 6,590,141 B1 | 7/2003 | Frohberg |
| 6,596,928 B1 | 7/2003 | Landschütze |
| 6,653,343 B2 | 11/2003 | Fischer et al. |
| 6,699,694 B1 | 3/2004 | Buttcher et al. |
| 6,706,758 B2 | 3/2004 | Fischer et al. |
| 6,716,874 B1 | 4/2004 | Bretschneider et al. |
| 6,734,341 B2 | 5/2004 | Singletary et al. |
| 6,791,010 B1 | 9/2004 | Frohberg |
| 6,794,558 B1 | 9/2004 | Frohberg |
| 6,812,010 B1 | 11/2004 | Derose et al. |
| 6,890,732 B1 | 5/2005 | Loerz et al. |
| 6,891,088 B1 | 5/2005 | Neuhaus et al. |
| 6,897,358 B2 | 5/2005 | Loerz et al. |
| 6,919,090 B2 | 7/2005 | Fischer et al. |
| 6,940,001 B1 | 9/2005 | Landschütze |
| 7,112,665 B1 | 9/2006 | Leemans et al. |
| 7,157,281 B2 | 1/2007 | Dizigan et al. |
| 7,304,209 B2 | 12/2007 | Zink et al. |
| 7,335,816 B2 | 2/2008 | Kraus et al. |
| 7,435,807 B1 | 10/2008 | Barbour et al. |
| 7,576,264 B2 | 8/2009 | Dogimont et al. |
| 2003/0083371 A1 | 5/2003 | Fischer et al. |
| 2003/0100604 A1 | 5/2003 | Fischer et al. |
| 2003/0114312 A1 | 6/2003 | Fischer et al. |
| 2003/0126634 A1 | 7/2003 | Spencer et al. |
| 2003/0185813 A1 | 10/2003 | Fischer et al. |
| 2003/0211944 A1 | 11/2003 | Fischer et al. |
| 2004/0117870 A1 | 6/2004 | Weyens et al. |
| 2004/0148666 A1 | 7/2004 | Rangwala et al. |
| 2004/0177399 A1 | 9/2004 | Hammer et al. |
| 2004/0180373 A1 | 9/2004 | Levine |
| 2004/0180873 A1 | 9/2004 | Hanssen et al. |
| 2004/0197916 A1 | 10/2004 | Carozzi et al. |
| 2004/0210964 A1 | 10/2004 | Carozzi et al. |
| 2004/0216186 A1 | 10/2004 | Carozzi et al. |
| 2004/0250317 A1 | 12/2004 | Huber et al. |
| 2005/0257283 A1 | 11/2005 | Matringe et al. |
| 2006/0021093 A1 | 1/2006 | Hammer et al. |
| 2006/0070139 A1 | 3/2006 | Bing et al. |
| 2006/0095986 A1 | 5/2006 | Cavato et al. |
| 2006/0130175 A1 | 6/2006 | Ellis et al. |
| 2006/0150269 A1 | 7/2006 | Hammer et al. |
| 2006/0150270 A1 | 7/2006 | Hammer et al. |
| 2006/0162007 A1 | 7/2006 | Guo et al. |
| 2006/0168690 A1 | 7/2006 | Shibatani et al. |
| 2006/0230473 A1 | 10/2006 | Johnson et al. |
| 2006/0242732 A1 | 10/2006 | Carozzi et al. |
| 2006/0253921 A1 | 11/2006 | Carozzi et al. |
| 2006/0282915 A1 | 12/2006 | Malven et al. |
| 2007/0004907 A1 | 1/2007 | Hammer et al. |
| 2007/0022496 A1 | 1/2007 | Moor et al. |
| 2007/0056056 A1 | 3/2007 | Behr et al. |
| 2007/0067868 A1 | 3/2007 | Negrotto et al. |
| 2007/0107078 A1 | 5/2007 | Hammer et al. |
| 2007/0136840 A1 | 6/2007 | Peters et al. |
| 2007/0169218 A1 | 7/2007 | Carr et al. |
| 2007/0240239 A1 | 10/2007 | Carozzi et al. |
| 2007/0254949 A1 | 11/2007 | Bretschneider et al. |
| 2007/0289035 A1 | 12/2007 | Vande Berg et al. |
| 2007/0292854 A1 | 12/2007 | Behr et al. |
| 2008/0064032 A1 | 3/2008 | Townshend et al. |
| 2008/0176801 A1 | 7/2008 | Carozzi et al. |
| 2008/0250533 A1 | 10/2008 | Frohberg |
| 2008/0289060 A1 | 11/2008 | De Beuckeleer et al. |
| 2008/0312419 A1 | 12/2008 | Hammer et al. |
| 2009/0044291 A1 | 2/2009 | Zhang et al. |
| 2009/0100543 A1 | 4/2009 | Carozzi et al. |
| 2009/0119797 A1 | 5/2009 | Hammer et al. |
| 2009/0126044 A1 | 5/2009 | Carozzi et al. |
| 2009/0151018 A1 | 6/2009 | Hammer et al. |
| 2009/0156669 A1 | 6/2009 | Fischer et al. |
| 2009/0181399 A1 | 7/2009 | Negrotto et al. |
| 2009/0193545 A1 | 7/2009 | Watson |
| 2009/0203075 A1 | 8/2009 | Hammer et al. |
| 2009/0227771 A1 | 9/2009 | Peters et al. |
| 2009/0253784 A1 | 10/2009 | Fischer et al. |
| 2009/0313717 A1 | 12/2009 | Hernandez et al. |
| 2010/0083404 A1 | 4/2010 | Ogawa et al. |
| 2010/0113273 A1 | 5/2010 | Takabe et al. |
| 2010/0130366 A1 | 5/2010 | Andersch et al. |
| 2010/0168042 A1 | 7/2010 | Funke et al. |
| 2010/0173987 A1 | 7/2010 | Fischer et al. |
| 2010/0199764 A1 | 8/2010 | Hammer |
| 2010/0216738 A1 | 8/2010 | Fischer et al. |
| 2011/0023189 A1 | 1/2011 | Takahashi et al. |
| 2011/0119790 A1 | 5/2011 | Fujino et al. |

FOREIGN PATENT DOCUMENTS

| | | |
|---|---|---|
| CA | 2 718 396 A1 | 9/2009 |
| CA | 2 737 735 A1 | 4/2010 |
| CN | 1840655 A | 10/2006 |
| DE | 103 42 673 A1 | 4/2005 |
| EP | 0 089 202 | 9/1983 |
| EP | 0 134 439 A1 | 3/1985 |
| EP | 0 234 045 A2 | 9/1987 |
| EP | 0 326 329 A2 | 8/1989 |
| EP | 2 216 408 A1 | 8/2010 |
| JP | 2006-304779 | 11/2006 |
| WO | WO 89/10396 A1 | 11/1989 |
| WO | WO 91/02069 A1 | 2/1991 |
| WO | WO 92/14827 A1 | 9/1992 |
| WO | WO 93/10083 A1 | 5/1993 |
| WO | WO 93/18170 A1 | 9/1993 |
| WO | WO 94/04692 A1 | 3/1994 |
| WO | WO 94/04693 A2 | 3/1994 |
| WO | WO 94/09144 A1 | 4/1994 |
| WO | WO 94/11520 A2 | 5/1994 |
| WO | WO 94/21795 A1 | 9/1994 |
| WO | WO 94/23043 A2 | 10/1994 |
| WO | WO 95/04826 A1 | 2/1995 |
| WO | WO 95/07355 A1 | 3/1995 |
| WO | WO 95/09911 A1 | 4/1995 |
| WO | WO 95/13389 A1 | 5/1995 |
| WO | WO 95/20669 A2 | 8/1995 |
| WO | WO 95/26407 A1 | 10/1995 |
| WO | WO 95/31553 A1 | 11/1995 |
| WO | WO 95/35026 A1 | 12/1995 |
| WO | WO 96/01904 A1 | 1/1996 |
| WO | WO 96/19581 A1 | 6/1996 |
| WO | WO 96/21023 A1 | 7/1996 |
| WO | WO 96/30517 A1 | 10/1996 |
| WO | WO 96/30529 A1 | 10/1996 |
| WO | WO 96/33270 A1 | 10/1996 |
| WO | WO 96/34968 A2 | 11/1996 |
| WO | WO 97/13865 A1 | 4/1997 |
| WO | WO 97/20936 A1 | 6/1997 |
| WO | WO 97/30163 A1 | 8/1997 |
| WO | WO 97/41218 A1 | 11/1997 |
| WO | WO 97/45545 A1 | 12/1997 |
| WO | WO 97/46080 A1 | 12/1997 |
| WO | WO 97/47806 A1 | 12/1997 |
| WO | WO 97/47807 A1 | 12/1997 |
| WO | WO 97/47808 A1 | 12/1997 |

(56) References Cited

FOREIGN PATENT DOCUMENTS

| | | |
|---|---|---|
| WO | WO 98/00549 A1 | 1/1998 |
| WO | WO 98/20145 A2 | 5/1998 |
| WO | WO 98/22604 A1 | 5/1998 |
| WO | WO 98/27212 A1 | 6/1998 |
| WO | WO 98/27806 A1 | 7/1998 |
| WO | WO 98/32326 A2 | 7/1998 |
| WO | WO 98/39460 A1 | 9/1998 |
| WO | WO 98/40503 A1 | 9/1998 |
| WO | WO 99/00502 A1 | 1/1999 |
| WO | WO 99/12950 A2 | 3/1999 |
| WO | WO 99/15680 A1 | 4/1999 |
| WO | WO 99/24593 A1 | 5/1999 |
| WO | WO 99/53072 A1 | 10/1999 |
| WO | WO 99/57965 A1 | 11/1999 |
| WO | WO 99/60141 A1 | 11/1999 |
| WO | WO 99/66050 A1 | 12/1999 |
| WO | WO 00/04173 A1 | 1/2000 |
| WO | WO 00/11192 A2 | 3/2000 |
| WO | WO 00/14249 A1 | 3/2000 |
| WO | WO 00/28052 A2 | 5/2000 |
| WO | WO 00/47727 A2 | 8/2000 |
| WO | WO 00/63432 A1 | 10/2000 |
| WO | WO 00/66746 A1 | 11/2000 |
| WO | WO 00/66747 A1 | 11/2000 |
| WO | WO 00/73422 A1 | 12/2000 |
| WO | WO 00/73475 A1 | 12/2000 |
| WO | WO 00/77229 A2 | 12/2000 |
| WO | WO 01/14569 A2 | 3/2001 |
| WO | WO 01/17333 A1 | 3/2001 |
| WO | WO 01/19975 A2 | 3/2001 |
| WO | WO 01/24615 A1 | 4/2001 |
| WO | WO 01/31042 A2 | 5/2001 |
| WO | WO 01/41558 A1 | 6/2001 |
| WO | WO 01/51627 A2 | 7/2001 |
| WO | WO 01/51654 A2 | 7/2001 |
| WO | WO 01/60158 A1 | 8/2001 |
| WO | WO 01/65922 A2 | 9/2001 |
| WO | WO 01/66704 A2 | 9/2001 |
| WO | WO 01/70027 A2 | 9/2001 |
| WO | WO 01/78511 A1 | 10/2001 |
| WO | WO 01/83818 A2 | 11/2001 |
| WO | WO 01/98509 A2 | 12/2001 |
| WO | WO 02/02776 A1 | 1/2002 |
| WO | WO 02/22836 A2 | 3/2002 |
| WO | WO 02/26995 A1 | 4/2002 |
| WO | WO 02/34923 A2 | 5/2002 |
| WO | WO 02/36782 A2 | 5/2002 |
| WO | WO 02/36831 A2 | 5/2002 |
| WO | WO 02/45485 A1 | 6/2002 |
| WO | WO 02/061043 A2 | 8/2002 |
| WO | WO 02/079410 A2 | 10/2002 |
| WO | WO 02/081713 A1 | 10/2002 |
| WO | WO 02/085105 A2 | 10/2002 |
| WO | WO 02/099385 A2 | 12/2002 |
| WO | WO 02/101059 A2 | 12/2002 |
| WO | WO 03/013224 A2 | 2/2003 |
| WO | WO 03/013226 A2 | 2/2003 |
| WO | WO 03/033540 A2 | 4/2003 |
| WO | WO 03/033651 A2 | 4/2003 |
| WO | WO 03/052073 A2 | 6/2003 |
| WO | WO 03/071860 A2 | 9/2003 |
| WO | WO 03/092360 A2 | 11/2003 |
| WO | WO 2004/040012 A2 | 5/2004 |
| WO | WO 2004/049786 A1 | 6/2004 |
| WO | WO 2004/053219 A2 | 6/2004 |
| WO | WO 2004/056999 A1 | 7/2004 |
| WO | WO 2004/072235 A2 | 8/2004 |
| WO | WO 2004/078983 A2 | 9/2004 |
| WO | WO 2004/090140 A2 | 10/2004 |
| WO | WO 2004/101751 A2 | 11/2004 |
| WO | WO 2004/106529 A2 | 12/2004 |
| WO | WO 2004/111245 A2 | 12/2004 |
| WO | WO 2004/113542 A1 | 12/2004 |
| WO | WO 2005/000007 A2 | 1/2005 |
| WO | WO 2005/002324 A2 | 1/2005 |
| WO | WO 2005/002359 A2 | 1/2005 |
| WO | WO 2005/012515 A2 | 2/2005 |
| WO | WO 2005/017157 A1 | 2/2005 |
| WO | WO 2005/020673 A1 | 3/2005 |
| WO | WO 2005/021585 A2 | 3/2005 |
| WO | WO 2005/030941 A1 | 4/2005 |
| WO | WO 2005/030942 A1 | 4/2005 |
| WO | WO 2005/033318 A2 | 4/2005 |
| WO | WO 2005/038032 A1 | 4/2005 |
| WO | WO 2005/059103 A2 | 6/2005 |
| WO | WO 2005/065453 A1 | 7/2005 |
| WO | WO 2005/090578 A1 | 9/2005 |
| WO | WO 2005/093093 A2 | 10/2005 |
| WO | WO 2005/095617 A2 | 10/2005 |
| WO | WO 2005/095618 A2 | 10/2005 |
| WO | WO 2005/095619 A2 | 10/2005 |
| WO | WO 2005/095632 A2 | 10/2005 |
| WO | WO 2005/103266 A1 | 11/2005 |
| WO | WO 2005/103270 A2 | 11/2005 |
| WO | WO 2005/103301 A2 | 11/2005 |
| WO | WO 2005/123927 A1 | 12/2005 |
| WO | WO 2006/007373 A2 | 1/2006 |
| WO | WO 2006/009649 A2 | 1/2006 |
| WO | WO 2006/015376 A2 | 2/2006 |
| WO | WO 2006/018319 A1 | 2/2006 |
| WO | WO 2006/021972 A1 | 3/2006 |
| WO | WO 2006/024351 A1 | 3/2006 |
| WO | WO 2006/032469 A2 | 3/2006 |
| WO | WO 2006/032538 A1 | 3/2006 |
| WO | WO 2006/038794 A2 | 4/2006 |
| WO | WO 2006/045633 A1 | 5/2006 |
| WO | WO 2006/046861 A2 | 5/2006 |
| WO | WO 2006/055851 A2 | 5/2006 |
| WO | WO 2006/060634 A2 | 6/2006 |
| WO | WO 2006/063862 A1 | 6/2006 |
| WO | WO 2006/072603 A2 | 7/2006 |
| WO | WO 2006/085966 A2 | 8/2006 |
| WO | WO 2006/103107 A1 | 10/2006 |
| WO | WO 2006/108674 A2 | 10/2006 |
| WO | WO 2006/108675 A2 | 10/2006 |
| WO | WO 2006/108702 A1 | 10/2006 |
| WO | WO 2006/119457 A1 | 11/2006 |
| WO | WO 2006/125065 A2 | 11/2006 |
| WO | WO 2006/128568 A2 | 12/2006 |
| WO | WO 2006/128569 A2 | 12/2006 |
| WO | WO 2006/128570 A1 | 12/2006 |
| WO | WO 2006/128571 A2 | 12/2006 |
| WO | WO 2006/128572 A1 | 12/2006 |
| WO | WO 2006/128573 A2 | 12/2006 |
| WO | WO 2006/129204 A2 | 12/2006 |
| WO | WO 2006/130436 A2 | 12/2006 |
| WO | WO 2006/133827 A2 | 12/2006 |
| WO | WO 2006/135717 A1 | 12/2006 |
| WO | WO 2006/136351 A2 | 12/2006 |
| WO | WO 2007/009823 A1 | 1/2007 |
| WO | WO 2007/017186 A1 | 2/2007 |
| WO | WO 2007/024782 A2 | 3/2007 |
| WO | WO 2007/027777 A2 | 3/2007 |
| WO | WO 2007/035650 A2 | 3/2007 |
| WO | WO 2007/039314 A2 | 4/2007 |
| WO | WO 2007/039316 A1 | 4/2007 |
| WO | WO 2007/053015 A2 | 5/2007 |
| WO | WO 2007/073167 A1 | 6/2007 |
| WO | WO 2007/074405 A2 | 7/2007 |
| WO | WO 2007/076115 A2 | 7/2007 |
| WO | WO 2007/080126 A2 | 7/2007 |
| WO | WO 2007/080127 A2 | 7/2007 |
| WO | WO 2007/091277 A2 | 8/2007 |
| WO | WO 2007/092704 A2 | 8/2007 |
| WO | WO 2007/103567 A2 | 9/2007 |
| WO | WO 2007/103768 A2 | 9/2007 |
| WO | WO 2007/107302 A2 | 9/2007 |
| WO | WO 2007/107326 A1 | 9/2007 |
| WO | WO 2007/131699 A2 | 11/2007 |
| WO | WO 2007/140256 A1 | 12/2007 |
| WO | WO 2007/142840 A2 | 12/2007 |
| WO | WO 2007/146767 A2 | 12/2007 |
| WO | WO 2007/146980 A2 | 12/2007 |
| WO | WO 2007/147029 A2 | 12/2007 |

(56) References Cited

FOREIGN PATENT DOCUMENTS

| | | |
|---|---|---|
| WO | WO 2007/147096 A2 | 12/2007 |
| WO | WO 2008/002480 A2 | 1/2008 |
| WO | WO 2008/002872 A2 | 1/2008 |
| WO | WO 2008/002962 A2 | 1/2008 |
| WO | WO 2008/002964 A2 | 1/2008 |
| WO | WO 2008/005210 A2 | 1/2008 |
| WO | WO 2008/006033 A1 | 1/2008 |
| WO | WO 2008/008779 A2 | 1/2008 |
| WO | WO 2008/015263 A2 | 2/2008 |
| WO | WO 2008/017518 A1 | 2/2008 |
| WO | WO 2008/021021 A2 | 2/2008 |
| WO | WO 2008/022486 A1 | 2/2008 |
| WO | WO 2008/025097 A1 | 3/2008 |
| WO | WO 2008/027534 A2 | 3/2008 |
| WO | WO 2008/037902 A1 | 4/2008 |
| WO | WO 2008/043849 A2 | 4/2008 |
| WO | WO 2008/044150 A2 | 4/2008 |
| WO | WO 2008/046069 A2 | 4/2008 |
| WO | WO 2008/049183 A1 | 5/2008 |
| WO | WO 2008/051608 A2 | 5/2008 |
| WO | WO 2008/053487 A2 | 5/2008 |
| WO | WO 2008/054747 A2 | 5/2008 |
| WO | WO 2008/056915 A1 | 5/2008 |
| WO | WO 2008/057642 A1 | 5/2008 |
| WO | WO 2008/059048 A1 | 5/2008 |
| WO | WO 2008/061240 A2 | 5/2008 |
| WO | WO 2008/062049 A1 | 5/2008 |
| WO | WO 2008/064222 A2 | 5/2008 |
| WO | WO 2008/064341 A1 | 5/2008 |
| WO | WO 2008/067043 A2 | 6/2008 |
| WO | WO 2008/071767 A1 | 6/2008 |
| WO | WO 2008/073617 A2 | 6/2008 |
| WO | WO 2008/074025 A2 | 6/2008 |
| WO | WO 2008/074891 A2 | 6/2008 |
| WO | WO 2008/076844 A2 | 6/2008 |
| WO | WO 2008/080630 A1 | 7/2008 |
| WO | WO 2008/080631 A1 | 7/2008 |
| WO | WO 2008/090008 A1 | 7/2008 |
| WO | WO 2008/092910 A1 | 8/2008 |
| WO | WO 2008/092935 A2 | 8/2008 |
| WO | WO 2008/095886 A1 | 8/2008 |
| WO | WO 2008/095887 A1 | 8/2008 |
| WO | WO 2008/095888 A1 | 8/2008 |
| WO | WO 2008/095889 A1 | 8/2008 |
| WO | WO 2008/095910 A1 | 8/2008 |
| WO | WO 2008/095911 A2 | 8/2008 |
| WO | WO 2008/095916 A1 | 8/2008 |
| WO | WO 2008/095919 A1 | 8/2008 |
| WO | WO 2008/095969 A1 | 8/2008 |
| WO | WO 2008/095970 A1 | 8/2008 |
| WO | WO 2008/095972 A1 | 8/2008 |
| WO | WO 2008/096138 A1 | 8/2008 |
| WO | WO 2008/100353 A2 | 8/2008 |
| WO | WO 2008/104598 A2 | 9/2008 |
| WO | WO 2008/110522 A1 | 9/2008 |
| WO | WO 2008/110848 A2 | 9/2008 |
| WO | WO 2008/111779 A1 | 9/2008 |
| WO | WO 2008/112019 A2 | 9/2008 |
| WO | WO 2008/112613 A2 | 9/2008 |
| WO | WO 2008/114282 A2 | 9/2008 |
| WO | WO 2008/116829 A1 | 10/2008 |
| WO | WO 2008/118394 A1 | 10/2008 |
| WO | WO 2008/121320 A2 | 10/2008 |
| WO | WO 2008/122406 A1 | 10/2008 |
| WO | WO 2008/122980 A2 | 10/2008 |
| WO | WO 2008/125983 A2 | 10/2008 |
| WO | WO 2008/135206 A2 | 11/2008 |
| WO | WO 2008/135467 A2 | 11/2008 |
| WO | WO 2008/135603 A2 | 11/2008 |
| WO | WO 2008/137108 A2 | 11/2008 |
| WO | WO 2008/138975 A1 | 11/2008 |
| WO | WO 2008/139334 A2 | 11/2008 |
| WO | WO 2008/142034 A2 | 11/2008 |
| WO | WO 2008/142036 A2 | 11/2008 |
| WO | WO 2008/142146 A1 | 11/2008 |
| WO | WO 2008/142163 A2 | 11/2008 |
| WO | WO 2008/145629 A2 | 12/2008 |
| WO | WO 2008/145675 A2 | 12/2008 |
| WO | WO 2008/145761 A1 | 12/2008 |
| WO | WO 2008/148872 A1 | 12/2008 |
| WO | WO 2008/150165 A1 | 12/2008 |
| WO | WO 2008/150473 A2 | 12/2008 |
| WO | WO 2008/151780 A1 | 12/2008 |
| WO | WO 2008/152008 A2 | 12/2008 |
| WO | WO 2009/000736 A2 | 12/2008 |
| WO | WO 2009/000789 A1 | 12/2008 |
| WO | WO 2009/000848 A1 | 12/2008 |
| WO | WO 2009/000876 A1 | 12/2008 |
| WO | WO 2009/003649 A2 | 1/2009 |
| WO | WO 2009/003977 A2 | 1/2009 |
| WO | WO 2009/007091 A2 | 1/2009 |
| WO | WO 2009/009142 A2 | 1/2009 |
| WO | WO 2009/010460 A2 | 1/2009 |
| WO | WO 2009/012467 A2 | 1/2009 |
| WO | WO 2009/013225 A2 | 1/2009 |
| WO | WO 2009/013263 A2 | 1/2009 |
| WO | WO 2009/014665 A2 | 1/2009 |
| WO | WO 2009/015096 A2 | 1/2009 |
| WO | WO 2009/016104 A1 | 2/2009 |
| WO | WO 2009/016212 A2 | 2/2009 |
| WO | WO 2009/016232 A2 | 2/2009 |
| WO | WO 2009/021153 A2 | 2/2009 |
| WO | WO 2009/021548 A1 | 2/2009 |
| WO | WO 2009/034188 A1 | 3/2009 |
| WO | WO 2009/036234 A1 | 3/2009 |
| WO | WO 2009/037279 A1 | 3/2009 |
| WO | WO 2009/037329 A2 | 3/2009 |
| WO | WO 2009/037338 A1 | 3/2009 |
| WO | WO 2009/038581 A2 | 3/2009 |
| WO | WO 2009/040665 A2 | 4/2009 |
| WO | WO 2009/049110 A1 | 4/2009 |
| WO | WO 2009/052242 A2 | 4/2009 |
| WO | WO 2009/054735 A2 | 4/2009 |
| WO | WO 2009/056566 A2 | 5/2009 |
| WO | WO 2009/060040 A1 | 5/2009 |
| WO | WO 2009/061776 A1 | 5/2009 |
| WO | WO 2009/064652 A1 | 5/2009 |
| WO | WO 2009/065863 A1 | 5/2009 |
| WO | WO 2009/065912 A2 | 5/2009 |
| WO | WO 2009/067580 A2 | 5/2009 |
| WO | WO 2009/068313 A2 | 6/2009 |
| WO | WO 2009/068564 A1 | 6/2009 |
| WO | WO 2009/068588 A2 | 6/2009 |
| WO | WO 2009/073069 A2 | 6/2009 |
| WO | WO 2009/073605 A2 | 6/2009 |
| WO | WO 2009/075860 A2 | 6/2009 |
| WO | WO 2009/077611 A2 | 6/2009 |
| WO | WO 2009/077973 A1 | 6/2009 |
| WO | WO 2009/079508 A1 | 6/2009 |
| WO | WO 2009/079529 A2 | 6/2009 |
| WO | WO 2009/080743 A2 | 7/2009 |
| WO | WO 2009/080802 A2 | 7/2009 |
| WO | WO 2009/083958 A2 | 7/2009 |
| WO | WO 2009/086229 A2 | 7/2009 |
| WO | WO 2009/086850 A1 | 7/2009 |
| WO | WO 2009/091518 A2 | 7/2009 |
| WO | WO 2009/091860 A2 | 7/2009 |
| WO | WO 2009/092009 A2 | 7/2009 |
| WO | WO 2009/092560 A1 | 7/2009 |
| WO | WO 2009/092772 A2 | 7/2009 |
| WO | WO 2009/094401 A2 | 7/2009 |
| WO | WO 2009/094527 A1 | 7/2009 |
| WO | WO 2009/095455 A1 | 8/2009 |
| WO | WO 2009/095641 A2 | 8/2009 |
| WO | WO 2009/095881 A2 | 8/2009 |
| WO | WO 2009/097133 A2 | 8/2009 |
| WO | WO 2009/099906 A2 | 8/2009 |
| WO | WO 2009/102873 A1 | 8/2009 |
| WO | WO 2009/102965 A2 | 8/2009 |
| WO | WO 2009/102978 A2 | 8/2009 |
| WO | WO 2009/105492 A2 | 8/2009 |
| WO | WO 2009/105612 A2 | 8/2009 |
| WO | WO 2009/106596 A2 | 9/2009 |
| WO | WO 2009/108513 A2 | 9/2009 |

(56) References Cited

FOREIGN PATENT DOCUMENTS

| | | |
|---|---|---|
| WO | WO 2009/111263 A1 | 9/2009 |
| WO | WO 2009/111627 A1 | 9/2009 |
| WO | WO 2009/112505 A2 | 9/2009 |
| WO | WO 2009/114733 A2 | 9/2009 |
| WO | WO 2009/117448 A1 | 9/2009 |
| WO | WO 2009/117853 A1 | 10/2009 |
| WO | WO 2009/126359 A1 | 10/2009 |
| WO | WO 2009/126462 A2 | 10/2009 |
| WO | WO 2009/127671 A1 | 10/2009 |
| WO | WO 2009/129162 A2 | 10/2009 |
| WO | WO 2009/132057 A1 | 10/2009 |
| WO | WO 2009/132089 A2 | 10/2009 |
| WO | WO 2009/132779 A1 | 11/2009 |
| WO | WO 2009/132850 A1 | 11/2009 |
| WO | WO 2009/134339 A2 | 11/2009 |
| WO | WO 2009/135130 A2 | 11/2009 |
| WO | WO 2009/135810 A8 | 11/2009 |
| WO | WO 2009/141824 A2 | 11/2009 |
| WO | WO 2009/143995 A1 | 12/2009 |
| WO | WO 2009/145290 A1 | 12/2009 |
| WO | WO 2009/148330 A1 | 12/2009 |
| WO | WO 2009/149787 A1 | 12/2009 |
| WO | WO 2009/150170 A1 | 12/2009 |
| WO | WO 2009/150541 A2 | 12/2009 |
| WO | WO 2009/153208 A1 | 12/2009 |
| WO | WO 2009/156360 A1 | 12/2009 |
| WO | WO 2009/158470 A2 | 12/2009 |
| WO | WO 2010/000794 A1 | 1/2010 |
| WO | WO 2010/003065 A2 | 1/2010 |
| WO | WO 2010/003917 A1 | 1/2010 |
| WO | WO 2010/005298 A2 | 1/2010 |
| WO | WO 2010/006010 A1 | 1/2010 |
| WO | WO 2010/006732 A2 | 1/2010 |
| WO | WO 2010/007035 A1 | 1/2010 |
| WO | WO 2010/007495 A2 | 1/2010 |
| WO | WO 2010/007496 A2 | 1/2010 |
| WO | WO 2010/012760 A2 | 2/2010 |
| WO | WO 2010/012796 A1 | 2/2010 |
| WO | WO 2010/019838 A2 | 2/2010 |
| WO | WO 2010/019872 A1 | 2/2010 |
| WO | WO 2010/023186 A1 | 3/2010 |
| WO | WO 2010/023310 A2 | 3/2010 |
| WO | WO 2010/023320 A2 | 3/2010 |
| WO | WO 2010/024976 A1 | 3/2010 |
| WO | WO 2010/025172 A8 | 3/2010 |
| WO | WO 2010/025465 A1 | 3/2010 |
| WO | WO 2010/025466 A2 | 3/2010 |
| WO | WO 2010/025513 A1 | 3/2010 |
| WO | WO 2010/027793 A1 | 3/2010 |
| WO | WO 2010/027799 A1 | 3/2010 |
| WO | WO 2010/027804 A2 | 3/2010 |
| WO | WO 2010/027805 A2 | 3/2010 |
| WO | WO 2010/027808 A2 | 3/2010 |
| WO | WO 2010/027809 A1 | 3/2010 |
| WO | WO 2010/028205 A1 | 3/2010 |
| WO | WO 2010/028456 A1 | 3/2010 |
| WO | WO 2010/031312 A1 | 3/2010 |
| WO | WO 2010/033564 A1 | 3/2010 |
| WO | WO 2010/034652 A1 | 4/2010 |
| WO | WO 2010/034672 A1 | 4/2010 |
| WO | WO 2010/034681 A1 | 4/2010 |
| WO | WO 2010/036764 A1 | 4/2010 |
| WO | WO 2010/036866 A1 | 4/2010 |
| WO | WO 2010/037016 A1 | 4/2010 |
| WO | WO 2010/037228 A8 | 4/2010 |
| WO | WO 2010/037714 A1 | 4/2010 |
| WO | WO 2010/039750 A2 | 4/2010 |

OTHER PUBLICATIONS

Colby, S., "Calculating Synergistic and Antagonistic Responses of Herbicide Combinations," *Weeds* 15(1):20-22, Weeds Science Society of America, USA (1967).
Comai, L., et al., "An Altered aroA Gene Product Confers Resistance to the Herbicide Glyphosate," *Science* 221(4608):370-371, Highwire Press, American Association for the Advancement of Science, USA (Jul. 1983).
Crickmore, N., et al., "Revision of the Nomenclature for the *Bacillus thuringiensis* Pesticidal Crystal Proteins," *Microbiology and Molecular Biology Reviews* 62(3):807-813, American Society for Microbiology, USA (Sep. 1998).
Gasser, C., et al., "Structure, Expression and Evolution of the 5-Enolpyruvylshikimate-3-phosphate Synthase Genes of Petunia and Tomato," *The Journal of Biological Chemistry* 263(9): 4280-4289, The American Society for Biochemistry and Molecular Biology, Inc., USA (Mar. 1988).
Malais, M. and Ravensberg, W., ed., Knowing and recognizing: The biology of glasshouse pests and their natural enemies, Revised edition, Koppert B.V., Berkel en Rodenrijs, Netherlands, 3 pages (1992).
Moellenbeck, D., et al., "Insecticidal Proteins from *Bacillus thuringiensis* Protect Corn from Corn Rootworms," *Nature Biotechnology* 19:668-672, Nature Publishing Group, New York, USA (Jul. 2001).
Schnepf, H. et al., "Characterization of Cry34/Cry35 Binary Insecticidal Proteins from Diverse *Bacillus thuringiensis* Strain Collections," *Applied and Environmental Microbiology* 71(4):1765-1774, American Society for Microbiology, Washington, USA (2005).
Shah, D., et al., "Engineering Herbicide Tolerance in Transgenic Plants," *Science* 233(4762):478-481, HighWire Press, American Association for the Advancement of Science, USA (Jul. 1986).
Tranel, P. and Wright, T., "Resistance of Weeds to ALS-inhibiting Herbicides: What have we learned?," *Weed Science* 50(6):700-712, Weed Science Society of America, KS, USA (2002).
Unverified English language Abstract of Chinese Patent Publication No. CN 1840655, Esp@cenet Database, 1 page (2006).
Unverified English language Abstract of German Patent Publication No. DE 10342673 A1, Esp@cenet Database, 1 page (2005).
English language Abstract of Japanese Patent Publication No. JP 2006-304779 A, Japanese Patent Office (JPO), 1 page (2006).
Unverified English language abstract of WO 99/57965 A1, Esp@cenet Database, 1 page (1999).
Unverified English language abstract of WO 02/02776 A1, Esp@cenet Database, 1 page (2002).
Unverified English language abstract of WO 2005/065453 A1, Esp@cenet Database, 1 page (2005).
Unverified English language abstract of WO 2005/090578 A1, Esp@cenet Database, 1 page (2005).
Unverified English language abstract of WO 2008/0224786 A1, Esp@cenet Database, 1 page (2008).
Unverified English language abstract of WO 01/14569 A2, Esp@cenet Database, 1 page (2001).
Unverified English language abstract of WO 2008/037902 A1, Esp@cenet Database, 1 page (2008).
Unverified English language abstract of WO 2009/065863 A1, Esp@cenet Database, 1 page (2009).
Unverified English language abstract of WO 2009/117853 A1, Esp@cenet Database, 1 page (2009).
Unverified English language abstract of WO 2009/145290 A1, Esp@cenet Database, 1 page (2009).
Bauer, T.A., et al., "Response of Selected Weed Species to Postemergence Imazethapyr and Bentazon," *Weed Tech*. 9:236-242, The Weed Science Society of America (1995).
Blackshaw, R.E., "HOE-39866 Use in Chemical Fallow Systems," *Weed Tech*. 3:420-428, The Weed Science Society of America (1989).
Blackshaw, R.E., "Synergistic Mixes of DPX-A7881 and Clopyralid in Canola (*Brassica napus*)," *Weed Tech*. 3:690-695, The Weed Science Society of America (1989).
Blackshaw, R.E., et al., "Herbicide Combinations for Postemergent Weed Control in Safflower (*Carthamus tinctorius*)," *Weed Tech*. 4:97-104, The Weed Science Society of America (1990).
Blouin, D.C., et al., "Analysis of Synergistic and Antagonistic Effects of Herbicides Using Nonlinear Mixed-Model Methodology," *Weed Tech*. 18:464-472, The Weed Science Society of America (2004).
Bradley, P.R., et al., "Response of Sorghum (*Sorghum bicolor*) to Atrazine, Ammonium Sulfate, and Glyphosate," *Weed Tech*. 14:15-18, The Weed Science Society of America (2000).

(56) References Cited

OTHER PUBLICATIONS

Buker, III, R.S., et al., "Confirmation and Control of a Paraquat-Tolerant Goosegrass (*Eleusine indica*) Biotype," *Weed Tech.* 16:309-313, The Weed Science Society of America (2002).

Burke, I.C., et al., "CGA-362622 Antagonizes Annual Grass Control with Clethodim," *Weed Tech.* 16:749-754, The Weed Science Society of America (2002).

Flint, J.L., et al., "Analyzing Herbicide Interactions, A Statistical Treatment of Colby's Method," *Weed Tech.* 2:304-309, The Weed Science Society of America (1988).

Gillespie, G.R., and Nalewaja, J.D., "Wheat (*Triticum aestivum*) Response to Triallate Plus Chlorsulfuron," *Weed Tech.* 3:20-23, The Weed Science Society of America (1989).

Green, J.M., et al., "Metribuzin and Chlorimuron Mixtures for Preemergence Broadleaf Weed Control in Soybeans, Glycine max," *Weed Tech.* 2:355-363, The Weed Science Society of America (1988).

Harker, K.N., and O'Sullivan, P.A., "Synergistic Mixtures of Sethoxydim and Fluazifop on Annual Grass Weeds," *Weed Tech.* 5:310-316, The Weed Science Society of America (1991).

Kent, L.M., et al., "Effect of Ammonium Sulfate, Imazapyr, and Environment on the Phytotoxicity of Imazethapyr," *Weed Tech.* 5:202-205, The Weed Science Society of America (1991).

Kotoula-Syka, E., et al., "Interactions between SAN 582H and Selected Safeners on Grain Sorghum (*Sorghum bicolor*) and Corn (*Zea mays*)," *Weed Tech.* 10:299-304, The Weed Science Society of America (1996).

Lanclos, D.Y., et al., "Glufosinate Tank-Mix Combinations in Glufosinate-Resistant Rice (*Oryza sativa*)," *Weed Tech.* 16:659-663, The Weed Science Society of America (2002).

Norris, J.L., et al., "Weed Control from Herbicide Combinations with Three Formulations of Glyphosate," *Weed Tech.* 15:552-558, The Weed Science Society of America (2001).

Novosel, K.M., et al., "Metolachlor Efficacy as Influenced by Three Acetolactate Synthase-Inhibiting Herbicides," *Weed Tech.* 12:248-253, The Weed Science Society of America (1998).

Palmer, E.W., et al., "Broadleaf Weed Control in Soybean (*Glycine max*) with CGA-277476 and Four Postemergence Herbicides," *Weed Tech.* 14:617-623, The Weed Science Society of America (2000).

Rummens, F.H.A., "An Improved Definition of Synergistic and Antagonistic Effects," *Weed Science* 23(1):4-6, The Weed Science Society of America, United States (1975).

Salzman, F.P., and Renner, K.A., "Response of Soybean to Combinations of Clomazone, Metribuzin, Linuron, Alachlor, and Atrazine," *Weed Tech.* 6:922-929, The Weed Science Society of America (1992).

Scott, R.C., et al., "Spray Adjuvant, Formulation, and Environmental Effects on Synergism from Post-Applied Tank Mixtures of SAN 582H with Fluazifop-P, Imazethapyr, and Sethoxydim," *Weed Tech.* 12:463-469, The Weed Science Society of America (1998).

Shaw, D.R. and Arnold, J.C., "Weed Control from Herbicide Combinations with Glyphosate," *Weed Tech.* 16:1-6, The Weed Science Society of America (2002).

Snipes, C.E., and Allen, R.L., "Interaction of Graminicides Applied in Combination with Pyrithiobac," *Weed Tech.* 10:889-892, The Weed Science Society of America (1996).

Sun, Y.-P. & Johnson, E.R., "Analysis of Joint Action of Insecticides Against House Flies", *J. Econ. Entomol.* 53:887-892, United States (1960).

Tammes, P.M.L., "Isoboles, A Graphic Representation of Synergism in Pesticides," *Neth. J. Plant Path.* 70:73-80, Springer, Germany (1964).

Wehtje, G. and Walker, R.H., "Interaction of Glyphosate and 2,4-DB for the Control of Selected Morningglory (*Ipomoea* spp.) Species," *Weed Tech.* 11:152-156, The Weed Science Society of America (1997).

Zhang, W., et al., "Fenoxaprop Interactions for Barnyardgrass (*Echinochloa crusgalli*) Control in Rice," *Weed Tech.* 19:293-297, The Weed Science Society of America (2005).

Buschman, L.L., et al., "Efficacy of Early Season Miticide Applications Against Spider Mites and Yield Response in Corn, 2003B," *Arthropod Management Tests* 30:F12 (4 PP), Entomological Society of America, United States (2005).

Elbert, A., et al., "Field Development of Oberon® for whitelfy and mite control in vegetable, cotton, corn, strawberries, ornamentals and tea," *Pflanzenschutz Nachrichten Bayer* 58(3):441-468, Bayer Leverkussen, Germany (2005.

International Search Report for International Application No. PCT/EP2011/050453, European Patent Office, Netherlands, mailed Oct. 7, 2011.

Office Action mailed Jul. 6, 2012, in U.S. Appl. No. 12/305,135, Fischer et al., filed Jan. 5, 2010.

Office Action mailed Dec. 27, 2012, in U.S. Appl. No. 12/305,135, Fischer et al., filed Jan. 5, 2010.

\* cited by examiner

ACARICIDAL AND/OR INSECTICIDAL ACTIVE INGREDIENT COMBINATIONS

The present invention relates to new active ingredient combinations composed of a known dihydrofuranone derivative on the one hand and of other known active pesticidal ingredients on the other hand, these combinations being extremely suitable for controlling animal pests, more particularly for controlling animal pests from the families of the Aleyrodidae, Thripidae, Psyllidae and Agromyzidae, and also, more particularly, from the order of the Acari.

It is already known that the dihydrofuranone derivative of the formula

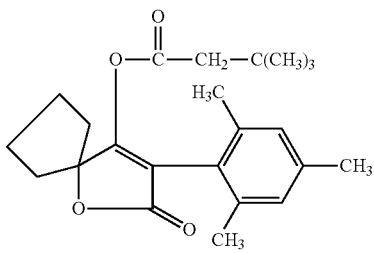

(I)

can be used for controlling animal pests, such as insects and unwanted acarids (cf. EP-A-0528156, WO 00/42850, WO 06/002824, WO 07/115,686). The activity of this compound, while good, nevertheless leaves something to be desired in certain cases at low application rates.

Additionally known are mixtures of (I) with other insecticides and/or acaricides: for example, WO 00/56156, WO 01/60158, WO 01/70027, WO 01/76369, WO 01/78511, WO 01/72125, WO 05/048712, WO 05/065453, WO 07/098,852, DE-A-10342673.

It has now been found that active ingredient combinations comprising the dihydrofuranone derivative of the formula

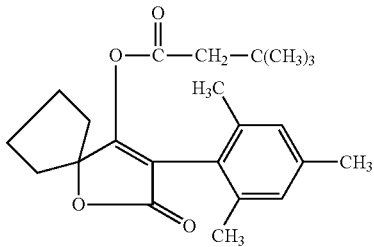

(I)

and active ingredients from the IRAC classes of the sodium channel modulators/blockers and/or site I electron transport inhibitors and/or chloride channel activators, and/or inhibitors of magnesium-stimulated ATPase and/or bifenazate, are especially suitable for controlling animal pests from the families of the Aleyrodidae, Thripidae, Psyllidae and Agromyzidae, and also, more particularly, from the order of the Acari, in annual or perennial crops. Surprisingly, not only, in particular, is the insecticidal and/or acaricidal activity of the active ingredient combinations higher than the sum of the activities of the individual active ingredients, but also, unexpectedly, an improved preservation of beneficial species by the active ingredient combination is observed.

Particularly preferred are the active ingredient combinations comprising the compound of the formula (I) and at least one of the following compounds:

(1) the phenylhydrazine derivative of the formula

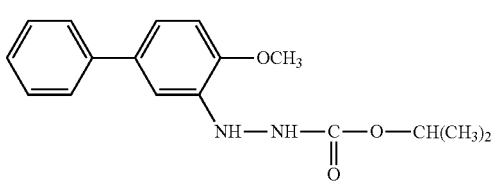

(II)

bifenazate, known from WO 93/10 083
and/or
(2) from the class of the site (I) electron transport inhibitors, the pyrazole derivative of the formula

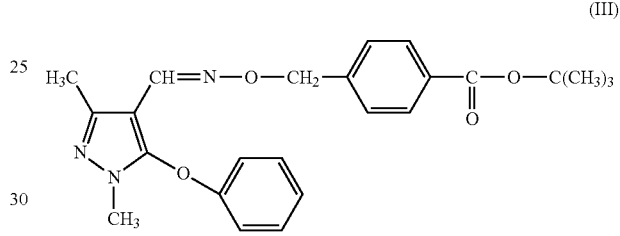

(III)

fenpyroximate, known from EP-A-234 045
and/or
the pyridazinone derivative of the formula

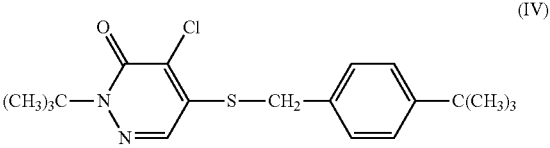 [SMILES: CC(C)(C)c1ccc(CSc2cnn(C(C)(C)C)c(=O)c2Cl)cc1]

(IV)

pyridaben, known from EP-A-134 439
and/or
fenazaquin

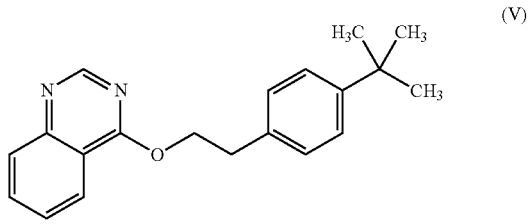 [SMILES: CC(C)(C)c1ccc(CCOc2ncnc3ccccc23)cc1]

(V)

known from EP-A-326 329
and/or
(3) from the class of the chloride channel activators
abamectin (VI) known from DE-A-02717040
and/or
emamectin benzoate (VII) known from EP-A-0089202 and/or
(4) from the class of sodium channel modulators/blockers

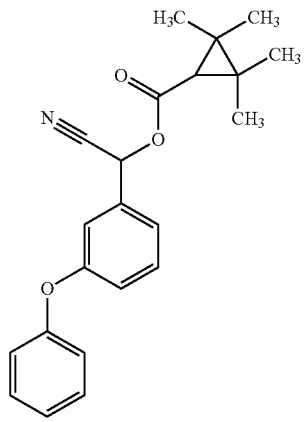

fenpropathrin, known from DE-A-02231312
and/or
(5) from the class of the magnesium-stimulated ATPase ingredients

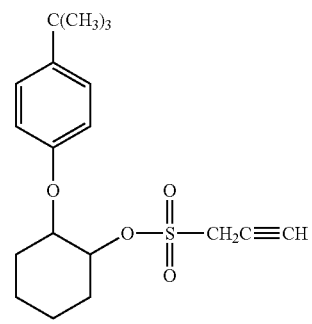

propargite, known from U.S. Pat. No. 3,272,854.

The active ingredient combinations comprise not only the active ingredient of the formula (I) but also at least one active ingredient from the compounds of the formulae (II) to (IX).

The present invention relates, furthermore, to a process for improving the utilization of the production potential of a transgenic plant, characterized in that the plant is treated with an effective amount of the active ingredient combinations of the invention. It is already known that the production potential of a transgenic plant can be improved through treatment with the compound of the formula (I) (WO 2009/132779). This activity is boosted through treatment with the active ingredient combinations of the invention.

The present invention additionally relates to new combinations which are composed of the aforementioned active ingredient combinations (also defined below as mixture(s)) on the one hand and beneficial species (natural enemies) on the other hand and which are extremely suitable for controlling animal pests such as insects and/or unwanted acarids, more particularly for controlling animal pests from the families of the Aleyrodidae, Thripidae, Psyllidae and Agromyzidae, and also, more particularly, from the order of the Acari.

It is already known, furthermore, that numerous beneficial species are used for controlling insects and spider mites: Knowing and recognizing; M. H. Malais, W. J. Ravensberg, published by Koppert B. V., Reed Business Information (2003). However, the use of beneficial species alone is not always satisfactory.

It is also already known that the dihydrofuranone derivative of the formula (I) exhibits improved insecticidal and acaricidal properties in combination with beneficial species—see, for example WO 07/144,087—and is recommended for IPM programmes.

It has now been found that active ingredient combinations (mixtures) comprising the compound of the formula (I) and a co-component of the formulae (II) to (IX), more particular of the formulae (VI) and (VII), especially co-components of the formula (VI), in proportions of 5:1 to 50:1, preferably 10:1 to 30:1, very preferably 20:1, can be employed in combination with beneficial species from the orders or suborders of the Araneae, Acari, Dermaptera, Hymenoptera, Coleoptera, Neuroptera, Thysanoptera, Heteroptera, Diptera, Hemiptera, Demiaptera and/or Parasitiformes, and possess very good insecticidal and/or acaricidal properties.

The insecticidal and/or acaricidal activity of the mixture/beneficial species combinations of the invention is, surprisingly, better than the activities of the mixture and of the beneficial species alone. There is an unforeseeable boost in effect. It has also been found that it is possible with mixture/beneficial species combinations to replace applications of old, toxicologically and/or environmentally objectionable active ingredients, with retention of a comparable activity, and this is beneficial above all to the safety of users and/or of the environment, and may even make it possible to reduce spray applications. The mixture/beneficial species combinations are employed by treating the plants or plant parts advantageously first with the mixtures of the invention, and thereafter applying the beneficial species.

The invention also provides a kit comprising the abovementioned active ingredient combinations and beneficial species.

The present invention relates, furthermore, to a process for improving the utilization of the production potential of a transgenic plant, characterized in that the plant is treated with an effective amount of the mixture/beneficial species combinations of the invention.

The mixture/beneficial species combinations of the invention comprise not only at least one of the abovementioned active ingredient combinations (mixtures) but also at least one beneficial species from the orders and suborders listed below.

The active ingredient combinations (mixtures) may, furthermore, also comprise other components with fungicidal, acaricidal or insecticidal activity.

When the active ingredients are present in particular weight proportions in the active ingredient combinations of the invention, the enhanced activity is manifested to a particularly marked extent. However, the weight proportions of the active ingredients in the active ingredient combinations can be varied within a relatively wide range. Generally speaking, the combinations of the invention comprise the active ingredient of the formula (I) and the co-component in the preferred and particularly preferred proportions indicated in the tables below:

the mixing ratios are based on weight ratios. The ratio should be understood as active ingredient of the formula (I):co-component

| Co-component | preferred mixing ratio | particularly preferred mixing ratio | especially preferred mixing ratio |
| --- | --- | --- | --- |
| Bifenazate (II) | 5:1 to 1:25 | 5:1 to 1:5 | |
| Fenpyroximate (III) | 25:1 to 1:25 | 5:1 to 1:5 | |
| Pyridaben (IV) | 25:1 to 1:25 | 5:1 to 1:5 | |
| Fenazaquin (V) | 25:1 to 1:25 | 5:1 to 1:5 | |
| Abamectin (VI) | 125:1 to 1:25 | 25:1 to 1:5 | 20:1 |

| Co-component | preferred mixing ratio | particularly preferred mixing ratio | especially preferred mixing ratio |
| --- | --- | --- | --- |
| Emamectin benzoate (VII) | 125:1 to 1:25 | 5:1 to 1:5 | |
| Fenpropathrin (VIII) | 25:1 to 1:25 | 5:1 to 1:5 | |
| Propargite (IX) | 10:1 to 1:25 | 5:1 to 1:5 | |

Beneficial species contemplated include with particular preference those from the following families:

From the family of Eumenidae, particular preference is given to: *Eumenes* spp., *Oplomerus* spp., in crops such as, for example, pome fruit, stone fruit, vegetables, ornamental plants, conifers and spices.

From the family of Sphecidae, particular preference is given to: *Ammophila sabulos, Cerceris arenaria*, in crops such as, for example, pome fruit, stone fruit, vegetables, ornamental plants, conifers and spices.

From the family of Vespidae, particular preference is given to: *Polistes* spp. *Vespa* spp., *Dolichovespula* spp., *Vespula* spp., *Paravespula* spp., in crops such as, for example, pome fruit, stone fruit, vegetables, ornamental plants, conifers and spices.

From the family of Aphelinidae, particular preference is given to: *Coccophagus* spp., *Encarsia* spp., for example, *Encarsia formosa, Aphytis* spp., *Aphelinus* spp., for example, *Aphelinus mali, Aphelinus abdominalis, Erelmocerus* spp., for example, *Erelmocerus erimicus, Erelmocerus mundus, Prospaltella* spp., in crops such as, for example, pome fruit, stone fruit, vegetables, ornamental plants, conifers and spices.

From the family of Trichogrammatidae, particular preference is given to: *Trichogramma* spp., for example, *Trichogamma brassicae*, in crops such as, for example, pome fruit, stone fruit, vegetables, ornamental plants, conifers and spices.

From the family of Encyrtidae, particular preference is given to: *Encyrtus fuscicollis, Aphidencyrtrus* spp., in crops such as, for example, pome fruit, stone fruit, vegetables, ornamental plants, conifers, spices and afforestations.

From the family of Mymaridae, in crops such as, for example, pome fruit, stone fruit, vegetables, ornamental plants, conifers and spices.

From the family of Ichneumoidae, particular preference is given to: *Coccigomymus* spp. *Diadegma* spp., *Glypta* spp., *Ophion* spp., *Pimpla* spp., in crops such as, for example, pome fruit, stone fruit, vegetables, ornamental plants, conifers and spices.

From the family of Eulophidae, particular preference is given to: *Dyglyphus* spp., for example, *Dyglyphus isaea, Eulophus viridula, Colpoclypeus florus*, in crops such as, for example, pome fruit, stone fruit, vegetables, ornamental plants, conifers, maize and spices.

From the family of Alloxystidae, particular preference is given to: *Alloxysta* spp., in crops such as, for example, pome fruit, stone fruit, vegetables, ornamental plants, conifers and spices.

From the family of Megaspilidae, particular preference is given to: *Dendrocerus* spp., in crops such as, for example, pome fruit, stone fruit, vegetables, ornamental plants, conifers and spices.

From the family of Braconidae, particular preference is given to: *Aphidrus* spp., *Praon* spp., *Opius* spp., *Dacnusa* spp., for example, *Dacnusa sibiria, Apanteles* spp., *Ascogaster* spp., *Macrocentrus* spp., in crops such as, for example, pome fruit, stone fruit, vegetables, ornamental plants, conifers and spices.

From the family of Aphidiidae, particular preference is given to: *Aphidius* spp., for example, *Aphidius colemani, Aphidius ervi, Diaeretiella* spp., *Lysiphlebus* spp., in crops such as, for example, pome fruit, stone fruit, vegetables, ornamental plants, conifers and spices.

From the family of Coccinellidae, particular preference is given to: *Harmonia* spp., *Coccinella* spp., for example, *Coccinella septempunctata, Adalia* spp., for example, *Adalia bipunctata, Calvia* spp., *Chilocorus* spp., for example, *Chilocorus bipustulatus, Scymnus* spp., *Cryptolaemus montrouzieri, Exochomus* spp., *Stethorus* spp., for example, *Scymnus abietes, Scymnus interruptus, Anatis* spp., *Rhizobius* spp., *Thea* spp., in crops such as, for example, pome fruit, stone fruit, vegetables, ornamental plants, conifers and spices.

From the family of Staphylernidae, particular preference is given to: *Aleochara* spp., *Aligota* spp., *Philonthus* spp., *Staphylinus* spp., in crops such as, for example, pome fruit, stone fruit, vegetables, ornamental plants, conifers and spices.

From the family of Chrysopidae, particular preference is given to: *Chrysopa* spp., for example, *Chrysopa oculata, Chrysopa perla, Chrysopa carnea, Chrysopa flava, Chrysopa septempunctata, Chrysoperla* spp., *Chrysopidia* spp., for example, *Chrysopidia ciliata, Hypochrysa* spp., for example, *Hypochrysa elegans*, in crops such as, for example, pome fruit, stone fruit, vegetables, ornamental plants, conifers and spices.

From the family of Hemerobiidae, particular preference is given to: *Hemerobius* spp., for example, *Hemerobius fenestratus, Hemerobius humulinus, Hemerobius micans, Hemerobius nitidulus, Hemerobius pini, Wesmaelius* spp., for example, *Wesmaelius nervosus*, in crops such as, for example, pome fruit, stone fruit, vegetables, ornamental plants, conifers and spices.

From the family of Anthocoridae, particular preference is given to: *Anthocoris* spp., for example, *Anthocoris nemoralis, Anthocoris nemorum, Orius* spp., for example, *Orius majusculus, Orius minutus, Orius laevigatus, Orius insidiosus, Orius niger, Orius vicinus*, in crops such as, for example, pome fruit, stone fruit, vegetables, ornamental plants, conifers and spices.

From the family of Miridae, particular preference is given to: *Atractotomus* spp., for example, *Atractotomus mali, Blepharidopterus* spp., for example, *Blepharidopterus angulatus, Camylomma* spp., for example, *Camylomma verbasci, Deraeocoris* spp., *Macrolophus* spp., for example, *Macrolophus caliginosus*, in crops such as, for example, cotton, pome fruit, stone fruit, vegetables, ornamental plants, conifers and spices.

From the family of Pentatomidae, particular preference is given to: *Arma* spp., *Podisus* spp., for example, *Podisus maculiventris*, in crops such as, for example, pome fruit, stone fruit, vegetables, ornamental plants, conifers and spices.

From the family of Nabidae, particular preference is given to: *Nabis* spp., for example, *Nabis apterus*, in crops such as, for example, pome fruit, stone fruit, vegetables, ornamental plants, conifers and spices.

From the family of Reduviidae, particular preference is given to: *Empicornis vagabundus, Reduvius personatus, Rhinocoris* spp., in crops such as, for example, pome fruit, stone fruit, vegetables, ornamental plants, conifers and spices.

From the family of Tachinidae, particular preference is given to: *Bessa fugax, Cyzenius albicans, Compsileura concinnata, Elodia tragica, Exorista larvarum, Lyphia dubia*, in crops such as, for example, pome fruit, stone fruit, vegetables, ornamental plants, conifers and spices.

From the family of Syrphidae, particular preference is given to: *Dasysyrphus* spp., *Episyrphus balteatus, Melangyna triangulata, Melanostoma* spp., *Metasyrphus* spp., *Platycheirus* spp., *Syrphus* spp., in crops such as, for example, pome fruit, stone fruit, vegetables, ornamental plants, conifers and spices.

From the family of Cecidomyiidae, particular preference is given to: *Aphidoletes aphidimyza, Feltiella acarisuga*, in crops such as, for example, pome fruit, stone fruit, vegetables, ornamental plants, conifers and spices.

From the family of Phytoseidae, particular preference is given to: *Amblyseius* spp., *Thyphlodromus* spp., *Phytoseiulus* spp., in crops such as pome fruit, stone fruit, vegetables, ornamental plants and spices.

The active ingredient combinations (mixtures) of the invention and also the mixture/beneficial species combinations of the invention combine good plant tolerance, favourable homeotherm toxicity and good environment compatibility with capacity for protection of plants and plant organs, for increasing harvest yields, for improving the quality of harvested produce, and for controlling animal pests, more particularly insects, arachnids, helminths, nematodes and molluscs which are prevalent in agriculture, in horticulture, in animal husbandry, in forests, in gardens and leisure facilities, in the protection of store houses and materials, and in the hygiene sector. They can be used with preference as crop protectants. They are effective against species with normal sensitivity and resistant species, and also against certain development stages or all development stages.

The pests referred to above include the following:

Pests from the phylum Arthropoda, more particularly from the subclass of the Acari, e.g. *Acarus* spp., *Aceria sheldoni, Aculops* spp., *Aculus* spp., *Amblyomma* spp., *Amphitetranychus viennensis, Argas* spp., *Boophilus* spp., *Brevipalpus* spp., *Bryobia praetiosa, Chorioptes* spp., *Dermanyssus gallinae, Dermatophagoides pteronyssinus, Dermatophagoides farinae, Dermacentor* spp., *Eotetranychus* spp., *Epitrimerus pyri, Eutetranychus* spp., *Eriophyes* spp., *Halotydeus destructor, Hemitarsonemus* spp., *Hyalomma* spp., *Ixodes* spp., *Metatetranychus* spp., *Nuphersa* spp., *Oligonychus* spp., *Ornithodorus* spp., *Ornithonyssus* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Steneotarsonemus* spp., *Steneotarsonemus spinki, Tarsonemus* spp., *Tetranychus* spp., *Vasates lycopersici*.

From the order of the *Homoptera*, more particularly from the family of the Aleyrodidae, e.g. *Aleyrodes proletella, Aleurolobus barodensis, Aleurothrixus floccosus, Bemisia tabaci, Dialeurodes citri, Parabemisia myricae, Siphoninus phillyreae, Trialeurodes vaporariorum* and from the family of Psyllidae, e.g. *Acizzia acaciaebaileyanae, Acizzia dodonaeae, Acizzia uncatoides, Agonoscena* spp., *Allocaridara malayensis, Arytainilla* spp., *Blastopsylla occidentalis, Borеioglycaspis melaleucae, Cacopsylla* spp., *Cryptoneossa* spp., *Ctenarytaina* spp., *Diaphorina citri, Eucalyptolyma* spp., *Euphyllura* spp., *Glycaspis* spp., *Heteropsylla cubana, Heteropsylla spinulosa, Pachypsylla* spp., *Prosopidopsylla flava, Psyllopsis* spp., *Psylla* spp. and *Tetragonocephela* spp.

From the order of the Thysanoptera, more particularly form the family of the Thriphidae, e.g. *Anaphothrips obscurus, Baliothrips biformis, Drepanothrips reuteri, Frankliniella* spp., *Heliothrips* spp., *Hercinothrips femoralis, Rhipiphorothrips cruentatus, Scirtothrips* spp., *Taeniothrips cardamomi* and *Thrips* spp.

From the order of the Diptera, more particularly from the family of the Agromyzidae, e.g. *Agromyza* spp., *Liriomyza* spp., and *Tipula* spp.

In annual crops such as, for example, vegetables, melons, ornamental plants, maize, soya, cotton, and also in perennial plants, such as, for example, citrus, pome fruit and stone fruit, spices, conifers and other ornamental plants, and also in afforestations.

The crops to be protected which have only been described in general terms are described in greater detail and specified hereinbelow. Thus, as regards the use, vegetables are understood as meaning for example fruiting vegetables and inflorescences as vegetables, for example bell peppers, chilies, tomatoes, aubergines, cucumbers, pumpkins, courgettes, broad beans, climbing and dwarf beans, peas, artichokes; but also leafy vegetables, for example head-forming lettuce, chicory, endives, various types of cress, of rocket, lamb's lettuce, iceberg lettuce, leeks, spinach, Swiss chard;

furthermore tuber vegetables, root vegetables and stem vegetables, for example celeriac/celery, beetroot, carrots, radish, horseradish, scorzonera, asparagus, beet for human consumption, palm hearts, bamboo shoots, furthermore bulb vegetables, for example onions, leeks, Florence fennel, garlic;

Regarding the use, perennial crops are understood as meaning citrus, such as, for example, oranges, grapefruits, tangerines, lemons, limes, Seville oranges, kumquats, satsumas;

but also pome fruit such as, for example, apples, pears and quinces, and stone fruit, such as, for example, peaches, nectarines, cherries, plums, quetsch, apricots;

furthermore grapevines, hops, olives, tea and tropical crops such as, for example, mangoes, papayas, figs, pineapples, dates, bananas, durians, kaki fruit, coconuts, cacao, coffee, avocados, lychees, maracujas, guavas, palm fruits moreover almonds and nuts such as, for example, hazelnuts, walnuts, pistachios, cashew nuts, para nuts, pecan nuts, butternuts, chestnuts, hickory nuts, *macadamia* nuts, peanuts, moreover also soft fruit such as, for example, currants, gooseberries, raspberries, blackberries, blueberries, strawberries, cranberries, including American cranberries, kiwi fruit.

As regards the use, ornamentals are understood as meaning annual and perennial plants, for example cut flowers such as, for example, roses, carnations, gerbera, lilies, marguerites, chrysanthemums, tulips, narcissus, anemones, poppies, amaryllis, dahlias, azaleas, hibiscus, but also for example bedding plants, pot plants and perennials such as, for example, roses, Tagetes, violas, geraniums, fuchsias, hibiscus, chrysanthemums, busy lizzie, cyclamen, African violet, sunflowers, begonias, furthermore for example bushes and conifers such as, for example, *ficus*, rhododendron, firs, spruces, pines, including umbrella pines, yews, juniper, oleander.

As regards the use, spices are understood as meaning annual and perennial plants such as, for example, aniseed, chili pepper, paprika, pepper, vanilla, marjoram, thyme, cloves, juniper berries, cinnamon, tarragon, coriander, saffron, ginger.

In accordance with the invention all plants and plant parts can be treated. By plants here are meant all plants and plant populations, such as desirable and unwanted wild plants or crop plants (including naturally occurring crop plants). Crop plants may be plants which are obtainable by conventional breeding and optimization methods or by biotechnological and gene-technology methods or by combinations of these methods, including the transgenic plants and including plant varieties which may or may not be protectable by varietal property rights or plant breeder's rights. By plant parts are meant all above-ground and below-ground parts and organs of the plants, such as shoot, leaf, blossom and root, including for example leaves, needles, stems, branches, blossoms, fruiting bodies, fruits and seeds, and also roots, corms and rhizomes. The plant parts also include harvested produce, and also vegetative and generative propagation material, examples being cuttings, corms, rhizomes, runners and seeds.

The treatment, in accordance with the invention, of the plants and plant parts with the active ingredient combinations or mixture/beneficial species combinations takes place directly or by action on their environment, habitat or storage area, in accordance with the typical methods of treatment, as for example by dipping, spraying, vaporizing, fogging, scattering, brush application, injection, and, in the case of propagation material, especially in the case of seeds, additionally by coating with one or more coats.

As already mentioned above, it is possible in accordance with the invention to treat all plants and their parts. In one preferred embodiment, plant species and plant cultivars occurring in the wild or obtained by conventional biological breeding methods, such as crossing or protoplast fusion, and also parts of such plants, are treated. In another preferred embodiment, transgenic plants and plant cultivars obtained by gene-technology methods, optionally in combination with conventional methods, i.e. genetically modified organisms, and parts thereof are treated. The terms "parts" or "parts of plants" or "plant parts" is elucidated above.

With particular preference, plants treated in accordance with the invention are those of the respective plant cultivars in use or commercially standard plant cultivars. By plant cultivars are meant plants having new properties ("traits"), which have been bred alternatively by conventional breeding, by mutagenesis or by recombinant DNA techniques. These may be varieties, biotypes and genotypes.

Depending on the plant species or plant cultivars, their location and growth conditions (soils, climate, vegetation period, nutrition), the treatment according to the invention may also result in superadditive ("synergistic") effects. Thus, for example, reduced application rates and/or widening of the activity spectrum, and/or a boost in the activity of the compounds and compositions that can be used in accordance with the invention, better plant growth, increased tolerance towards high or low temperatures, increased tolerance to drought or to rain content or soil salt content, increased flowering performance, easier harvesting, accelerated maturation, higher harvest yields, higher quality and/or higher nutritional value on the part of the harvested products, longer storage life and/or better processability of the harvested products, are possible, and exceed the effects which could actually have been expected.

The preferred transgenic plants or plant cultivars (i.e., those obtained by gene technology) for treatment in accordance with the invention include all plants obtained by the gene-technology modification of genetic material that endows these plants with particular advantageous valuable properties ("traits"). Examples of such properties are better plant growth, increased tolerance towards high or low temperatures, increased tolerance to drought or to rain content or soil salt content, increased flowering performance, easier harvesting, accelerated maturation, higher harvest yields, higher quality and/or higher nutritional value on the part of the harvested products, longer storage life and/or better processability of the harvested products. Further and particularly emphasized examples of such properties are an increased defence of the plants against animal and microbial pests, such as against insects, mites, phytopathogenic fungi, bacteria and/or viruses, and also increased tolerance by the plants of certain active herbicidal ingredients. Examples of transgenic plants include the major crop plants, such as cereals (wheat, rice), maize, soya, potatoes, cotton, tobacco, oilseed rape, and also fruit plants (with the fruits apples, pears, citrus fruits and grapes), with particular emphasis being given to maize, soya, potatoes, cotton, tobacco and oilseed rape. Traits that are particularly emphasized are the increased defence of the plants against insects, arachnids, nematodes and molluscs, by means of toxins produced in the plants, more particularly those produced in the plants by the genetic material from *Bacillus thuringiensis* (e.g. by the genes CryIA(a), CryIA(b), CryIA(c), CryIIA, CryIIIA, CryIIIB2, Cry9c Cry2Ab, Cry3Bb and CryIF, and also combinations thereof) (hereinafter "Bt plants"). Also particularly emphasized as traits are the increased defence of plants against fungi, bacteria and viruses through systemic acquired resistance (SAR), systemin, phytoalexins, elicitors and also resistance genes, and proteins and toxins expressed accordingly. Further traits that are parituclalry emphasized are the increased tolerance by the plants with respect to certain active herbicidal ingredients, examples being imida-zolinones, sulphonylureas, glyphosates or phosphinotricin (e.g. "PAT" gene). The genes in question which impart the desired traits may also occur in combinations with one another in the transgenic plants. Examples of "Bt plants" include maize varieties, cotton varieties, soya varieties and potato varieties which are sold under the trade names YIELD GARD® (e.g. maize, cotton, soya), KnockOut® (e.g. maize), StarLink® (e.g. maize), Bollgard® (cotton), Nucotn® (cotton) and NewLeaf® (potatoes). Examples of herbicide-tolerant plants include maize varieties, cotton varities and soya varieties which are sold under the trade names Roundup Ready® (glyphosate tolerance, e.g. maize, cotton, soya), Liberty Link® (phosphinotricin tolerance, e.g. oilseed rape), IMI® (tolerance towards imidazolinones) and STS® (tolerance towards sulphonylureas, e.g. maize). Herbicide-resistant plants (bred conventionally for herbicide tolerance) also include the varieties (e.g. maize) sold under the Clearfield® name. It will be appreciated that these remarks also apply to plant cultivars which will be developed or come onto the market in the future and which have the aforementioned genetic properties ("traits") or such properties/traits to be developed in the future.

According to the invention all plants and plant parts can be treated. By plants is meant all plants and plant populations such as desirable and undesirable wild plants, cultivars and plant varieties (whether or not protectable by plant variety or plant breeder's rights). Cultivars and plant varieties can be plants obtained by conventional propagation and breeding methods which can be assisted or supplemented by one or more biotechnological methods such as by use of double haploids, protoplast fusion, random and directed mutagenesis, molecular or genetic markers or by bioengineering and genetic engineering methods. By plant parts is meant all above ground and below ground parts and organs of plants such as shoot, leaf, blossom and root, whereby for example leaves, needles, stems, branches, blossoms, fruiting bodies, fruits and seed as well as roots, corms and rhizomes are listed. Crops and vegetative and generative propagating material, for example cuttings, corms, rhizomes, runners and seeds also belong to plant parts.

Among the plants that can be protected by the method according to the invention, mention may be made of major field crops like corn, soybean, cotton, *Brassica* oilseeds such as *Brassica napus* (e.g. canola), *Brassica rapa, B. juncea* (e.g. mustard) and *Brassica carinata*, rice, wheat, sugarbeet, sugarcane, oats, lye, barley, millet, triticale, flax, vine and various fruits and vegetables of various botanical taxa such as Rosaceae sp. (for instance pip fruit such as apples and pears, but also stone fruit such as apricots, cherries, almonds and peaches, berry fruits such as strawberries), Ribesioidae sp., Juglandaceae sp., Betulaceae sp., Anacardiaceae sp., Fagaceae sp., Moraceae sp., Oleaceae sp., Actinidaceae sp., Lauraceae sp., Musaceae sp. (for instance banana trees and plantings), Rubiaceae sp. (for instance coffee), Theaceae sp., Sterculiceae sp., Rutaceae sp. (for instance lemons, oranges and grapefruit); Solanaceae sp. (for instance tomatoes, potatoes, peppers, eggplant), Liliaceae sp., Compositiae sp. (for instance lettuce, artichoke and chicory—including root chicory, endive or common chicory), Umbelliferae sp. (for instance carrot, parsley, celery and celeriac), Cucurbitaceae sp. (for instance cucumber—including pickling cucumber, squash, watermelon, gourds and melons), Alliaceae sp. (for instance onions and leek), Cruciferae sp. (for instance white cabbage, red cabbage, broccoli, cauliflower, brussel sprouts, pak Choi, kohlrabi, radish, horseradish, cress, Chinese cabbage), Leguminosae sp. (for instance peanuts, peas and beans—such as climbing beans and broad beans), Chenopodiaceae sp. (for instance mangold, spinach beet, spinach, beetroots), Malvaceae (for instance okra), Asparagaceae (for instance asparagus); horticultural and forest crops; ornamental plants; as well as genetically modified homologues of these crops.

The method of treatment according to the invention can be used in the treatment of genetically modified organisms (GMOs), e.g. plants or seeds. Genetically modified plants (or transgenic plants) are plants of which a heterologous gene has been stably integrated into the genome. The expression "heterologous gene" essentially means a gene which is provided or assembled outside the plant and when introduced in the nuclear, chloroplastic or mitochondrial genome gives the transformed plant new or improved agronomic or other properties by expressing a protein or polypeptide of interest or by downregulating or silencing other gene(s) which are present in the plant (using for example, antisense technology, cosuppression technology or RNA interference—RNAi-technology). A heterologous gene that is located in the genome is also called a transgene. A transgene that is defined by its particular location in the plant genome is called a transformation or transgenic event.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the active compounds and compositions which can be used according to the invention, better plant growth, increased tolerance to high or low temperatures, increased tolerance to drought or to water or soil salt content, increased flowering performance, easier harvesting, accelerated maturation, higher harvest yields, bigger fruits, larger plant height, greener leaf color, earlier flowering, higher quality and/or a higher nutritional value of the harvested products, higher sugar concentration within the fruits, better storage stability and/or processability of the harvested products are possible, which exceed the effects which were actually to be expected.

At certain application rates, the active compound combinations according to the invention may also have a strengthening effect in plants. Accordingly, they are also suitable for mobilizing the defense system of the plant against attack by unwanted microorganisms. This may, if appropriate, be one of the reasons for the enhanced activity of the combinations according to the invention, for example against fungi. Plant-strengthening (resistance-inducing) substances are to be understood as meaning, in the present context, those substances or combinations of substances which are capable of stimulating the defense system of plants in such a way that, when subsequently inoculated with unwanted microorganisms, the treated plants display a substantial degree of resistance to these microorganisms. In the present case, unwanted microorganisms are to be understood as meaning phytopathogenic fungi, bacteria and viruses. Thus, the substances according to the invention can be employed for protecting plants against attack by the abovementioned pathogens within a certain period of time after the treatment. The period of time within which protection is effected generally extends from 1 to 10 days, preferably 1 to 7 days, after the treatment of the plants with the active compounds.

Plants and plant cultivars which are preferably treated according to the invention include all plants which have genetic material which impart particularly advantageous, useful traits to these plants (whether obtained by breeding and/or biotechnological means).

Plants and plant cultivars which are also preferably treated according to the invention are resistant against one or more biotic stresses, i.e. said plants show a better defense against animal and microbial pests, such as against nematodes, insects, mites, phytopathogenic fungi, bacteria, viruses and/or viroids.

Examples of nematode resitant plants are described in e.g. U.S. patent application Ser. Nos. 11/765,491, 11/765,494, 10/926,819, 10/782,020, 12/032,479, 10/783,417, 10/782,096, 11/657,964, 12/192,904, 11/396,808, 12/166,253, 12/166,239, 12/166,124, 12/166,209, 11/762,886, 12/364,335, 11/763,947, 12/252,453, 12/209,354, 12/491,396 or 12/497,221

Plants and plant cultivars which may also be treated according to the invention are those plants which are resistant to one or more abiotic stresses. Abiotic stress conditions may include, for example, drought, cold temperature exposure, heat exposure, osmotic stress, flooding, increased soil salinity, increased mineral exposure, ozone exposure, high light exposure, limited availability of nitrogen nutrients, limited availability of phosphorus nutrients, shade avoidance.

Plants and plant cultivars which may also be treated according to the invention, are those plants characterized by enhanced yield characteristics. Increased yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can furthermore be affected by improved plant architecture (under stress and non-stress conditions), including but not limited to, early flowering, flowering control for hybrid seed production, seedling vigor, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content, protein content, oil content and composition, nutritional value, reduction in anti-nutritional compounds, improved processability and better storage stability.

Examples of plants with the above-mentioned traits are non-exhaustively listed in Table A.

Plants that may be treated according to the invention are hybrid plants that already express the characteristic of heterosis or hybrid vigor which results in generally higher yield, vigor, health and resistance towards biotic and abiotic stresses. Such plants are typically made by crossing an inbred male-sterile parent line (the female parent) with another inbred male-fertile parent line (the male parent). Hybrid seed is typically harvested from the male sterile plants and sold to growers. Male sterile plants can sometimes (e.g. in corn) be produced by detasseling, i.e. the mechanical removal of the male reproductive organs (or male flowers) but, more typically, male sterility is the result of genetic determinants in the plant genome. In that case, and especially when seed is the desired product to be harvested from the hybrid plants it is typically useful to ensure that male fertility in the hybrid plants is fully restored. This can be accomplished by ensuring that the male parents have appropriate fertility restorer genes which are capable of restoring the male fertility in hybrid plants that contain the genetic determinants responsible for male-sterility. Genetic determinants for male sterility may be located in the cytoplasm. Examples of cytoplasmic male sterility (CMS) were for instance described in *Brassica* species (WO 92/05251, WO 95/09910, WO 98/27806, WO 05/002324, WO 06/021972 and U.S. Pat. No. 6,229,072). However, genetic determinants for male sterility can also be located in the nuclear genome. Male sterile plants can also be obtained by plant biotechnology methods such as genetic engineering. A particularly useful means of obtaining male-sterile plants is described in WO 89/10396 in which, for example, a ribonuclease such as barnase is selectively expressed in the tapetum cells in the stamens. Fertility can then be restored by expression in the tapetum cells of a ribonuclease inhibitor such as barstar (e.g. WO 91/02069).

Plants or plant cultivars (obtained by plant biotechnology methods such as genetic engineering) which may be treated according to the invention are herbicide-tolerant plants, i.e. plants made tolerant to one or more given herbicides. Such plants can be obtained either by genetic transformation, or by selection of plants containing a mutation imparting such herbicide tolerance.

Herbicide-resistant plants are for example glyphosate-tolerant plants, i.e. plants made tolerant to the herbicide glyphosate or salts thereof. Plants can be made tolerant to glyphosate through different means. For example, glyphosate-tolerant plants can be obtained by transforming the plant with a gene encoding the enzyme 5-enolpyruvylshikimate-3-phosphate synthase (EPSPS). Examples of such EPSPS genes are the AroA gene (mutant CT7) of the bacterium *Salmonella typhimurium* (Comai et al., 1983, Science 221, 370-371), the CP4 gene of the bacterium *Agrobacterium* sp. (Barry et al., 1992, Curr. Topics Plant Physiol. 7, 139-145), the genes encoding a Petunia EPSPS (Shah et al., 1986, Science 233, 478-481), a Tomato EPSPS (Gasser et al., 1988, J. Biol. Chem. 263, 4280-4289), or an *Eleusine* EPSPS (WO 01/66704). It can also be a mutated EPSPS as described in for example EP 0837944, WO 00/66746, WO 00/66747 or WO02/26995. Glyphosate-tolerant plants can also be obtained by expressing a gene that encodes a glyphosate oxido-reductase enzyme as described in U.S. Pat. Nos. 5,776,760 and 5,463,175. Glyphosate-tolerant plants can also be obtained by expressing a gene that encodes a glyphosate acetyl transferase enzyme as described in for example WO 02/36782, WO 03/092360, WO 05/012515 and WO 07/024,782. Glyphosate-tolerant plants can also be obtained by selecting plants containing naturally-occurring mutations of the above-mentioned genes, as described in for example WO 01/024615 or WO 03/013226. Plants expressing EPSPS genes that confer glyphosate tolerance are described in e.g. U.S. patent application Ser. Nos. 11/517,991, 10/739,610, 12/139,408, 12/352,532, 11/312, 866, 11/315,678, 12/421,292, 11/400,598, 11/651,752, 11/681,285, 11/605,824, 12/468,205, 11/760,570, 11/762, 526, 11/769,327, 11/769,255, 11/943,801 or 12/362,774. Plants comprising other genes that confer glyphosate tolerance, such as decarboxylase genes, are described in e.g. U.S. patent application Ser. Nos. 11/588,811, 11/185,342, 12/364, 724, 11/185,560 or 12/423,926.

Other herbicide resistant plants are for example plants that have been made tolerant to herbicides inhibiting the enzyme glutamine synthase, such as bialaphos, phosphinothricin or glufosinate. Such plants can be obtained by expressing an enzyme detoxifying the herbicide or a mutant glutamine synthase enzyme that is resistant to inhibition, e.g. described in U.S. patent application Ser. No. 11/760,602. One such efficient detoxifying enzyme is an enzyme encoding a phosphinothricin acetyltransferase (such as the bar or pat protein from *Streptomyces* species). Plants expressing an exogenous phosphinothricin acetyltransferase are for example described in U.S. Pat. Nos. 5,561,236; 5,648,477; 5,646,024; 5,273, 894; 5,637,489; 5,276,268; 5,739,082; 5,908,810 and 7,112, 665.

Further herbicide-tolerant plants are also plants that have been made tolerant to the herbicides inhibiting the enzyme hydroxyphenylpyruvatedioxygenase (HPPD). HPPD is an enzyme that catalyzes the reaction in which para-hydroxyphenylpyruvate (HPP) is transformed into homogentisate. Plants tolerant to HPPD-inhibitors can be transformed with a gene encoding a naturally-occurring resistant HPPD enzyme, or a gene encoding a mutated or chimeric HPPD enzyme as described in WO 96/38567, WO 99/24585 and WO 99/24586. Tolerance to HPPD-inhibitors can also be obtained by transforming plants with genes encoding certain enzymes enabling the formation of homogentisate despite the inhibition of the native HPPD enzyme by the HPPD-inhibitor. Such plants and genes are described in WO 99/34008 and WO 02/36787. Tolerance of plants to HPPD inhibitors can also be improved by transforming plants with a gene encoding an enzyme having prephenate dehydrogenase (PDH) activity in addition to a gene encoding an HPPD-tolerant enzyme, as described in WO 2004/024928. Further, plants can be made more tolerant to HPPD-inhibitor herbicides by adding into their genome a gene encoding an enzyme capable of metabolizing or degrading HPPD inhibitors, such as the CYP450 enzymes shown in WO 2007/103567 and WO 2008/150473.

Still further herbicide resistant plants are plants that have been made tolerant to acetolactate synthase (ALS) inhibitors. Known ALS-inhibitors include, for example, sulfonylurea, imidazolinone, triazolopyrimidines, pryimidinyoxy(thio) benzoates, and/or sulfonylaminocarbonyltriazolinone herbicides. Different mutations in the ALS enzyme (also known as acetohydroxyacid synthase, AHAS) are known to confer tolerance to different herbicides and groups of herbicides, as described for example in Tranel and Wright (2002, Weed Science 50:700-712), but also, in U.S. Pat. Nos. 5,605,011, 5,378,824, 5,141,870, and 5,013,659. The production of sulfonylurea-tolerant plants and imidazolinone-tolerant plants is described in U.S. Pat. Nos. 5,605,011; 5,013,659; 5,141,870; 5,767,361; 5,731,180; 5,304,732; 4,761,373; 5,331,107;

5,928,937; and 5,378,824; and international publication WO 96/33270. Other imidazolinone-tolerant plants are also described in for example WO 2004/040012, WO 2004/106529, WO 2005/020673, WO 2005/093093, WO 2006/007373, WO 2006/015376, WO 2006/024351, and WO 2006/060634. Further sulfonylurea- and imidazolinone-tolerant plants are also described in for example WO 07/024,782 and U.S. Patent Application No. 61/288,958.

Other plants tolerant to imidazolinone and/or sulfonylurea can be obtained by induced mutagenesis, selection in cell cultures in the presence of the herbicide or mutation breeding as described for example for soybeans in U.S. Pat. No. 5,084,082, for rice in WO 97/41218, for sugar beet in U.S. Pat. No. 5,773,702 and WO 99/057965, for lettuce in U.S. Pat. No. 5,198,599, or for sunflower in WO 01/065922.

Plants or plant cultivars (obtained by plant biotechnology methods such as genetic engineering) which may also be treated according to the invention are insect-resistant transgenic plants, i.e. plants made resistant to attack by certain target insects. Such plants can be obtained by genetic transformation, or by selection of plants containing a mutation imparting such insect resistance.

An "insect-resistant transgenic plant", as used herein, includes any plant containing at least one transgene comprising a coding sequence encoding:

1) an insecticidal crystal protein from *Bacillus thuringiensis* or an insecticidal portion thereof, such as the insecticidal crystal proteins listed by Crickmore et al. (1998, Microbiology and Molecular Biology Reviews, 62: 807-813), updated by Crickmore et al. (2005) at the *Bacillus thuringiensis* toxin nomenclature, online at: http://www.lifesci.sussex.ac.uk/Home/Neil_Crickmore/Bt/), or insecticidal portions thereof, e.g., proteins of the Cry protein classes Cry1Ab, Cry1Ac, Cry1B, Cry1C, Cry1D, Cry1F, Cry2Ab, Cry3Aa, or Cry3Bb or insecticidal portions thereof (e.g. EP 1999141 and WO 2007/107302), or such proteins encoded by synthetic genes as e.g. described in U.S. patent application Ser. No. 12/249,016; or 2) a crystal protein from *Bacillus thuringiensis* or a portion thereof which is insecticidal in the presence of a second other crystal protein from *Bacillus thuringiensis* or a portion thereof, such as the binary toxin made up of the Cry34 and Cry35 crystal proteins (Moellenbeck et al. 2001, Nat. Biotechnol. 19: 668-72; Schnepf et al. 2006, Applied Environm. Microbiol. 71, 1765-1774) or the binary toxin made up of the Cry1A or Cry1F proteins and the Cry2Aa or Cry2Ab or Cry2Ae proteins (U.S. patent application Ser. No. 12/214,022 and EP 08010791.5); or 3) a hybrid insecticidal protein comprising parts of two different insecticidal crystal proteins from *Bacillus thuringiensis*, such as a hybrid of the proteins of 1) above or a hybrid of the proteins of 2) above, e.g., the Cry1A.105 protein produced by corn event MON89034 (WO 2007/027777); or 4) a protein of any one of 1) to 3) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation, such as the Cry3Bb1 protein in corn events MON863 or MON88017, or the Cry3A protein in corn event MIR604; or 5) an insecticidal secreted protein from *Bacillus thuringiensis* or *Bacillus cereus*, or an insecticidal portion thereof, such as the vegetative insecticidal (VIP) proteins listed at: http://www.lifesci.sussex.ac.uk/home/Neil_Crickmore/Bt/vip.html, e.g., proteins from the VIP3Aa protein class; or 6) a secreted protein from *Bacillus thuringiensis* or *Bacillus cereus* which is insecticidal in the presence of a second secreted protein from *Bacillus thuringiensis* or *B. cereus*, such as the binary toxin made up of the VIP1A and VIP2A proteins (WO 94/21795); or 7) a hybrid insecticidal protein comprising parts from different secreted proteins from *Bacillus thuringiensis* or *Bacillus cereus*, such as a hybrid of the proteins in 1) above or a hybrid of the proteins in 2) above; or 8) a protein of any one of 5) to 7) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation (while still encoding an insecticidal protein), such as the VIP3Aa protein in cotton event COT102; or 9) a secreted protein from *Bacillus thuringiensis* or *Bacillus cereus* which is insecticidal in the presence of a crystal protein from *Bacillus thuringiensis*, such as the binary toxin made up of VIP3 and Cry1A or Cry1F (U.S. Patent Appl. No. 61/126,083 and 61/195,019), or the binary toxin made up of the VIP3 protein and the Cry2Aa or Cry2Ab or Cry2Ae proteins (U.S. patent application Ser. No. 12/214,022 and EP 08010791.5); or 10) a protein of 9) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation (while still encoding an insecticidal protein)

Of course, an insect-resistant transgenic plant, as used herein, also includes any plant comprising a combination of genes encoding the proteins of any one of the above classes 1 to 10. In one embodiment, an insect-resistant plant contains more than one transgene encoding a protein of any one of the above classes 1 to 10, to expand the range of target insect species affected when using different proteins directed at different target insect species, or to delay insect resistance development to the plants by using different proteins insecticidal to the same target insect species but having a different mode of action, such as binding to different receptor binding sites in the insect.

An "insect-resistant transgenic plant", as used herein, further includes any plant containing at least one transgene comprising a sequence producing upon expression a double-stranded RNA which upon ingestion by a plant insect pest inhibits the growth of this insect pest, as described e.g. in WO 2007/080126, WO 2006/129204, WO 2007/074405, WO 2007/080127 and WO 2007/035650.

Plants or plant cultivars (obtained by plant biotechnology methods such as genetic engineering) which may also be treated according to the invention are tolerant to abiotic stresses. Such plants can be obtained by genetic transformation, or by selection of plants containing a mutation imparting such stress resistance. Particularly useful stress tolerance plants include:

1) plants which contain a transgene capable of reducing the expression and/or the activity of poly(ADP-ribose) polymerase (PARP) gene in the plant cells or plants as described in WO 00/04173, WO/2006/045633, EP 04077984.5, or EP 06009836.5.
2) plants which contain a stress tolerance enhancing transgene capable of reducing the expression and/or the activity of the PARG encoding genes of the plants or plants cells, as described e.g. in WO 2004/090140.
3) plants which contain a stress tolerance enhancing transgene coding for a plant-functional enzyme of the nicotinamide adenine dinucleotide salvage biosynthesis pathway including nicotinamidase, nicotinate phosphoribosyltransferase, nicotinic acid mononucleotide adenyl transferase, nicotinamide adenine dinucleotide synthetase or nicotinamide phosphoribosyltransferase as described e.g. in EP 04077624.7, WO 2006/133827, PCT/EP07/002,433, EP 1999263, or WO 2007/107326.

Plants or plant cultivars (obtained by plant biotechnology methods such as genetic engineering) which may also be treated according to the invention show altered quantity, quality and/or storage-stability of the harvested product and/or altered properties of specific ingredients of the harvested product such as:

1) transgenic plants which synthesize a modified starch, which in its physical-chemical characteristics, in particular the amylose content or the amylose/amylopectin ratio, the degree of branching, the average chain length, the side chain distribution, the viscosity behaviour, the gelling strength, the starch grain size and/or the starch grain morphology, is changed in comparison with the synthesised starch in wild type plant cells or plants, so that this modified starch is better suited for special applications. Said transgenic plants synthesizing a modified starch are disclosed, for example, in EP 0571427, WO 95/04826, EP 0719338, WO 96/15248, WO 96/19581, WO 96/27674, WO 97/11188, WO 97/26362, WO 97/32985, WO 97/42328, WO 97/44472, WO 97/45545, WO 98/27212, WO 98/40503, WO99/58688, WO 99/58690, WO 99/58654, WO 00/08184, WO 00/08185, WO 00/08175, WO 00/28052, WO 00/77229, WO 01/12782, WO 01/12826, WO 02/101059, WO 03/071860, WO 2004/056999, WO 2005/030942, WO 2005/030941, WO 2005/095632, WO 2005/095617, WO 2005/095619, WO 2005/095618, WO 2005/123927, WO 2006/018319, WO 2006/103107, WO 2006/108702, WO 2007/009823, WO 00/22140, WO 2006/063862, WO 2006/072603, WO 02/034923, EP 06090134.5, EP 06090228.5, EP 06090227.7, EP 07090007.1, EP 07090009.7, WO 01/14569, WO 02/79410, WO 03/33540, WO 2004/078983, WO 01/19975, WO 95/26407, WO 96/34968, WO 98/20145, WO 99/12950, WO 99/66050, WO 99/53072, U.S. Pat. No. 6,734,341, WO 00/11192, WO 98/22604, WO 98/32326, WO 01/98509, WO 01/98509, WO 2005/002359, U.S. Pat. Nos. 5,824,790, 6,013,861, WO 94/04693, WO 94/09144, WO 94/11520, WO 95/35026, WO 97/20936
2) transgenic plants which synthesize non starch carbohydrate polymers or which synthesize non starch carbohydrate polymers with altered properties in comparison to wild type plants without genetic modification. Examples are plants producing polyfructose, especially of the inulin and levan type, as disclosed in EP 0663956, WO 96/01904, WO 96/21023, WO 98/39460, and WO 99/24593, plants producing alpha-1,4-glucans as disclosed in WO 95/31553, US 2002031826, U.S. Pat. Nos. 6,284,479, 5,712,107, WO 97/47806, WO 97/47807, WO 97/47808 and WO 00/14249, plants producing alpha-1,6 branched alpha-1,4-glucans, as disclosed in WO 00/73422, and plants producing alternan, as disclosed in e.g. WO 00/47727, WO 00/73422, EP 06077301.7, U.S. Pat. No. 5,908,975 and EP 0728213,
3) transgenic plants which produce hyaluronan, as for example disclosed in WO 2006/032538, WO 2007/039314, WO 2007/039315, WO 2007/039316, JP 2006304779, and WO 2005/012529.
4) transgenic plants or hybrid plants, such as onions with characteristics such as 'high soluble solids content', 'low pungency' (LP) and/or 'long storage' (LS), as described in U.S. patent application Ser. No. 12/020,360 and 61/054,026.

Plants or plant cultivars (obtained by plant biotechnology methods such as genetic engineering) which may also be treated according to the invention are plants, such as cotton plants, with altered fiber characteristics. Such plants can be obtained by genetic transformation, or by selection of plants containing a mutation imparting such altered fiber characteristics and include:

a) Plants, such as cotton plants, containing an altered form of cellulose synthase genes as described in WO 98/00549
b) Plants, such as cotton plants, containing an altered form of rsw2 or rsw3 homologous nucleic acids as described in WO 2004/053219
c) Plants, such as cotton plants, with increased expression of sucrose phosphate synthase as described in WO 01/17333
d) Plants, such as cotton plants, with increased expression of sucrose synthase as described in WO 02/45485
e) Plants, such as cotton plants, wherein the timing of the plasmodesmatal gating at the basis of the fiber cell is altered, e.g. through downregulation of fiber-selective β-1,3-glucanase as described in WO 2005/017157, or as described in EP 08075514.3 or U.S. Patent Appl. No. 61/128,938
f) Plants, such as cotton plants, having fibers with altered reactivity, e.g. through the expression of N-acetylglucosaminetransferase gene including nodC and chitin synthase genes as described in WO 2006/136351

Plants or plant cultivars (obtained by plant biotechnology methods such as genetic engineering) which may also be treated according to the invention are plants, such as oilseed rape or related *Brassica* plants, with altered oil profile characteristics. Such plants can be obtained by genetic transformation, or by selection of plants containing a mutation imparting such altered oil profile characteristics and include:

a) Plants, such as oilseed rape plants, producing oil having a high oleic acid content as described e.g. in U.S. Pat. Nos. 5,969,169, 5,840,946 or 6,323,392 or 6,063,947
b) Plants such as oilseed rape plants, producing oil having a low linolenic acid content as described in U.S. Pat. Nos. 6,270,828, 6,169,190, or 5,965,755
c) Plant such as oilseed rape plants, producing oil having a low level of saturated fatty acids as described e.g. in U.S. Pat. No. 5,434,283 or U.S. patent application Ser. No. 12/668,303

Plants or plant cultivars (obtained by plant biotechnology methods such as genetic engineering) which may also be treated according to the invention are plants, such as oilseed rape or related *Brassica* plants, with altered seed scattering characteristics. Such plants can be obtained by genetic transformation, or by selection of plants containing a mutation imparting such altered seed scattering characteristics and include plants such as oilseed rape plants with delayed or reduced seed scattering as described in U.S. Patent Appl. No. 61/135,230, WO09/068,313 and WO10/006,732.

Particularly useful transgenic plants which may be treated according to the invention are plants containing transformation events, or combination of transformation events, that are the subject of petitions for non-regulated status, in the United States of America, to the Animal and Plant Health Inspection Service (APHIS) of the United States Department of Agriculture (USDA) whether such petitions are granted or are still pending. At any time this information is readily available from APHIS (4700 River Road Riverdale, Md. 20737, USA), for instance on its internet site (URL http://www.aphis.usda.gov/brs/not_reg.html). On the filing date of this application the petitions for nonregulated status that were pending with APHIS or granted by APHIS were those listed in table B which contains the following information:

Petition: the identification number of the petition. Technical descriptions of the transformation events can be found in the individual petition documents which are obtainable from APHIS, for example on the APHIS website, by reference to this petition number. These descriptions are herein incorporated by reference.

Extension of Petition: reference to a previous petition for which an extension is requested.

Institution: the name of the entity submitting the petition.

Regulated article: the plant species concerned.

Transgenic phenotype: the trait conferred to the plants by the transformation event.

Transformation event or line: the name of the event or events (sometimes also designated as lines or lines) for which nonregulated status is requested.

APHIS documents: various documents published by APHIS in relation to the Petition and which can be requested with APHIS.

Additional particularly useful plants containing single transformation events or combinations of transformation events are listed for example in the databases from various national or regional regulatory agencies (see for example http://gmoinfo.jrc.it/gmp_browse.aspx and http://cera-gm-c.org/index.php?evidcode=&hstIDXCode=&gType=&AbbrCode=&atCode=&stCode=&coIDCode=&action=gm_crop_database&mode=Submit).

Further particular transgenic plants include plants containing a transgene in an agronomically neutral or beneficial position as described in any of the patent publications listed in Table C.

In a particularly preferred variant, the process according to the invention is used for the treatment of transgenic vegetable, cotton and soybean cultivars.

TABLE A

Nonexhaustive list of transgenic plants and events for reworking the invention. Source: (AGBIOS, P.O. Box 475, 106 St. John St. Merrickville, Ontario K0G1N0, CANADA) database accessible at: http://www.agbios.com/dbase.php.

| No. | Transgenic event | Company | Description | Crop plant |
|---|---|---|---|---|
| A-1 | ASR368 | Scotts Seeds | Glyphosate tolerance derived by inserting a modified 5-enolpyruvylshikimate-3-phosphate synthase (EPSPS) encoding gene from *Agrobacterium tumefaciens*, parent line B99061 | *Agrostis stolonifera* Creeping Bentgrass |
| A-2 | Asr-368 | | Glyphosate tolerance; US 2006-162007 | Bent Grass |
| A-3 | H7-1 | Monsanto Company | Glyphosate herbicide tolerant sugar beet produced by inserting a gene encoding the enzyme 5-enolpyruvylshikimate-3-phosphate synthase (EPSPS) from the CP4 strain of *Agrobacterium tumefaciens*; WO 2004-074492 | *Beta vulgaris* |
| A-4 | T120-7 | Bayer CropScience (Aventis CropScience(AgrEvo)) | Introduction of the PPT-acetyltransferase (PAT) encoding gene from *Streptomyces viridochromogenes*, an aerobic soil bacterium. PPT normally acts to inhibit glutamine synthetase, causing a fatal accumulation of ammonia. Acetylated PPT is inactive. | *Beta vulgaris* |
| A-5 | GTSB77 | Novartis Seeds; Monsanto Company | Glyphosate herbicide tolerant sugar beet produced by inserting a gene encoding the enzyme 5-enolpyruvylshikimate-3-phosphate synthase (EPSPS) from the CP4 strain of *Agrobacterium tumefaciens*. | *Beta vulgaris* (sugar beet) |
| A-6 | T227-1 | | Glyphosate tolerance; US 2004-117870 | *Beta vulgaris* sugar beet |
| A-7 | 23-18-17, 23-198 | Monsanto Company (formerly Calgene) | High lauric acid (12:0) and myristic acid (14:0) canola produced by inserting a thioesterase encoding gene from the California bay laurel (*Umbellularia californica*). | *Brassica napus* (Argentine Canola) |
| A-8 | 45A37, 46A40 | Pioneer Hi-Bred International Inc. | High oleic acid and low linolenic acid canola produced through a combination of chemical mutagenesis to select for a fatty acid desaturase mutant with elevated oleic acid, and traditional back-crossing to introduce the low linolenic acid trait. | *Brassica napus* (Argentine Canola) |
| A-9 | 46A12, 46A16 | Pioneer Hi-Bred International Inc. | Combination of chemical mutagenesis, to achieve the high oleic acid trait, and traditional breeding with registered canola varieties. | *Brassica napus* (Argentine Canola) |

TABLE A-continued

Nonexhaustive list of transgenic plants and events for reworking the invention. Source: (AGBIOS, P.O. Box 475, 106 St. John St. Merrickville, Ontario K0G1N0, CANADA) database accessible at: http://www.agbios.com/dbase.php.

| No. | Transgenic event | Company | Description | Crop plant |
|---|---|---|---|---|
| A-10 | GT200 | Monsanto Company | Glyphosate herbicide tolerant canola produced by inserting genes encoding the enzymes 5-enolpyruvylshikimate-3-phosphate synthase (EPSPS) from the CP4 strain of *Agrobacterium tumefaciens* and glyphosate oxidase from *Ochrobactram anthropi*. | *Brassica napus* (Argentine Canola) |
| A-11 | GT73, RT73 | Monsanto Company | Glyphosate herbicide tolerant canola produced by inserting genes encoding the enzymes 5-enolpyruvylshikimate-3-phosphate synthase (EPSPS) from the CP4 strain of *Agrobacterium tumefaciens* and glyphosate oxidase from *Ochrobactram anthropi*. | *Brassica napus* (Argentine Canola) |
| A-12 | HCN10 | Aventis CropScience | Introduction of the PPT-acetyltransferase (PAT) encoding gene from *Streptomyces viridochromogenes*, an aerobic soil bacterium. PPT normally acts to inhibit glutamine synthetase, causing a fatal accumulation of ammonia. Acetylated PPT is inactive. | *Brassica napus* (Argentine Canola) |
| A-13 | HCN92 | Bayer CropScience (Aventis CropScience(AgrEvo)) | Introduction of the PPT-acetyltransferase (PAT) encoding gene from *Streptomyces viridochromogenes*, an aerobic soil bacterium. PPT normally acts to inhibit glutamine synthetase, causing a fatal accumulation of ammonia. Acetylated PPT is inactive. | *Brassica napus* (Argentine Canola) |
| A-14 | MS1, RF1 => PGS1 | Aventis CropScience (formerly Plant Genetic Systems) | Male-sterility, fertility restoration, pollination control system displaying glufosinate herbicide tolerance. MS lines contained the barnase gene from *Bacillus amyloliquefaciens*, RF lines contained the barstar gene from the same bacterium, and both lines contained the phosphinothricin N-acetyltransferase (PAT) encoding gene from *Streptomyces hygroscopicus*. | *Brassica napus* (Argentine Canola) |
| A-15 | MS1, RF2 => PGS2 | Aventis CropScience (formerly Plant Genetic Systems) | Male-sterility, fertility restoration, pollination control system displaying glufosinate herbicide tolerance. MS lines contained the barnase gene from *Bacillus amyloliquefaciens*, RF lines contained the barstar gene from the same bacterium, and both lines contained the phosphinothricin N-acetyltransferase (PAT) encoding gene from *Streptomyces hygroscopicus*. | *Brassica napus* (Argentine Canola) |
| A-16 | MS8xRF3 | Bayer CropScience (Aventis CropScience(AgrEvo)) | Male-sterility, fertility restoration, pollination control system displaying glufosinate herbicide tolerance. MS lines contained the barnase gene from *Bacillus amyloliquefaciens*, RF lines contained the barstar gene from the same bacterium, and both lines contained the phosphinothricin N-acetyltransferase (PAT) encoding gene from *Streptomyces hygroscopicus*. | *Brassica napus* (Argentine Canola) |
| A-17 | MS-B2 | | Male sterility; WO 01/31042 | *Brassica napus* (Argentine Canola) |
| A-18 | MS-BN1/RF-BN1 | | Male sterility/restoration; WO 01/41558 | *Brassica napus* (Argentine Canola) |
| A-19 | NS738, NS1471, NS1473 | Pioneer Hi-Bred International Inc. | Selection of somaclonal variants with altered acetolactate synthase (ALS) enzymes, following chemical mutagenesis. Two lines (P1, P2) were initially selected with modifications at different unlinked loci. NS738 contains the P2 mutation only. | *Brassica napus* (Argentine Canola) |
| A-20 | OXY-235 | Aventis CropScience (formerly Rhône Poulenc Inc.) | Tolerance to the herbicides bromoxynil and ioxynil by incorporation of the nitrilase gene from *Klebsiella pneumoniae*. | *Brassica napus* (Argentine Canola) |
| A-21 | PHY14, PHY35 | Aventis CropScience (formerly Plant Genetic Systems) | Male sterility was produced via insertion of the barnase ribonuclease gene from *Bacillus amyloliquefaciens*; fertility restoration by insertion of the barstar RNase inhibitor; PPT | *Brassica napus* (Argentine Canola) |

TABLE A-continued

Nonexhaustive list of transgenic plants and events for reworking the invention. Source: (AGBIOS, P.O. Box 475, 106 St. John St. Merrickville, Ontario K0G1N0, CANADA) database accessible at: http://www.agbios.com/dbase.php.

| No. | Transgenic event | Company | Description | Crop plant |
|---|---|---|---|---|
| A-22 | PHY36 | Aventis CropScience (formerly Plant Genetic Systems) | resistance was via PPT-acetyltransferase (PAT) from *Streptomyces hygroscopicus*. Male sterility was produced via insertion of the barnase ribonuclease gene from *Bacillus amyloliquefaciens*; fertility restoration by insertion of the barstar RNase inhibitor; PPT resistance was via PPT-acetyltransferase (PAT) from *Streptomyces hygroscopicus*. | *Brassica napus* (Argentine Canola) |
| A-23 | RT73 | | Glyphosate resistance; WO 02/36831 | *Brassica napus* (Argentine Canola) |
| A-24 | T45 (HCN28) | Bayer CropScience (Aventis CropScience(AgrEvo)) | Introduction of the PPT-acetyltransferase (PAT) encoding gene from *Streptomyces viridochromogenes*, an aerobic soil bacterium. PPT normally acts to inhibit glutamine synthetase, causing a fatal accumulation of ammonia. Acetylated PPT is inactive. | *Brassica napus* (Argentine Canola) |
| A-25 | HCR-1 | Bayer CropScience (Aventis CropScience(AgrEvo)) | Introduction of the glufosinate ammonium herbicide tolerance trait from transgenic *B. napus* line T45. This trait is mediated by the phosphinothricin acetyltransferase (PAT) encoding gene from *S. viridochromogenes*. | *Brassica rapa* (Polish Canola) |
| A-26 | ZSR500/502 | Monsanto Company | Introduction of a modified 5-enol-pyruvylshikimate-3-phosphate synthase (EPSPS) and a gene from *Achromobacter* sp that degrades glyphosate by conversion to aminomethylphosphonic acid (AMPA) and glyoxylate by interspecific crossing with GT73. | *Brassica rapa* (Polish Canola) |
| A-27 | EE-1 | | Insect resistance (Cry1Ac); WO 2007/091277 | Brinjal |
| A-28 | 55-1/63-1 | Cornell University | Papaya ringspot virus (PRSV) resistant papaya produced by inserting the coat protein (CP) encoding sequences from this plant potyvirus. | *Carica papaya* (Papaya) |
| A-29 | RM3-3, RM3-4, RM3-6 | Bejo Zaden BV | Male sterility was produced via insertion of the barnase ribonuclease gene from *Bacillus amyloliquefaciens*; PPT resistance was via the bar gene from *S. hygroscopicus*, which encodes the PAT enzyme. | *Cichorium intybus* (Chicory) |
| A-30 | A, B | Agritope Inc. | Reduced accumulation of S-adenosylmethionine (SAM), and consequently reduced ethylene synthesis, by introduction of the gene encoding S-adenosylmethionine hydrolase. | *Cucumis melo* (Melon) |
| A-31 | CZW-3 | Asgrow (USA); Seminis Vegetable Inc. (Canada) | Cucumber mosaic virus (CMV), zucchini yellows mosaic virus (ZYMV) and watermelon mosaic virus (WMV) 2 resistant squash (*Curcurbita pepo*) produced by inserting the coat protein (CP) encoding sequences from each of these plant viruses into the host genome. | *Cucurbita pepo* (Squash) |
| A-32 | ZW20 | Upjohn (USA); Seminis Vegetable Inc. (Canada) | Zucchini yellows mosaic virus (ZYMV) and watermelon mosaic virus (WMV) 2 resistant squash (*Curcurbita pepo*) produced by inserting the coat protein (CP) encoding sequences from each of these plant potyviruses into the host genome. | *Cucurbita pepo* (Squash) |
| A-33 | 66 | Florigene Pty Ltd. | Delayed senescence and sulfonylurea herbicide tolerant carnations produced by inserting a truncated copy of the carnation aminocyclopropane cyclase (ACC) synthase encoding gene in order to suppress expression of the endogenous unmodified gene, which is required for normal ethylene biosynthesis. Tolerance to sulfonyl urea herbicides was via the introduction of a chlorsulfuron tolerant version of the acetolactate synthase (ALS) encoding gene from tobacco. | *Dianthus caryophyllus* (Carnation) |
| A-34 | 4, 11, 15, 16 | Florigene Pty Ltd. | Modified colour and sulfonylurea herbicide tolerant carnations produced by inserting two anthocyanin biosynthetic genes whose | *Dianthus caryophyllus* (Carnation) |

TABLE A-continued

Nonexhaustive list of transgenic plants and events for reworking the invention. Source: (AGBIOS, P.O. Box 475, 106 St. John St. Merrickville, Ontario K0G1N0, CANADA) database accessible at: http://www.agbios.com/dbase.php.

| No. | Transgenic event | Company | Description | Crop plant |
|---|---|---|---|---|
| | | | expression results in a violet/mauve colouration. Tolerance to sulfonyl urea herbicides was via the introduction of a chlorsulfuron tolerant version of the acetolactate synthase (ALS) encoding gene from tobacco. | |
| A-35 | 959A, 988A, 1226A, 1351A, 1363A, 1400A | Florigene Pty Ltd. | Introduction of two anthocyanin biosynthetic genes to result in a violet/mauve colouration; Introduction of a variant form of acetolactate synthase (ALS). | *Dianthus caryophyllus* (Carnation) |
| A-36 | 3560.4.3.5 | | Glyphosate/ALS inhibitor-tolerance; WO 2008002872 | *Glycine max* L. (Soybean) |
| A-37 | A2704-12 | | Glufosinate tolerance; WO 2006/108674 | *Glycine max* L. (Soybean) |
| A-38 | A2704-12, A2704-21, A5547-35 | Aventis CropScience | Glufosinate ammonium herbicide tolerant soybean produced by inserting a modified phosphinothricin acetyltransferase (PAT) encoding gene from the soil bacterium *Streptomyces viridochromogenes*. | *Glycine max* L. (Soybean) |
| A-39 | A5547-127 | Bayer CropScience (Aventis CropScience(AgrEvo)) | Glufosinate ammonium herbicide tolerant soybean produced by inserting a modified phosphinothricin acetyltransferase (PAT) encoding gene from the soil bacterium *Streptomyces viridochromogenes*. | *Glycine max* L. (Soybean) |
| A-40 | A5547-35 | | Glufosinate tolerance; WO 2006/108675 | *Glycine max* L. (Soybean) |
| A-41 | DP-305423-1 | | High oleic acid/ALS inhibitor tolerance; WO 2008/054747 | *Glycine max* L. (Soybean) |
| A-42 | DP356043 | Pioneer Hi-Bred International Inc. | Soybean event with two herbicide tolerance genes: glyphosate N-acetyltransferase, which detoxifies glyphosate, and a modified acetolactate synthase (A | *Glycine max* L. (Soybean) |
| A-43 | G94-1, G94-19, G168 | DuPont Canada Agricultural Products | High oleic acid soybean produced by inserting a second copy of the fatty acid desaturase (GmFad2-1) encoding gene from soybean, which resulted in "silencing" of the endogenous host gene. | *Glycine max* L. (Soybean) |
| A-44 | GTS 40-3-2 | Monsanto Company | Glyphosate tolerant soybean variety produced by inserting a modified 5-enolpyruvylshikimate-3-phosphate synthase (EPSPS) encoding gene from the soil bacterium *Agrobacterium tumefaciens*. | *Glycine max* L. (Soybean) |
| A-45 | GU262 | Bayer CropScience (Aventis CropScience(AgrEvo)) | Glufosinate ammonium herbicide tolerant soybean produced by inserting a modified phosphinothricin acetyltransferase (PAT) encoding gene from the soil bacterium *Streptomyces viridochromogenes*. | *Glycine max* L. (Soybean) |
| A-46 | MON87701 | | insect resistance (Cry1ac); WO 2009064652 | *Glycine max* L. (Soybean) |
| A-47 | MON87705 | | altered fatty acid levels (mid-oleic and low saturate); WO 2010037016 | *Glycine max* L. (Soybean) |
| A-48 | MON87754 | | increased oil content; WO 2010024976 | *Glycine max* L. (Soybean) |
| A-49 | MON87769 | | stearidonic acid (SDA) comprising oil; WO 2009102873 | *Glycine max* L. (Soybean) |
| A-50 | MON89788 | Monsanto Company | Glyphosate-tolerant soybean produced by inserting a modified 5-enolpyruvylshikimate-3-phosphate synthase (EPSPS) encoding aroA (epsps) gene from *Agrobacterium tumefaciens* CP4; WO2006130436 | *Glycine max* L. (Soybean) |
| A-51 | OT96-15 | Agriculture & Agri-Food Canada | Low linolenic acid soybean produced through traditional cross-breeding to incorporate the novel trait from a naturally occurring fan1 gene mutant that was selected for low linolenic acid. | *Glycine max* L. (Soybean) |
| A-52 | W62, W98 | Bayer CropScience (Aventis CropScience(AgrEvo)) | Glufosinate ammonium herbicide tolerant soybean produced by inserting a modified phosphinothricin acetyltransferase (PAT) encoding gene from the soil bacterium *Streptomyces hygroscopicus*. | *Glycine max* L. (Soybean) |
| A-53 | 15985 | Monsanto Company | Insect resistant cotton derived by transformation of the DP50B parent variety, which contained event 531 (expressing | *Gossypium hirsutum* L. (Cotton) |

TABLE A-continued

Nonexhaustive list of transgenic plants and events for reworking the invention. Source: (AGBIOS, P.O. Box 475, 106 St. John St. Merrickville, Ontario K0G1N0, CANADA) database accessible at: http://www.agbios.com/dbase.php.

| No. | Transgenic event | Company | Description | Crop plant |
|---|---|---|---|---|
| | | | Cry1Ac protein), with purified plasmid DNA containing the cry2Ab gene from *B. thuringiensis* subsp. *kurstaki*. | |
| A-54 | 1143-14A | | Insect resistance (Cry1Ab); WO 2006/128569 | *Gossypium hirsutum* L. (Cotton) |
| A-55 | 1143-51B | | Insect resistance (Cry1Ab); WO 2006/128570 | *Gossypium hirsutum* L. (Cotton) |
| A-56 | 19-51A | DuPont Canada Agricultural Products | Introduction of a variant form of acetolactate synthase (ALS). | *Gossypium hirsutum* L. (Cotton) |
| A-57 | 281-24-236 | DOW AgroSciences LLC | Insect-resistant cotton produced by inserting the cry1F gene from *Bacillus thuringiensis* var. *aizawai*. The PAT encoding gene from *Streptomyces viridochromogenes* was introduced as a selectable marker. | *Gossypium hirsutum* L. (Cotton) |
| A-58 | 3006-210-23 | DOW AgroSciences LLC | Insect-resistant cotton produced by inserting the cry1Ac gene from *Bacillus thuringiensis* subsp. *kurstaki*. The PAT encoding gene from *Streptomyces viridochromogenes* was introduced as a selectable marker. | *Gossypium hirsutum* L. (Cotton) |
| A-59 | 31807/31808 | Calgene Inc. | Insect-resistant and bromoxynil herbicide tolerant cotton produced by inserting the cry1Ac gene from *Bacillus thuringiensis* and a nitrilase encoding gene from *Klebsiella pneumoniae*. | *Gossypium hirsutum* L. (Cotton) |
| A-60 | BXN | Calgene Inc. | Bromoxynil herbicide tolerant cotton produced by inserting a nitrilase encoding gene from *Klebsiella pneumoniae*. | *Gossypium hirsutum* L. (Cotton) |
| A-61 | CE43-67B | | Insect resistance (Cry1Ab); WO 2006/128573 | *Gossypium hirsutum* L. (Cotton) |
| A-62 | CE44-69D | | Insect resistance (Cry1Ab); WO 2006/128571 | *Gossypium hirsutum* L. (Cotton) |
| A-63 | CE46-02A | | Insect resistance (Cry1Ab); WO 2006/128572 | *Gossypium hirsutum* L. (Cotton) |
| A-64 | Cot102 | | Insect resistance (Vip3A); US 2006-130175 | *Gossypium hirsutum* L. (Cotton) |
| A-65 | COT102 | Syngenta Seeds, Inc. | Insect-resistant cotton produced by inserting the vip3A(a) gene from *Bacillus thuringiensis* AB88. The APH4 encoding gene from *E. coli* was introduced as a selectable marker. | *Gossypium hirsutum* L. (Cotton) |
| A-66 | COT202 | | Insect resistance (VIP3A); US2009181399 | *Gossypium hirsutum* L. (Cotton) |
| A-67 | Cot202 | | Insect resistance (VIP3); US 2007-067868 | *Gossypium hirsutum* L. (Cotton) |
| A-68 | DAS-21Ø23-5 × DAS-24236-5 | DOW AgroSciences LLC | WideStrike ™, a stacked insect-resistant cotton derived from conventional cross-breeding of parental lines 3006-210-23 (OECD identifier: DAS-21Ø23-5) and 281-24-236 (OECD identifier: DAS-24236-5). | *Gossypium hirsutum* L. (Cotton) |
| A-69 | DAS-21Ø23-5 × DAS-24236-5 × MON88913 | DOW AgroSciences LLC and Pioneer Hi-Bred International Inc. | Stacked insect-resistant and glyphosate-tolerant cotton derived from conventional cross-breeding of WideStrike cotton (OECD identifier: DAS-21Ø23-5 × DAS-24236-5) with MON88913, known as RoundupReady Flex (OECD identifier: MON-88913-8). | *Gossypium hirsutum* L. (Cotton) |
| A-70 | DAS-21Ø23-5 × DAS-24236-5 × MON-Ø1445-2 | DOW AgroSciences LLC | WideStrike ™/Roundup Ready ® cotton, a stacked insect-resistant and glyphosate-tolerant cotton derived from conventional cross-breeding of WideStrike cotton (OECD identifier: DAS-21Ø23-5 × DAS-24236-5) with MON1445 (OECD identifier: MON-Ø1445-2). | *Gossypium hirsutum* L. (Cotton) |
| A-71 | EE-GH3 | | Glyphosate tolerance; WO 2007/017186 | *Gossypium hirsutum* L. (Cotton) |

TABLE A-continued

Nonexhaustive list of transgenic plants and events for reworking the invention. Source: (AGBIOS, P.O. Box 475, 106 St. John St. Merrickville, Ontario K0G1N0, CANADA) database accessible at: http://www.agbios.com/dbase.php.

| No. | Transgenic event | Company | Description | Crop plant |
|---|---|---|---|---|
| A-72 | EE-GH5 | | Insect resistance (Cry1Ab); WO 2008/122406 | Gossypium hirsutum L. (Cotton) |
| A-73 | EE-GH6 | | Insect resistance (cry2Ae); WO2008151780 | Gossypium hirsutum L. (Cotton) |
| A-74 | event 281-24-236 | | Insect resistance (Cry1F); WO 2005/103266 | Gossypium hirsutum L. (Cotton) |
| A-75 | event3006-210-23 | | Insect resistance (Cry1Ac); WO 2005/103266 | Gossypium hirsutum L. (Cotton) |
| A-76 | GBH614 | Bayer CropScience (Aventis CropScience(AgrEvo)) | Glyphosate herbicide tolerant cotton produced by inserting 2MEPSPS gene into variety Coker312 by Agrobacterium under the control of Ph4a748At and TPotpC | Gossypium hirsutum L. (Cotton) |
| A-77 | LLCotton25 | Bayer CropScience (Aventis CropScience(AgrEvo)) | Glufosinate ammonium herbicide tolerant cotton produced by inserting a modified phosphinothricin acetyltransferase (PAT) encoding gene from the soil bacterium Streptomyces hygroscopicus; WO 2003013224 | Gossypium hirsutum L. (Cotton) |
| A-78 | LLCotton25 × MON15985 | Bayer CropScience (Aventis CropScience(AgrEvo)) | Stacked herbicide tolerant and insect resistant cotton combining tolerance to glufosinate ammonium herbicide from LLCotton25 (OECD identifier: ACS-GHØØ1-3) with resistance to insects from MON15985 (OECD identifier: MON-15985-7) | Gossypium hirsutum L. (Cotton) |
| A-79 | MON 15985 | | Insect resistance (Cry1A/Cry2Ab); US 2004-250317 | Gossypium hirsutum L. (Cotton) |
| A-80 | MON1445/1698 | Monsanto Company | Glyphosate herbicide tolerant cotton produced by inserting a naturally glyphosate tolerant form of the enzyme 5-enolpyruvyl shikimate-3-phosphate synthase (EPSPS) from A. tumefaciens strain CP4. | Gossypium hirsutum L. (Cotton) |
| A-81 | MON15985 × MON88913 | Monsanto Company | Stacked insect resistant and glyphosate tolerant cotton produced by conventional cross-breeding of the parental lines MON88913 (OECD identifier: MON-88913-8) and 15985 (OECD identifier: MON-15985-7). Glyphosate tolerance is derived from the line MON88913 which contains two genes encoding the enzyme 5-enolpyruvylshikimate-3-phosphate synthase (EPSPS) from the CP4 strain of Agrobacterium tumefaciens. Insect resistance is derived from the line MON15985 which was produced by transformation of the DP50B parent variety, which contained event 531 (expressing Cry1Ac protein), with purified plasmid DNA containing the cry2Ab gene from B. thuringiensis subsp. kurstaki. | Gossypium hirsutum L. (Cotton) |
| A-82 | MON-15985-7 × MON-Ø1445-2 | Monsanto Company | Stacked insect resistant and herbicide tolerant cotton derived from conventional cross-breeding of the parental lines 15985 (OECD identifier: MON-15985-7) and MON-1445 (OECD identifier: MON-Ø1445-2). | Gossypium hirsutum L. (Cotton) |
| A-83 | MON531/757/1076 | Monsanto Company | Insect-resistant cotton produced by inserting the cry1Ac gene from Bacillus thuringiensis subsp. kurstaki HD-73 (B.t.k.). | Gossypium hirsutum L. (Cotton) |
| A-84 | MON88913 | Monsanto Company | Glyphosate herbicide tolerant cotton produced by inserting two genes encoding the enzyme 5-enolpyruvylshikimate-3-phosphate synthase (EPSPS) from the CP4 strain of Agrobacterium tumefaciens; WO 2004/072235 | Gossypium hirsutum L. (Cotton) |

TABLE A-continued

Nonexhaustive list of transgenic plants and events for reworking the invention. Source: (AGBIOS, P.O. Box 475, 106 St. John St. Merrickville, Ontario K0G1N0, CANADA) database accessible at: http://www.agbios.com/dbase.php.

| No. | Transgenic event | Company | Description | Crop plant |
|---|---|---|---|---|
| A-85 | MON-ØØ531-6 × MON-Ø1445-2 | Monsanto Company | Stacked insect resistant and herbicide tolerant cotton derived from conventional cross-breeding of the parental lines MON531 (OECD identifier: MON-ØØ531-6) and MON-1445 (OECD identifier: MON-Ø1445-2). | Gossypium hirsutum L. (Cotton) |
| A-86 | PV-GHGT07 (1445) | | Glyphosate tolerance; US 2004-148666 | Gossypium hirsutum L. (Cotton) |
| A-87 | T304-40 | | Insect-resistance (Cry1Ab); WO2008/122406 | Gossypium hirsutum L. (Cotton) |
| A-88 | T342-142 | | Insect resistance (Cry1Ab); WO 2006/128568 | Gossypium hirsutum L. (Cotton) |
| A-89 | X81359 | BASF Inc. | Tolerance to imidazolinone herbicides by selection of a naturally occurring mutant. | Helianthus annuus (Sunflower) |
| A-90 | RH44 | BASF Inc. | Selection for a mutagenized version of the enzyme acetohydroxyacid synthase (AHAS), also known as acetolactate synthase (ALS) or acetolactate pyruvate-lyase. | Lens culinaris (Lentil) |
| A-91 | FP967 | University of Saskatchewan, Crop Dev. Centre | A variant form of acetolactate synthase (ALS) was obtained from a chlorsulfuron tolerant line of A. thaliana and used to transform flax. | Linum usitatissimum L. (Flax, Linseed) |
| A-92 | 5345 | Monsanto Company | Resistance to lepidopteran pests through the introduction of the cry1Ac gene from Bacillus thuringiensis subsp. Kurstaki. | Lycopersicon esculentum (Tomato) |
| A-93 | 8338 | Monsanto Company | Introduction of a gene sequence encoding the enzyme 1-amino-cyclopropane-1-carboxylic acid deaminase (ACCd) that metabolizes the precursor of the fruit ripening hormone ethylene. | Lycopersicon esculentum (Tomato) |
| A-94 | 1345-4 | DNA Plant Technology Corporation | Delayed ripening tomatoes produced by inserting an additional copy of a truncated gene encoding 1-aminocyclopropane-1-carboxylic acid (ACC) synthase, which resulted in downregulation of the endogenous ACC synthase and reduced ethylene accumulation. | Lycopersicon esculentum (Tomato) |
| A-95 | 35 1 N | Agritope Inc. | Introduction of a gene sequence encoding the enzyme S-adenosylmethionine hydrolase that metabolizes the precursor of the fruit ripening hormone ethylene | Lycopersicon esculentum (Tomato) |
| A-96 | B, Da, F | Zeneca Seeds | Delayed softening tomatoes produced by inserting a truncated version of the polygalacturonase (PG) encoding gene in the sense or anti-sense orientation in order to reduce expression of the endogenous PG gene, and thus reduce pectin degradation. | Lycopersicon esculentum (Tomato) |
| A-97 | FLAVR SAVR | Calgene Inc. | Delayed softening tomatoes produced by inserting an additional copy of the polygalacturonase (PG) encoding gene in the anti-sense orientation in order to reduce expression of the endogenous PG gene and thus reduce pectin degradation. | Lycopersicon esculentum (Tomato) |
| A-98 | J101, J163 | Monsanto Company and Forage Genetics International | Glyphosate herbicide tolerant alfalfa (lucerne) produced by inserting a gene encoding the enzyme 5-enolpyruvylshikimate-3-phosphate synthase (EPSPS) from the CP4 strain of Agrobacterium tumefaciens. | Medicago sativa (Alfalfa) |
| A-99 | C/F/93/08-02 | Societe National d'Exploitation des Tabacs et Allumettes | Tolerance to the herbicides bromoxynil and ioxynil by incorporation of the nitrilase gene from Klebsiella pneumoniae. | Nicotiana tabacum L. (Tobacco) |
| A-100 | Vector 21-41 | Vector Tobacco Inc. | Reduced nicotine content through introduction of a second copy of the tobacco quinolinic acid phosphoribosyltransferase (QTPase) in the antisense orientation. The NPTII encoding gene from E. coli was introduced as a selectable marker to identify transformants. | Nicotiana tabacum L. (Tobacco) |

TABLE A-continued

Nonexhaustive list of transgenic plants and events for reworking the invention. Source: (AGBIOS, P.O. Box 475, 106 St. John St. Merrickville, Ontario K0G1N0, CANADA) database accessible at: http://www.agbios.com/dbase.php.

| No. | Transgenic event | Company | Description | Crop plant |
|---|---|---|---|---|
| A-101 | CL121, CL141, CFX51 | BASF Inc. | Tolerance to the imidazolinone herbicide, imazethapyr, induced by chemical mutagenesis of the acetolactate synthase (ALS) enzyme using ethyl methanesulfonate (EMS). | *Oryza sativa* (Rice) |
| A-102 | GAT-OS2 | | Glufosinate tolerance; WO 01/83818 | *Oryza sativa* (Rice) |
| A-103 | GAT-OS3 | | Glufosinate tolerance; US 2008-289060 | *Oryza sativa* (Rice) |
| A-104 | IMINTA-1, IMINTA-4 | BASF Inc. | Tolerance to imidazolinone herbicides induced by chemical mutagenesis of the acetolactate synthase (ALS) enzyme using sodium azide. | *Oryza sativa* (Rice) |
| A-105 | LLRICE06, LLRICE62 | Aventis CropScience | Glufosinate ammonium herbicide tolerant rice produced by inserting a modified phosphinothricin acetyltransferase (PAT) encoding gene from the soil bacterium *Streptomyces hygroscopicus*. | *Oryza sativa* (Rice) |
| A-106 | LLRICE601 | Bayer CropScience (Aventis CropScience(AgrEvo)) | Glufosinate ammonium herbicide tolerant rice produced by inserting a modified phosphinothricin acetyltransferase (PAT) encoding gene from the soil bacterium *Streptomyces hygroscopicus*. | *Oryza sativa* (Rice) |
| A-107 | PE-7 | | Insect resistance (Cry1Ac); WO 2008/114282 | *Oryza sativa* (Rice) |
| A-108 | PWC16 | BASF Inc. | Tolerance to the imidazolinone herbicide, imazethapyr, induced by chemical mutagenesis of the acetolactate synthase (ALS) enzyme using ethyl methanesulfonate (EMS). | *Oryza sativa* (Rice) |
| A-109 | TT51 | | Insect resistance (Cry1Ab/Cry1Ac); CN1840655 | *Oryza sativa* (Rice) |
| A-110 | C5 | United States Department of Agriculture - Agricultural Research Service | Plum pox virus (PPV) resistant plum tree produced through *Agrobacterium*-mediated transformation with a coat protein (CP) gene from the virus. | *Prunus domestica* (Plum) |
| | EH92-527 | BASF Plant Science | Crop composition; Amflora; Unique EU identifier: BPS-25271-9 | |
| A-111 | ATBT04-6, ATBT04-27, ATBT04-30, ATBT04-31, ATBT04-36, SPBT02-5, SPBT02-7 | Monsanto Company | Colorado potato beetle resistant potatoes produced by inserting the cry3A gene from *Bacillus thuringiensis* (subsp. *Tenebrionis*). | *Solanum tuberosum* L. (Potato) |
| A-112 | BT6, BT10, BT12, BT16, BT17, BT18, BT23 | Monsanto Company | Colorado potato beetle resistant potatoes produced by inserting the cry3A gene from *Bacillus thuringiensis* (subsp. *Tenebrionis*). | *Solanum tuberosum* L. (Potato) |
| A-113 | RBMT15-101, SEMT15-02, SEMT15-15 | Monsanto Company | Colorado potato beetle and potato virus Y (PVY) resistant potatoes produced by inserting the cry3A gene from *Bacillus thuringiensis* (subsp. *Tenebrionis*) and the coat protein encoding gene from PVY. | *Solanum tuberosum* L. (Potato) |
| A-114 | RBMT21-129, RBMT21-350, RBMT22-082 | Monsanto Company | Colorado potato beetle and potato leafroll virus (PLRV) resistant potatoes produced by inserting the cry3A gene from *Bacillus thuringiensis* (subsp. *Tenebrionis*) and the replicase encoding gene from PLRV. | *Solanum tuberosum* L. (Potato) |
| A-115 | AP205CL | BASF Inc. | Selection for a mutagenized version of the enzyme acetohydroxyacid synthase (AHAS), also known as acetolactate synthase (ALS) or acetolactate pyruvate- lyase. | *Triticum aestivum* (Wheat) |
| A-116 | AP602CL | BASF Inc. | Selection for a mutagenized version of the enzyme acetohydroxyacid synthase (AHAS), also known as acetolactate synthase (ALS) or acetolactate pyruvate- lyase. | *Triticum aestivum* (Wheat) |
| A-117 | BW255-2, BW238-3 | BASF Inc. | Selection for a mutagenized version of the enzyme acetohydroxyacid synthase (AHAS), also known as acetolactate synthase (ALS) or acetolactate pyruvate- lyase. | *Triticum aestivum* (Wheat) |
| A-118 | BW7 | BASF Inc. | Tolerance to imidazolinone herbicides induced by chemical mutagenesis of the | *Triticum aestivum* |

TABLE A-continued

Nonexhaustive list of transgenic plants and events for reworking the invention. Source: (AGBIOS, P.O. Box 475, 106 St. John St. Merrickville, Ontario K0G1N0, CANADA) database accessible at: http://www.agbios.com/dbase.php.

| No. | Transgenic event | Company | Description | Crop plant |
|---|---|---|---|---|
| | | | acetohydroxyacid synthase (AHAS) gene using sodium azide. | (Wheat) |
| A-119 | Event 1 | | *Fusarium* resistance (trichothecene 3-O-acetyltransferase); CA 2561992 | *Triticum aestivum* (Wheat) |
| A-120 | JOPLIN1 | | disease (fungal) resistance (trichothecene 3-O-acetyltransferase); US 2008064032 | *Triticum aestivum* (Wheat) |
| A-121 | MON71800 | Monsanto Company | Glyphosate tolerant wheat variety produced by inserting a modified 5-enolpyruvylshikimate-3-phosphate synthase (EPSPS) encoding gene from the soil bacterium *Agrobacterium tumefaciens*, strain CP4. | *Triticum aestivum* (Wheat) |
| A-122 | SWP965001 | Cyanamid Crop Protection | Selection for a mutagenized version of the enzyme acetohydroxyacid synthase (AHAS), also known as acetolactate synthase (ALS) or acetolactate pyruvate- lyase. | *Triticum aestivum* (Wheat) |
| A-123 | Teal 11A | BASF Inc. | Selection for a mutagenized version of the enzyme acetohydroxyacid synthase (AHAS), also known as acetolactate synthase (ALS) or acetolactate pyruvate- lyase. | *Triticum aestivum* (Wheat) |
| A-124 | 176 | Syngenta Seeds, Inc. | Insect-resistant maize produced by inserting the cry1Ab gene from *Bacillus thuringiensis* subsp. *kurstaki*. The genetic modification affords resistance to attack by the European corn borer (ECB). | *Zea mays* L. (Maize) |
| A-125 | 3272 | | Self processing corn (alpha-amylase); US 2006-230473 | *Zea mays* L. (Maize) |
| A-126 | 3751IR | Pioneer Hi-Bred International Inc. | Selection of somaclonal variants by culture of embryos on imidazolinone containing media. | *Zea mays* L. (Maize) |
| A-127 | 676, 678, 680 | Pioneer Hi-Bred International Inc. | Male-sterile and glufosinate ammonium herbicide tolerant maize produced by inserting genes encoding DNA adenine methylase and phosphinothricin acetyltransferase (PAT) from *Escherichia coli* and *Streptomyces viridochromogenes*, respectively. | *Zea mays* L. (Maize) |
| A-128 | ACS-ZMØØ3-2 × MON-ØØ81Ø-6 | Bayer CropScience (Aventis CropScience(AgrEvo)) | Stacked insect resistant and herbicide tolerant corn hybrid derived from conventional cross-breeding of the parental lines T25 (OECD identifier: ACS-ZMØØ3-2) and MON810 (OECD identifier: MON-ØØ81Ø-6). | *Zea mays* L. (Maize) |
| A-129 | B16 | | Glufosinate resistance; US 2003-126634 | *Zea mays* L. (Maize) |
| A-130 | B16 (DLL25) | Dekalb Genetics Corporation | Glufosinate ammonium herbicide tolerant maize produced by inserting the gene encoding phosphinothricin acetyltransferase (PAT) from *Streptomyces hygroscopicus*. | *Zea mays* L. (Maize) |
| A-131 | BT11 (X4334CBR, X4734CBR) | Syngenta Seeds, Inc. | Insect-resistant and herbicide tolerant maize produced by inserting the cry1Ab gene from *Bacillus thuringiensis* subsp. *kurstaki*, and the phosphinothricin N-acetyltransferase (PAT) encoding gene from *S. viridochromogenes*. | *Zea mays* L. (Maize) |
| A-132 | BT11 × MIR604 | Syngenta Seeds, Inc. | Stacked insect resistant and herbicide tolerant maize produced by conventional cross breeding of parental lines BT11 (OECD unique identifier: SYN-BTØ11-1) and MIR604 (OECD unique identifier: SYN-IR6Ø5-5). Resistance to the European Corn Borer and tolerance to the herbicide glufosinate ammonium (Liberty) is derived from BT11, which contains the cry1Ab gene from *Bacillus thuringiensis* subsp. *kurstaki*, and the phosphinothricin N-acetyltransferase (PAT) encoding gene from *S. viridochromogenes*. Corn rootworm-resistance is derived from MIR604 which contains the mcry3A gene from *Bacillus thuringiensis*. | *Zea mays* L. (Maize) |

TABLE A-continued

Nonexhaustive list of transgenic plants and events for reworking the invention. Source: (AGBIOS, P.O. Box 475, 106 St. John St. Merrickville, Ontario K0G1N0, CANADA) database accessible at: http://www.agbios.com/dbase.php.

| No. | Transgenic event | Company | Description | Crop plant |
|---|---|---|---|---|
| A-133 | BT11 × MIR604 × GA21 | Syngenta Seeds, Inc. | Stacked insect resistant and herbicide tolerant maize produced by conventional cross breeding of parental lines BT11 (OECD unique identifier: SYN-BTØ11-1), MIR604 (OECD unique identifier: SYN-IR6Ø5-5) and GA21 (OECD unique identifier: MON-ØØØ21-9). Resistance to the European Corn Borer and tolerance to the herbicide glufosinate ammonium (Liberty) is derived from BT11, which contains the cry1Ab gene from *Bacillus thuringiensis* subsp. *kurstaki*, and the phosphinothricin N-acetyltransferase (PAT) encoding gene from *S. viridochromogenes*. Corn rootworm-resistance is derived from MIR604 which contains the mcry3A gene from *Bacillus thuringiensis*. Tolerance to glyphosate herbicide is derived from GA21 which contains a modified EPSPS gene from maize. | *Zea mays* L. (Maize) |
| A-134 | CBH-351 | Aventis CropScience | Insect-resistant and glufosinate ammonium herbicide tolerant maize developed by inserting genes encoding Cry9C protein from *Bacillus thuringiensis* subsp *tolworthi* and phosphinothricin acetyltransferase (PAT) from *Streptomyces hygroscopicus*. | *Zea mays* L. (Maize) |
| A-135 | DAS-06275-8 | DOW AgroSciences LLC | Lepidopteran insect resistant and glufosinate ammonium herbicide-tolerant maize variety produced by inserting the cry1F gene from *Bacillus thuringiensis* var *aizawai* and the phosphinothricin acetyltransferase (PAT) from *Streptomyces hygroscopicus*. | *Zea mays* L. (Maize) |
| A-136 | DAS-59122-7 | DOW AgroSciences LLC and Pioneer Hi-Bred International Inc. | Corn rootworm-resistant maize produced by inserting the cry34Ab1 and cry35Ab1 genes from *Bacillus thuringiensis* strain PS149B1. The PAT encoding gene from *Streptomyces viridochromogenes* was introduced as a selectable marker; US 2006-070139 | *Zea mays* L. (Maize) |
| A-137 | DAS-59122-7 × NK603 | DOW AgroSciences LLC and Pioneer Hi-Bred International Inc. | Stacked insect resistant and herbicide tolerant maize produced by conventional cross breeding of parental lines DAS-59122-7 (OECD unique identifier: DAS-59122-7) with NK603 (OECD unique identifier: MON-ØØ6Ø3-6). Corn rootworm-resistance is derived from the line DAS-59122-7 which contains the cry34Ab1 and cry35Ab1 genes from *Bacillus thuringiensis* strain PS149B1. Tolerance to glyphosate herbicide is derived from NK603. | *Zea mays* L. (Maize) |
| A-138 | DAS-59122-7 × TC1507 × NK603 | DOW AgroSciences LLC and Pioneer Hi-Bred International Inc. | Stacked insect resistant and herbicide tolerant maize produced by conventional cross breeding of parental lines DAS-59122-7 (OECD unique identifier: DAS-59122-7) and TC1507 (OECD unique identifier: DAS-Ø15Ø7-1) with NK603 (OECD unique identifier: MON-ØØ6Ø3-6). Corn rootworm-resistance is derived from the line DAS-59122-7 which contains the cry34Ab1 and cry35Ab1 genes from *Bacillus thuringiensis* strain PS149B1. Lepidopteran resistance and tolerance to glufosinate ammonium herbicide is derived from TC1507. Tolerance to glyphosate herbicide is derived from NK603. | *Zea mays* L. (Maize) |
| A-139 | DAS-Ø15Ø7-1 × MON-ØØ6Ø3-6 | DOW AgroSciences LLC | Stacked insect resistant and herbicide tolerant maize produced by conventional cross-breeding of the parental lines 1507 (OECD identifier: DAS-Ø15Ø7-1) and NK603 (OECD identifier: MON-ØØ6Ø3-6). | *Zea mays* L. (Maize) |
| A-140 | DBT418 | Dekalb Genetics Corporation | Insect-resistant and glufosinate ammonium herbicide tolerant maize developed by inserting genes encoding Cry1AC protein from *Bacillus thuringiensis* subsp *kurstaki* and phosphinothricin acetyltransferase (PAT) from *Streptomyces hygroscopicus* | *Zea mays* L. (Maize) |

TABLE A-continued

Nonexhaustive list of transgenic plants and events for reworking the invention. Source: (AGBIOS, P.O. Box 475, 106 St. John St. Merrickville, Ontario K0G1N0, CANADA) database accessible at: http://www.agbios.com/dbase.php.

| No. | Transgenic event | Company | Description | Crop plant |
|---|---|---|---|---|
| A-141 | DK404SR | BASF Inc. | Somaclonal variants with a modified acetyl-CoA-carboxylase (ACCase) were selected by culture of embryos on sethoxydim enriched medium. | Zea mays L. (Maize) |
| A-142 | DP-098140-6 | | Glyphosate tolerance/ALS inhibitor tolerance; WO 2008/112019 | Zea mays L. (Maize) |
| A-143 | DP-Ø9814Ø-6 (Event 98140) | Pioneer Hi-Bred International Inc. | Corn line 98140 was genetically engineered to express the GAT4621 (glyphosate acetyltransferase) and ZM-HRA (modified version of a maize acetolactate synthase) proteins. The GAT4621 protein, encoded by the gat4621 gene, confers tolerance to glyphosate-containing herbicides by acetylating glyphosate and thereby rendering it non-phytotoxic. The ZM-HRA protein, encoded by the zm-hra gene, confers tolerance to the ALS-inhibiting class of herbicides. | Zea mays L. (Maize) |
| A-144 | Event 3272 | Syngenta Seeds, Inc. | Maize line expressing a heat stable alpha-amylase gene amy797E for use in the dry-grind ethanol process. The phosphomannose isomerase gene from E. coli was used as a selectable marker. | Zea mays L. (Maize) |
| A-145 | EXP1910IT | Syngenta Seeds, Inc. (formerly Zeneca Seeds) | Tolerance to the imidazolinone herbicide, imazethapyr, induced by chemical mutagenesis of the acetolactate synthase (ALS) enzyme using ethyl methanesulfonate (EMS). | Zea mays L. (Maize) |
| A-146 | FI117 | | Glyphosate resistance; U.S. Pat. No. 6,040,497 | Zea mays L. (Maize) |
| A-147 | GA21 | Monsanto Company | Introduction, by particle bombardment, of a modified 5-enolpyruvyl shikimate-3-phosphate synthase (EPSPS), an enzyme involved in the shikimate biochemical pathway for the production of the aromatic amino acids. | Zea mays L. (Maize) |
| A-148 | GAT-ZM1 | | Glufosinate tolerance; WO 01/51654 | Zea mays L. (Maize) |
| A-149 | GG25 | | Glyphosate resistance; U.S. Pat. No. 6,040,497 | Zea mays L. (Maize) |
| A-150 | GJ11 | | Glyphosate resistance; U.S. Pat. No. 6,040,497 | Zea mays L. (Maize) |
| A-151 | IT | Pioneer Hi-Bred International Inc. | Tolerance to the imidazolinone herbicide, imazethapyr, was obtained by in vitro selection of somaclonal variants. | Zea mays L. (Maize) |
| A-152 | LY038 | Monsanto Company | Altered amino acid composition, specifically elevated levels of lysine, through the introduction of the cordapA gene, derived from Corynebacterium glutamicum, encoding the enzyme dihydrodipicolinate synthase (cDHDPS); U.S. Pat. No. 7,157,281 | Zea mays L. (Maize) |
| A-153 | MIR162 | | Insect resistance; WO 2007142840 | Zea mays L. (Maize) |
| A-154 | MIR604 | Syngenta Seeds, Inc. | Corn rootworm resistant maize produced by transformation with a modified cry3A gene. The phosphomannose isomerase gene from E. coli was used as a selectable marker; (Cry3a055); EP 1 737 290 | Zea mays L. (Maize) |
| A-155 | MIR604 × GA21 | Syngenta Seeds, Inc. | Stacked insect resistant and herbicide tolerant maize produced by conventional cross breeding of parental lines MIR604 (OECD unique identifier: SYN-IR6Ø5-5) and GA21 (OECD unique identifier: MON-ØØØ21-9). Corn rootworm-resistance is derived from MIR604 which contains the mcry3A gene from Bacillus thuringiensis. Tolerance to glyphosate herbicide is derived from GA21. | Zea mays L. (Maize) |
| A-156 | MON80100 | Monsanto Company | Insect-resistant maize produced by inserting the cry1Ab gene from Bacillus thuringiensis subsp. kurstaki. The genetic modification affords resistance to attack by the European corn borer (ECB). | Zea mays L. (Maize) |

TABLE A-continued

Nonexhaustive list of transgenic plants and events for reworking the invention. Source: (AGBIOS, P.O. Box 475, 106 St. John St. Merrickville, Ontario K0G1N0, CANADA) database accessible at: http://www.agbios.com/dbase.php.

| No. | Transgenic event | Company | Description | Crop plant |
|---|---|---|---|---|
| A-157 | MON802 | Monsanto Company | Insect-resistant and glyphosate herbicide tolerant maize produced by inserting the genes encoding the Cry1Ab protein from *Bacillus thuringiensis* and the 5-enolpyruvylshikimate-3-phosphate synthase (EPSPS) from *A. tumefaciens* strain CP4. | *Zea mays* L. (Maize) |
| A-158 | MON809 | Pioneer Hi-Bred International Inc. | Resistance to European corn borer (*Ostrinia nubilalis*) by introduction of a synthetic cry1Ab gene. Glyphosate resistance via introduction of the bacterial version of a plant enzyme, 5-enolpyruvyl shikimate-3-phosphate synthase (EPSPS). | *Zea mays* L. (Maize) |
| A-159 | MON810 | Monsanto Company | Insect-resistant maize produced by inserting a truncated form of the cry1Ab gene from *Bacillus thuringiensis* subsp. *kurstaki* HD-1. The genetic modification affords resistance to attack by the European corn borer (ECB); US 2004-180373 | *Zea mays* L. (Maize) |
| A-160 | MON810 × MON88017 | Monsanto Company | Stacked insect resistant and glyphosate tolerant maize produced by conventional cross-breeding of the parental lines MON810 (OECD identifier: MON-ØØ81Ø-6) and MON88017 (OECD identifier: MON-88Ø17-3). European corn borer (ECB) resistance is derived from a truncated form of the cry1Ab gene from *Bacillus thuringiensis* subsp. *kurstaki* HD-1 present in MON810. Corn rootworm resistance is derived from the cry3Bb1 gene from *Bacillus thuringiensis* subspecies *kumamotoensis* strain EG4691 present in MON88017. Glyphosate tolerance is derived from a 5-enolpyruvylshikimate-3-phosphate synthase (EPSPS) encoding gene from *Agrobacterium tumefaciens* strain CP4 present in MON88017. | *Zea mays* L. (Maize) |
| A-161 | MON832 | Monsanto Company | Introduction, by particle bombardment, of glyphosate oxidase (GOX) and a modified 5-enolpyruvyl shikimate-3-phosphate synthase (EPSPS), an enzyme involved in the shikimate biochemical pathway for the production of the aromatic amino acids. | *Zea mays* L. (Maize) |
| A-162 | MON863 | Monsanto Company | Corn rootworm resistant maize produced by inserting the cry3Bb1 gene from *Bacillus thuringiensis* subsp. *kumamotoensis*. | *Zea mays* L. (Maize) |
| A-163 | MON87460 | | Drought tolerance; Water deficit tolerance; WO 2009/111263 | *Zea mays* L. (Maize) |
| A-164 | MON88017 | Monsanto Company | Corn rootworm-resistant maize produced by inserting the cry3Bb1 gene from *Bacillus thuringiensis* subspecies *kumamotoensis* strain EG4691. Glyphosate tolerance derived by inserting a 5-enolpyruvylshikimate-3-phosphate synthase (EPSPS) encoding gene from *Agrobacterium tumefaciens* strain CP4; WO2005059103 | *Zea mays* L. (Maize) |
| A-165 | MON89034 | Monsanto Company | Maize event expressing two different insecticidal proteins from *Bacillus thuringiensis* providing resistance to a number of lepidopteran pests; insect resistance (*Lepidoptera* -Cry1A.105-Cry2Ab); WO 2007140256 | *Zea mays* L. (Maize) |
| A-166 | MON89034 × MON88017 | Monsanto Company | Stacked insect resistant and glyphosate tolerant maize produced by conventional cross-breeding of the parental lines MON89034 (OECD identifier: MON-89Ø34-3) and MON88017 (OECD identifier: MON-88Ø17-3). Resistance to Lepiopteran insects is derived from two cry genes present in MON89043. Corn rootworm resistance is derived from a single cry gene and glyphosate tolerance is derived from a 5-enolpyruvylshikimate-3-phosphate synthase (EPSPS) encoding gene from *Agrobacterium tumefaciens* present in MON88017. | *Zea mays* L. (Maize) |

TABLE A-continued

Nonexhaustive list of transgenic plants and events for reworking the invention. Source: (AGBIOS, P.O. Box 475, 106 St. John St. Merrickville, Ontario K0G1N0, CANADA) database accessible at: http://www.agbios.com/dbase.php.

| No. | Transgenic event | Company | Description | Crop plant |
|---|---|---|---|---|
| A-167 | MON-ØØ6Ø3-6 × MON-ØØ81Ø-6 | Monsanto Company | Stacked insect resistant and herbicide tolerant corn hybrid produced by conventional cross-breeding of the parental lines NK603 (OECD identifier: MON-ØØ6Ø3-6) and MON810 (OECD identifier: MON-ØØ81Ø-6). | Zea mays L. (Maize) |
| A-168 | MON-ØØ81Ø-6 × LY038 | Monsanto Company | Stacked insect resistant and enhanced lysine content maize produced by conventional cross-breeding of the parental lines MON810 (OECD identifier: MON-ØØ81Ø-6) and LY038 (OECD identifier: REN-ØØØ38-3). | Zea mays L. (Maize) |
| A-169 | MON-ØØ863-5 × MON-ØØ6Ø3-6 | Monsanto Company | Stacked insect resistant and herbicide tolerant corn hybrid produced by conventional cross-breeding of the parental lines MON863 (OECD identifier: MON-ØØ863-5) and NK603 (OECD identifier: MON-ØØ6Ø3-6). | Zea mays L. (Maize) |
| A-170 | MON-ØØ863-5 × MON-ØØ81Ø-6 | Monsanto Company | Stacked insect resistant corn hybrid produced by conventional cross-breeding of the parental lines MON863 (OECD identifier: MON-ØØ863-5) and MON810 (OECD identifier: MON-ØØ81Ø-6) | Zea mays L. (Maize) |
| A-171 | MON-ØØ863-5 × MON-ØØ81Ø-6 × MON-ØØ6Ø3-6 | Monsanto Company | Stacked insect resistant and herbicide tolerant corn hybrid produced by conventional cross-breeding of the stacked hybrid MON-ØØ863-5 × MON-ØØ81Ø-6 and NK603 (OECD identifier: MON-ØØ6Ø3-6). | Zea mays L. (Maize) |
| A-172 | MON-ØØØ21-9 × MON-ØØ81Ø-6 | Monsanto Company | Stacked insect resistant and herbicide tolerant corn hybrid derived from conventional cross-breeding of the parental lines GA21 (OECD identifider: MON-ØØØ21-9) and MON810 (OECD identifier: MON-ØØ81Ø-6). | Zea mays L. (Maize) |
| A-173 | MS3 | Bayer CropScience (Aventis CropScience(AgrEvo)) | Male sterility caused by expression of the barnase ribonuclease gene from *Bacillus amyloliquefaciens*; PPT resistance was via PPT-acetyltransferase (PAT). | Zea mays L. (Maize) |
| A-174 | MS6 | Bayer CropScience (Aventis CropScience(AgrEvo)) | Male sterility caused by expression of the barnase ribonuclease gene from *Bacillus amyloliquefaciens*; PPT resistance was via PPT-acetyltransferase (PAT). | Zea mays L. (Maize) |
| A-175 | NK603 | Monsanto Company | Introduction, by particle bombardment, of a modified 5-enolpyruvyl shikimate-3-phosphate synthase (EPSPS), an enzyme involved in the shikimate biochemical pathway for the production of the aromatic amino acids. | Zea mays L. (Maize) |
| A-176 | PV-ZMGT32 (NK603) | | Glyphosate tolerance; US 2007-056056 | Zea mays L. (Maize) |
| A-177 | PV-ZMGT32(nk603) | | Glyphosate tolerance; US 2007292854 | Zea mays L. (Maize) |
| A-178 | PV-ZMIR13 (MON863) | | Insect resistance (Cry3Bb); US 2006-095986 | Zea mays L. (Maize) |
| A-179 | SYN-BTØ11-1 × MON-ØØØ21-9 | Syngenta Seeds, Inc. | Stacked insect resistant and herbicide tolerant maize produced by conventional cross breeding of parental lines BT11 (OECD unique identifier: SYN-BTØ11-1) and GA21 (OECD unique identifier: MON-ØØØ21-9). | Zea mays L. (Maize) |
| A-180 | T14, T25 | Bayer CropScience (Aventis CropScience(AgrEvo)) | Glufosinate herbicide tolerant maize produced by inserting the phosphinothricin N-acetyltransferase (PAT) encoding gene from the aerobic actinomycete *Streptomyces viridochromogenes*. | Zea mays L. (Maize) |
| A-181 | TC1507 | Mycogen (c/o Dow AgroSciences); Pioneer (c/o Dupont) | Insect-resistant and glufosinate ammonium herbicide tolerant maize produced by inserting the cry1F gene from *Bacillus thuringiensis* var. *aizawai* and the phosphinothricin N-acetyltransferase encoding gene from *Streptomyces viridochromogenes*. | Zea mays L. (Maize) |

TABLE A-continued

Nonexhaustive list of transgenic plants and events for reworking the invention. Source: (AGBIOS, P.O. Box 475, 106 St. John St. Merrickville, Ontario K0G1N0, CANADA) database accessible at: http://www.agbios.com/dbase.php.

| No. | Transgenic event | Company | Description | Crop plant |
|---|---|---|---|---|
| A-182 | TC1507 × DAS-59122-7 | DOW AgroSciences LLC and Pioneer Hi-Bred International Inc. | Stacked insect resistant and herbicide tolerant maize produced by conventional cross breeding of parental lines TC1507 (OECD unique identifier: DAS-Ø15Ø7-1) with DAS-59122-7 (OECD unique identifier: DAS-59122-7). Resistance to lepidopteran insects is derived from TC1507 due to the presence of the cry1F gene from *Bacillus thuringiensis* var. *aizawai*. Corn rootworm-resistance is derived from the line DAS-59122-7 which contains the cry34Ab1 and cry35Ab1 genes from *Bacillus thuringiensis* strain PS149B1. Tolerance to glufosinate ammonium herbicide is derived from TC1507 from the phosphinothricin N-acetyltransferase encoding gene from *Streptomyces viridochromogenes*. | *Zea mays* L. (Maize) |
| A-183 | VIP1034 | | Insect resistance; WO 03/052073 | *Zea mays* L. (Maize) |

In one embodiment of the invention, the plants A-1 to A-183 in Table A, in whole or in part, or propagation material of these plants are or is treated or contacted with the active ingredient combinations of the invention or with the mixture/beneficial species combinations of the invention.

TABLE B

Non-exhaustive list of transgenic plants for the implementation of the invention, from the APHIS database of the United States Department of Agriculture (USDA). The database is found at: http://www.aphis.usda.gov/animal_welfare/efoia/index.shtml.

| No. | Petition | Extension of Petition Number *** | Institution | Plant | Transformation event or line | EA final judgment and provision |
|---|---|---|---|---|---|---|
| B-1 | 10-070-01p | | Virginia Tech | Peanut | *Sclerotinia* blight resistant | N70, P39, and W171 |
| B-2 | 09-349-01p | | Dow AgroSciences | Soybean | 2,4-D and glufosinate tolerant | DAS-68416-4 |
| B-3 | 09-328-01p | | Bayer Crop Science | Soybean | glyphosate and isoxaflutole tolerant | FG72 |
| B-4 | 09-233-01p | | Dow | Corn | 2,4-D and ACCase-inhibitor tolerant | DAS-40278-9 |
| B-5 | 09-201-01p | | Monsanto | Soybean | improved fatty acid profile | MON-877Ø5-6 |
| B-6 | 09-183-01p | | Monsanto | Soybean | stearidonic acid produced | MON-87769 |
| B-7 | 09-082-01p | | Monsanto | Soybean | Lepidopteran resistant | MON 87701 |
| B-8 | 09-063-01p | | Stine Seed | Corn | Glyphosate tolerant | HCEM485 |
| B-9 | 09-055-01p | | Monsanto | Corn | Drought Tolerant | MON 87460 |
| B-10 | 09-015-01p | | BASF Plant Science, LLC | Soybean | imidazolinone tolerant | BPS-CV127-9 Soybean |
| B-11 | 08-366-01p | | ArborGen | *Eucalyptus* | Freeze Tolerant, Fertility Altered | ARB-FTE1-08 |
| B-12 | 08-340-01p | | Bayer | Cotton | Glufosinate Tolerant, Insect Resistant | T304-40XGHB119 |
| B-13 | 08-338-01p | | Pioneer | Corn | Male Sterile, Fertility Restored, Visual Marker | DP-32138-1 |
| B-14 | 08-315-01p | | Florigene | Rose | Altered Flower Color | IFD-524Ø1-4 and IFD-529Ø1-9 |
| B-15 | 07-108-01p | | Syngenta | Cotton | Lepidopteran Resistant | COT67B |
| B-16 | 06-354-01p | | Pioneer | Soybean | High Oleic Acid | DP-3Ø5423-1 |
| B-17 | | | | | | |
| B-18 | 05-280-01p | | Syngenta | Corn | Thermostable alpha-amylase | 3272 |
| B-19 | | | | | | |
| B-20 | 04-110-01p | | Monsanto & Forage Genetics | Alfalfa | Glyphosate Tolerant | J101, J163 |
| B-21 | | | | | | |
| B-22 | | | | | | |

TABLE B-continued

Non-exhaustive list of transgenic plants for the implementation of the invention, from the APHIS database of the United States Department of Agriculture (USDA). The database is found at: http://www.aphis.usda.gov/animal_welfare/efoia/index.shtml.

| No. | Petition | Extension of Petition Number *** | Institution | Plant | Transformation event or line | EA final judgment and provision |
|---|---|---|---|---|---|---|
| B-23 | | | | | | |
| B-24 | 03-104-01p | | Monsanto & Scotts | Creeping bentgrass | Glyphosate Tolerant | ASR368 |
| B-25 | | | | | | |
| B-26 | | | | | | |
| B-27 | | | | | | |
| B-28 | | | | | | |
| B-29 | | | | | | |
| B-30 | 07-253-01p | | Syngenta | Corn | Lepidopteran resistant | MIR-162 Maize |
| B-31 | | | | | | |
| B-32 | 07-152-01p | | Pioneer | Corn | glyphosate & Imidazolinone tolerant | DP-098140-6 |
| B-33 | | | | | | |
| B-34 | 04-337-01p | | University of Florida | Papaya | Papaya Ringspot Virus Resistant | X17-2 |
| B-35 | | | | | | |
| B-36 | 06-332-01p | | Bayer CropScience | Cotton | Glyphosate tolerant | GHB614 |
| B-37 | | | | | | |
| B-38 | 06-298-01p | | Monsanto | Corn | European Corn Borer resistant | MON 89034 |
| B-39 | | | | | | |
| B-40 | 06-271-01p | | Pioneer | Soybean | Glyphosate & acetolactate synthase tolerant | 356043 (DP-356Ø43-5) |
| B-41 | | | | | | |
| B-42 | 06-234-01p | 98-329-01p | Bayer CropScience | Rice | Phosphinothricin tolerant | LLRICE601 |
| B-43 | | | | | | |
| B-44 | 06-178-01p | | Monsanto | Soybean | Glyphosate tolerant | MON 89788 |
| B-45 | | | | | | |
| B-46 | 04-362-01p | | Syngenta | Corn | Corn Rootworm Protected | MIR604 |
| B-47 | | | | | | |
| B-48 | | | | | | |
| B-49 | 04-264-01p | | ARS | Plum | Plum Pox Virus Resistant | C5 |
| B-50 | | | | | | |
| B-51 | 04-229-01p | | Monsanto | Corn | High Lysine | LY038 |
| B-52 | | | | | | |
| B-53 | 04-125-01p | | Monsanto | Corn | Corn Rootworm Resistant | 88017 |
| B-54 | | | | | | |
| B-55 | 04-086-01p | | Monsanto | Cotton | Glyphosate Tolerant | MON 88913 |
| B-56 | | | | | | |
| B-57 | | | | | | |
| B-58 | 03-353-01p | | Dow | Corn | Corn Rootworm Resistant | 59122 |
| B-59 | | | | | | |
| B-60 | 03-323-01p | | Monsanto | Sugar Beet | Glyphosate Tolerant | H7-1 |
| B-61 | | | | | | |
| B-62 | 03-181-01p | 00-136-01p | Dow | Corn | Lepidopteran Resistant & Phosphinothricin tolerant | TC-6275 |
| B-63 | | | | | | |
| B-64 | 03-155-01p | | Syngenta | Cotton | Lepidopteran Resistant | COT 102 |
| B-65 | | | | | | |
| B-66 | 03-036-01p | | Mycogen/Dow | Cotton | Lepidopteran Resistant | 281-24-236 |
| B-67 | | | | | | |
| B-68 | 03-036-02p | | Mycogen/Dow | Cotton | Lepidopteran Resistant | 3006-210-23 |
| B-69 | | | | | | |
| B-70 | 02-042-01p | | Aventis | Cotton | Phosphinothericin tolerant | LLCotton25 |
| B-71 | 01-324-01p | 98-216-01p | Monsanto | Rapeseed | Glyphosate tolerant | RT200 |
| B-72 | 01-206-01p | 98-278-01p | Aventis | Rapeseed | Phosphinothricin tolerant & pollination control | MS1 & RF1/RF2 |
| B-73 | 01-206-02p | 97-205-01p | Aventis | Rapeseed | Phosphinothricin tolerant | Topas 19/2 |
| B-74 | 01-137-01p | | Monsanto | Corn | Corn Rootworm Resistant | MON 863 |
| B-75 | 01-121-01p | | Vector | Tobacco | Reduced nicotine | Vector 21-41 |
| B-76 | 00-342-01p | | Monsanto | Cotton | Lepidopteran resistant | Cotton Event 15985 |
| B-77 | 00-136-01p | | Mycogen c/o Dow & Pioneer | Corn | Lepidopteran resistant & phosphinothricin tolerant | Line 1507 |
| B-78 | 00-011-01p | 97-099-01p | Monsanto | Corn | Glyphosate tolerant | NK603 |
| B-79 | 99-173-01p | 97-204-01p | Monsanto | Potato | PLRV & CPB resistant | RBMT22-82 |

TABLE B-continued

Non-exhaustive list of transgenic plants for the implementation of the invention, from the APHIS database of the United States Department of Agriculture (USDA). The database is found at: http://www.aphis.usda.gov/animal_welfare/efoia/index.shtml.

| No. | Petition | Extension of Petition Number *** | Institution | Plant | Transformation event or line | EA final judgment and provision |
|---|---|---|---|---|---|---|
| B-80 | 98-349-01p | 95-228-01p | AgrEvo | Corn | Phosphinothricin tolerant and Male sterile | MS6 |
| B-81 | 98-335-01p | | U. of Saskatchewan | Flax | Tolerant to soil residues of sulfonyl urea herbicide | CDC Triffid |
| B-82 | 98-329-01p | | AgrEvo | Rice | Phosphinothricin tolerant | LLRICE06, LLRICE62 |
| B-83 | 98-278-01p | | AgrEvo | Rapeseed | Phosphinothricin tolerant & Pollination control | MS8 & RF3 |
| B-84 | 98-238-01p | | AgrEvo | Soybean | Phosphinothricin tolerant | GU262 |
| B-85 | 98-216-01p | | Monsanto | Rapeseed | Glyphosate tolerant | RT73 |
| B-86 | 98-173-01p | | Novartis Seeds & Monsanto | Beet | Glyphosate tolerant | GTSB77 |
| B-87 | 98-014-01p | 96-068-01p | AgrEvo | Soybean | Phosphinothricin tolerant | A5547-127 |
| B-88 | 97-342-01p | | Pioneer | Corn | Male sterile & Phosphinothricin tolerant | 676, 678, 680 |
| B-89 | 97-339-01p | | Monsanto | Potato | CPB & PVY resistant | RBMT15-101, SEMT15-02, SEMT15-15 |
| B-90 | 97-336-01p | | AgrEvo | Beet | Phosphinothricin tolerant | T-120-7 |
| B-91 | 97-287-01p | | Monsanto | Tomato | Lepidopteran resistant | 5345 |
| B-92 | 97-265-01p | | AgrEvo | Corn | Phosphinothricin tolerant & Lepidopteran resistant | CBH-351 |
| B-93 | 97-205-01p | | AgrEvo | Rapeseed | Phosphinothricin tolerant | T45 |
| B-94 | 97-204-01p | | Monsanto | Potato | CPB & PLRV resistant | RBMT21-129 & RBMT21-350 |
| B-95 | 97-148-01p | | Bejo | *Cichorium intybus* | Male sterile | RM3-3, RM3-4, RM3-6 |
| B-96 | 97-099-01p | | Monsanto | Corn | Glyphosate tolerant | GA21 |
| B-97 | 97-013-01p | | Calgene | Cotton | Bromoxynil tolerant & Lepidopteran resistant | Events 31807 & 31808 |
| B-98 | 97-008-01p | | Du Pont | Soybean | Oil profile altered | G94-1, G94-19, G-168 |
| B-99 | 96-317-01p | | Monsanto | Corn | Glyphosate tolerant & ECB resistant | MON802 |
| B-100 | 96-291-01p | | DeKalb | Corn | European Corn Borer resistant | DBT418 |
| B-101 | 96-248-01p | 92-196-01p | Calgene | Tomato | Fruit ripening altered | 1 additional FLAVRSAVR line |
| B-102 | 96-068-01p | | AgrEvo | Soybean | Phosphinothricin tolerant | W62, W98, A2704-12, A2704-21, A5547-35 |
| B-103 | 96-051-01p | | Cornell U | Papaya | PRSV resistant | 55-1, 63-1 |
| B-104 | 96-017-01p | 95-093-01p | Monsanto | Corn | European Corn Borer resistant | MON809 & MON810 |
| B-105 | 95-352-01p | | Asgrow | Squash | CMV, ZYMV, WMV2 resistant | CZW-3 |
| B-106 | 95-338-01p | | Monsanto | Potato | CPB resistant | SBT02-5 & -7, ATBT04-6 &-27, -30, -31, -36 |
| B-107 | 95-324-01p | | Agritope | Tomato | Fruit ripening altered | 35 1 N |
| B-108 | 95-256-01p | | Du Pont | Cotton | Sulfonylurea tolerant | 19-51a |
| B-109 | 95-228-01p | | Plant Genetic Systems | Corn | Male sterile | MS3 |
| B-110 | 95-195-01p | | Northrup King | Corn | European Corn Borer resistant | Bt11 |

TABLE B-continued

Non-exhaustive list of transgenic plants for the implementation of the invention, from the APHIS database of the United States Department of Agriculture (USDA). The database is found at: http://www.aphis.usda.gov/animal_welfare/efoia/index.shtml.

| No. | Petition | Extension of Petition Number *** | Institution | Plant | Transformation event or line | EA final judgment and provision |
|---|---|---|---|---|---|---|
| B-111 | 95-179-01p | 92-196-01p | Calgene | Tomato | Fruit ripening altered | 2 additional FLAVRSAVR lines |
| B-112 | 95-145-01p | | DeKalb | Corn | Phosphinothricin tolerant | B16 |
| B-113 | 95-093-01p | | Monsanto | Corn | Lepidopteran resistant | MON 80100 |
| B-114 | 95-053-01p | | Monsanto | Tomato | Fruit ripening altered | 8338 |
| B-115 | 95-045-01p | | Monsanto | Cotton | Glyphosate tolerant | 1445, 1698 |
| B-116 | 95-030-01p | 92-196-01p | Calgene | Tomato | Fruit ripening altered | 20 additional FLAVRSAVR lines |
| B-117 | 94-357-01p | | AgrEvo | Corn | Phosphinothricin tolerant | T14, T25 |
| B-118 | 94-319-01p | | Ciba Seeds | Corn | Lepidopteran resistant | Event 176 |
| B-119 | 94-308-01p | | Monsanto | Cotton | Lepidopteran resistant | 531, 757, 1076 |
| B-120 | 94-290-01p | | Zeneca & Petoseed | Tomato | Fruit polygalacturonase level decreased | B, Da, F |
| B-121 | 94-257-01p | | Monsanto | Potato | Coleopteran resistant | BT6, BT10, BT12, BT16, BT17, BT18, BT23 |
| B-122 | 94-230-01p | 92-196-01p | Calgene | Tomato | Fruit ripening altered | 9 additional FLAVRSAVR lines |
| B-123 | 94-228-01p | | DNA Plant Tech | Tomato | Fruit ripening altered | 1345-4 |
| B-124 | 94-227-01p | 92-196-01p | Calgene | Tomato | Fruit ripening altered | Line N73 1436-111 |
| B-125 | 94-090-01p | | Calgene | Rapeseed | Oil profile altered | pCGN3828-212/86- 18 & 23 |
| B-126 | 93-258-01p | | Monsanto | Soybean | Glyphosate tolerant | 40-3-2 |
| B-127 | 93-196-01p | | Calgene | Cotton | Bromoxynil tolerant | BXN |
| B-128 | 92-204-01p | | Upjohn | Squash | WMV2 & ZYMV resistant | ZW-20 |
| B-129 | 92-196-01p | | Calgene | Tomato | Fruit ripening altered | FLAVR SAVR |

Abbreviations used in this table:
CMV—cucumber mosaic virus
CPB—Colorado potato beetle
PLRV—potato leafroll virus
PRSV—papaya ringspot virus
PVY—potato virus Y
WMV2—water melon mosaic virus 2
ZYMV—zucchini yellow mosaic virus In one embodiment of the invention, the plants B-1 to B-129 from Table B, in whole or in part, or propagation material of these plants, are or is treated or contacted with the active ingredient combinations of the invention or with the mixture/beneficial species combinations of the invention.

TABLE C

Non-exhaustive list of traits for reproducing the invention, with reference to documents in which they are described.

| No. | Trait | Reference |
|---|---|---|
| C-1 | Water useage efficiency | WO 2000/073475 |
| | | WO2009/150541 |
| C-2 | Nitrogen useage efficiency | WO 1995/009911 |
| | | WO 1997/030163 |
| | | WO 2007/092704 |
| | | WO 2007/076115 |
| | | WO 2005/103270 |
| | | WO 2002/002776 |
| | | WO2008/051608 |
| | | WO2008/112613 |
| | | WO2009/015096 |
| | | WO2009/061776 |
| | | WO2009/105492 |
| | | WO2009/105612 |
| | | WO2009/117853 |

TABLE C-continued

Non-exhaustive list of traits for reproducing the invention, with reference to documents in which they are described.

| No. | Trait | Reference |
|---|---|---|
|  |  | WO2010/006010 |
|  |  | WO2009/117853 |
|  |  | WO2009/061776 |
|  |  | WO2009/015096 |
|  |  | WO2009/105492 |
|  |  | WO2009/105612 |
|  |  | WO2010/006010 |
|  |  | WO2010/007496 |
| C-3 | Improved photosynthesis | WO 2008/056915 |
|  |  | WO 2004/101751 |
| C-4 | Nematode resistance | WO 1995/020669 |
|  |  | WO 2001/051627 |
|  |  | WO 2008/139334 |
|  |  | WO 2008/095972 |
|  |  | WO 2006/085966 |
|  |  | WO 2003/033651 |
|  |  | WO 1999/060141 |
|  |  | WO 1998/012335 |
|  |  | WO 1996/030517 |
|  |  | WO 1993/018170 |
|  |  | WO2008/095886 |
|  |  | WO2008/095887 |
|  |  | WO2008/095888 |
|  |  | WO2008/095889 |
|  |  | WO2008/095910 |
|  |  | WO2008/095911 |
|  |  | WO2008/095916 |
|  |  | WO2008/095919 |
|  |  | WO2008/095969 |
|  |  | WO2008/095970 |
|  |  | WO2008/095972 |
|  |  | WO2008/110522 |
|  |  | WO2008/139334 |
|  |  | WO2008/152008 |
|  |  | WO2009/000736 |
|  |  | WO2009/065863 |
|  |  | WO2009/112505 |
|  |  | WO2009/132089 |
|  |  | WO2010/023186 |
|  |  | WO2010/025172 |
|  |  | WO2010/027793 |
|  |  | WO2010/027799 |
|  |  | WO2010/027804 |
|  |  | WO2010/027805 |
|  |  | WO2010/027808 |
|  |  | WO2010/027809 |
| C-5 | Reduced pod dehiscence | WO 2006/009649 |
|  |  | WO 2004/113542 |
|  |  | WO 1999/015680 |
|  |  | WO 1999/000502 |
|  |  | WO 1997/013865 |
|  |  | WO 1996/030529 |
|  |  | WO 1994/023043 |
| C-6 | Aphid resistance | WO 2006/125065 |
|  |  | WO 1997/046080 |
|  |  | WO 2008/067043 |
|  |  | WO 2004/072109 |
|  |  | WO2009/091860 |
|  |  | WO 2009021153 |
|  |  | WO2010036764 |
| C-7 | *Sclerotinia* resistance | WO 2006/135717 |
|  |  | WO 2006/055851 |
|  |  | WO 2005/090578 |
|  |  | WO 2005/000007 |
|  |  | WO 2002/099385 |
|  |  | WO 2002/061043 |
| C-8 | *Botrytis* resistance | WO 2006/046861 |
|  |  | WO 2002/085105 |
| C-9 | *Bremia* resistance | US 20070022496 |
|  |  | WO 2000/063432 |
|  |  | WO 2004/049786 |
|  |  | WO2009/111627 |
| C10 | *Erwinia* resistance | WO 2004/049786 |
| C-11 | Closterovirus resistance | WO 2007/073167 |
|  |  | WO 2007/053015 |
|  |  | WO 2002/022836 |
| C-12 | Stress tolerance (including drought tolerance) | WO 2010/019838 |
|  |  | WO 2009/049110 |
|  |  | WO2008/002480 |
|  |  | WO2005/033318 |
|  |  | WO2008/002480 |
|  |  | WO2008/005210 |
|  |  | WO2008/006033 |
|  |  | WO2008/008779 |
|  |  | WO2008/022486 |
|  |  | WO2008/025097 |
|  |  | WO2008/027534 |
|  |  | WO2008/027540 |
|  |  | WO2008/037902 |
|  |  | WO2008/046069 |
|  |  | WO2008/053487 |
|  |  | WO2008/057642 |
|  |  | WO2008/061240 |
|  |  | WO2008/064222 |
|  |  | WO2008/064341 |
|  |  | WO2008/073617 |
|  |  | WO2008/074025 |
|  |  | WO2008/076844 |
|  |  | WO2008/096138 |
|  |  | WO2008/110848 |
|  |  | WO2008/116829 |
|  |  | WO2008/117537 |
|  |  | WO2008/121320 |
|  |  | WO2008/125245 |
|  |  | WO2008/142034 |
|  |  | WO2008/142036 |
|  |  | WO2008/150165 |
|  |  | WO2008/092935 |
|  |  | WO2008/145675 |
|  |  | WO2009/010460 |
|  |  | WO2009/016240 |
|  |  | WO2009/031664 |
|  |  | WO2009/038581 |
|  |  | WO2009/049110 |
|  |  | WO2009/053511 |
|  |  | WO2009/054735 |
|  |  | WO2009/067580 |
|  |  | WO2009/073605 |
|  |  | WO2009/077611 |
|  |  | WO2009/079508 |
|  |  | WO2009/079529 |
|  |  | WO2009/083958 |
|  |  | WO2009/086229 |
|  |  | WO2009/092009 |
|  |  | WO2009/094401 |
|  |  | WO2009/094527 |
|  |  | WO2009/102965 |
|  |  | WO2009/114733 |
|  |  | WO2009/117448 |
|  |  | WO2009/126359 |
|  |  | WO2009/126462 |
|  |  | WO2009/129162 |
|  |  | WO2009/132057 |
|  |  | WO2009/141824 |
|  |  | WO2009/148330 |
|  |  | WO2010/037714 |
|  |  | WO2010/031312 |
|  |  | WO2010/006010 |
|  |  | WO2010/007495 |
|  |  | WO2010/019838 |
|  |  | WO2010/025513 |
| C-13 | Tobamovirus resistance | WO 2006/038794 |
|  |  | WO2002081713 |
|  |  | WO2009086850 |
| C-14 | Yield | WO2008/125983A2 |
|  |  | WO2008/112613A1 |
|  |  | WO2008/118394A1 |
|  |  | WO2008/015263A2 |

TABLE C-continued

Non-exhaustive list of traits for reproducing the invention, with reference to documents in which they are described.

| No. | Trait | Reference |
|---|---|---|
| | | WO2008/021021A2 |
| | | WO2008/043849A2 |
| | | WO2008/044150A2 |
| | | WO2008/049183A1 |
| | | WO2008/056915A1 |
| | | WO2008/059048A1 |
| | | WO2008/062049A1 |
| | | WO2008/071767A1 |
| | | WO2008/074891A2 |
| | | WO2008/087932A1 |
| | | WO2008/092910A1 |
| | | WO2008/092935A2 |
| | | WO2008/104598A2 |
| | | WO2008/111779A1 |
| | | WO2008/122980A2 |
| | | WO2008/135206A2 |
| | | WO2008/135467A2 |
| | | WO2008/135603A2 |
| | | WO2008/137108A2 |
| | | WO2008/138975A1 |
| | | WO2008/142146A1 |
| | | WO2008/142163A2 |
| | | WO2008/145629A2 |
| | | WO2008/145675A2 |
| | | WO2008/145761A1 |
| | | WO2008/148872A1 |
| | | WO2008/073617A2 |
| | | WO2009//127671A1 |
| | | WO2009/0 65912A2 |
| | | WO2009/000789A1 |
| | | WO2009/000848A1 |
| | | WO2009/000876A1 |
| | | WO2009/003977A2 |
| | | WO2009/009142A2 |
| | | WO2009/012467A2 |
| | | WO2009/013225A2 |
| | | WO2009/013263A2 |
| | | WO2009/014665A2 |
| | | WO2009/016104A1 |
| | | WO2009/016212A2 |
| | | WO2009/016232A2 |
| | | WO2009/021548A1 |
| | | WO2009/034188A1 |
| | | WO2009/037279A1 |
| | | WO2009/037329A2 |
| | | WO2009/037338A1 |
| | | WO2009/040665A2 |
| | | WO2009/056566A2 |
| | | WO2009/060400A1 |
| | | WO2009/068564A1 |
| | | WO2009/068588A2 |
| | | WO2009/072676A1 |
| | | WO2009/073069A2 |
| | | WO2009/075860A2 |
| | | WO2009/077973A1 |
| | | WO2009/080743A2 |
| | | WO2009/080802A2 |
| | | WO2009/091518A2 |
| | | WO2009/092772A2 |
| | | WO2009/095455A1 |
| | | WO2009/095641A2 |
| | | WO2009/095881A2 |
| | | WO2009/097133A2 |
| | | WO2009/102978A2 |
| | | WO2009/106596A2 |
| | | WO2009/108513A2 |
| | | WO2009/113684A1 |
| | | WO2009/134339A2 |
| | | WO2009/135130A2 |
| | | WO2009/135810A1 |
| | | WO2009/145290A1 |
| | | WO2009/150170A1 |
| | | WO2009/153208A1 |
| | | WO2009/156360A1 |
| | | WO2010/012796A1 |
| | | WO2010/003917A1 |
| | | WO2010/037228A1 |
| | | WO2010/000794A1 |
| | | WO2010/005298A2 |
| | | WO2010/006732A2 |
| | | WO2010/007035A1 |
| | | WO2010/007496A2 |
| | | WO2010/012760A2 |
| | | WO2010/019872A1 |
| | | WO2010/023310A2 |
| | | WO2010/023320A2 |
| | | WO2010/025465A1 |
| | | WO2010/025466A2 |
| | | WO2010/028205A1 |
| | | WO2010/028456A1 |
| | | WO2010/033564A1 |
| | | WO2010/034652A1 |
| | | WO2010/034672A1 |
| | | WO2010/034681A1 |
| | | WO2010/035784A1 |
| | | WO2010/036866A1 |
| | | WO2010/039750A2 |

In one embodiment of the invention, the plants which encompass or express the traits C-1 to C-14 from Table C, in whole or in part, or propagation material of these plants, are or is treated or contacted with the active ingredient combinations of the invention or with the mixture/beneficial species combinations of the invention.

TABLE D

Non-exhaustive list of transgenic events and traits to which the invention may be applied, with reference to patent applications.

| No. | Plant species | Transgenic event | Trait | Patent reference |
|---|---|---|---|---|
| D-1 | Maize | PV-ZMGT32 (NK603) | Glyphosate tolerance | US 2007-056056 |
| D-2 | Maize | MIR604 | Insect resistance (Cry3a055) | EP-A 1 737 290 |
| D-3 | Maize | LY038 | High lysine content | U.S. Pat. No. 7,157,281 |
| D-4 | Maize | 3272 | Self-processing maize (alpha-amylase) | US 2006-230473 |
| D-5 | Maize | PV-ZMIR13 (MON863) | Insect resistance (Cry3Bb) | US 2006-095986 |
| D-6 | Maize | DAS-59122-7 | Insect resistance (Cry34Ab1/Cry35Ab1) | US 2006-070139 |
| D-7 | Maize | TC1507 | Insect resistance (Cry1F) | U.S. Pat. No. 7,435,807 |
| D-8 | Maize | MON810 | Insect resistance (Cry1Ab) | US 2004-180373 |
| D-9 | Maize | VIP1034 | Insect resistance | WO 03/052073 |
| D-10 | Maize | B16 | Glufosinate resistance | US 2003-126634 |

TABLE D-continued

Non-exhaustive list of transgenic events and traits to which the invention may be applied, with reference to patent applications.

| No. | Plant species | Transgenic event | Trait | Patent reference |
|---|---|---|---|---|
| D-11 | Maize | GA21 | Glyphosate resistance | U.S. Pat. No. 6,040,497 |
| D-12 | Maize | GG25 | Glyphosate resistance | U.S. Pat. No. 6,040,497 |
| D-13 | Maize | GJ11 | Glyphosate resistance | U.S. Pat. No. 6,040,497 |
| D-14 | Maize | FI117 | Glyphosate resistance | U.S. Pat. No. 6,040,497 |
| D-15 | Maize | GAT-ZM1 | Glufosinate tolerance | WO 01/51654 |
| D-16 | Maize | DP-098140-6 | Glyphosate tolerance/ALS inhibitor tolerance | WO 2008/112019 |
| D-17 | Wheat | Event 1 | *Fusarium* resistance (trichothecene 3-O-acetyl-transferase) | CA 2561992 |
| D-18 | Sugar beet | T227-1 | Glyphosate tolerance | US 2004-117870 |
| D-19 | Sugar beet | H7-1 | Glyphosate tolerance | WO 2004-074492 |
| D-20 | Soyabean | MON89788 | Glyphosate tolerance | US 2006-282915 |
| D-21 | Soyabean | A2704-12 | Glufosinate tolerance | WO 2006/108674 |
| D-22 | Soyabean | A5547-35 | Glufosinate tolerance | WO 2006/108675 |
| D-23 | Soyabean | DP-305423-1 | High oil content/ALS inhibitor tolerance | WO 2008/054747 |
| D-24 | Rice | GAT-OS2 | Glufosinate tolerance | WO 01/83818 |
| D-25 | Rice | GAT-OS3 | Glufosinate tolerance | US 2008-289060 |
| D-26 | Rice | PE-7 | Insect resistance (Cry1Ac) | WO 2008/114282 |
| D-27 | Oilseed rape | MS-B2 | Male sterility | WO 01/31042 |
| D-28 | Oilseed rape | MS-BN1/RF-BN1 | Male sterility/restoration | WO 01/41558 |
| D-29 | Oilseed rape | RT73 | Glyphosate resistance | WO 02/36831 |
| D-30 | Cotton | CE43-67B | Insect resistance (Cry1Ab) | WO 2006/128573 |
| D-31 | Cotton | CE46-02A | Insect resistance (Cry1Ab) | WO 2006/128572 |
| D-32 | Cotton | CE44-69D | Insect resistance (Cry1Ab) | WO 2006/128571 |
| D-33 | Cotton | 1143-14A | Insect resistance (Cry1Ab) | WO 2006/128569 |
| D-34 | Cotton | 1143-51B | Insect resistance (Cry1Ab) | WO 2006/128570 |
| D-35 | Cotton | T342-142 | Insect resistance (Cry1Ab) | WO 2006/128568 |
| D-36 | Cotton | event3006-210-23 | Insect resistance (Cry1Ac) | WO 2005/103266 |
| D-37 | Cotton | PV-GHGT07 (1445) | Glyphosate tolerance | US 2004-148666 |
| D-38 | Cotton | MON88913 | Glyphosate tolerance | WO 2004/072235 |
| D-39 | Cotton | EE-GH3 | Glyphosate tolerance | WO 2007/017186 |
| D-40 | Cotton | T304-40 | Insect resistance | WO2008/122406 |
| D-41 | Cotton | Cot202 | Insect resistance (VIP3) | US 2007-067868 |
| D-42 | Cotton | LLcotton25 | Glufosinate resistance | WO 2007/017186 |
| D-43 | Cotton | EE-GH5 | Insect resistance (Cry1Ab) | WO 2008/122406 |
| D-44 | Cotton | event 281-24-236 | Insect resistance z(Cry1F) | WO 2005/103266 |
| D-45 | Cotton | Cot102 | Insect resistance (Vip3A) | US 2006-130175 |
| D-46 | Cotton | MON 15985 | Insect resistance (Cry1A/Cry2Ab) | US 2004-250317 |
| D-47 | Bent grass | Asr-368 | Glyphosate tolerance | US 2006-162007 |
| D-48 | Aubergine | EE-1 | Insect resistance (Cry1Ac) | WO 2007/091277 |

In one embodiment, the plants which encompass a transgenic event as per D-1 to D-48 from Table D or express such a trait, in whole or in part or propagation material from these plants, are or is treated or contacted with the active ingredient combinations of the invention or with the mixture/beneficial species combinations of the invention.

TABLE E

Non-exhaustive list of transgenic events and traits and associated trade names.

| No. | Trade name | Plant | Company | Genetically modified traits | Additional information |
|---|---|---|---|---|---|
| E-1 | Roundup Ready ® | *Beta vulgaris* (sugar beet) | Monsanto Company | Glyphosate tolerance | |
| E-2 | InVigor ® | *Brassica napus* (Argentinian canola) | Bayer CropScience | Canola was genetically modified with the following outcome: Ø expression of the gene imparting tolerance to the herbicide glyfosinate ammonium; Ø introduction of a new hybrid breeding system for canola, based on genetically modified male sterility (MS) and fertility restorer (RF) lines; Ø expression of a gene for antibiotic resistance. | |

TABLE E-continued

Non-exhaustive list of transgenic events and traits and associated trade names.

| No. | Trade name | Plant | Company | Genetically modified traits | Additional information |
|---|---|---|---|---|---|
| E-3 | Liberty Link ® | *Brassica napus* (Argentinian canola) | Bayer CropScience | Phosphinotricin tolerance | |
| E-4 | Roundup Ready ® | *Brassica napus* (canola) | Monsanto Company | Glyphosate tolerance | |
| E-5 | Clearfield ® | (Canola) | BASF Corporation | non-GMO, imazamox tolerance | |
| E-6 | Optimum ™ GAT ™ | *Glycine max* L. (soybean) | Pioneer Hi-Bred International, Inc | Tolerance to glyphosate and ALS herbicides | |
| E-7 | Roundup Ready ® | *Glycine max* L. (soybean) | Monsanto Company | Glyphosate tolerance | |
| E-8 | Roundup RReady2Yiel ™ | *Glycine max* L. (soybean) | Monsanto Company | Glyphosate tolerance | |
| E-9 | STS ® | *Glycine max* L. (soybean) | DuPont | Tolerance to sulphonylureas | |
| E-10 | YIELD GARD ® | *Glycine max* L. (soybean) | Monsanto Company | | |
| E-11 | AFD ® | *Gossypium hirsutum* L. (cotton) | Bayer CropScience | The lines include e.g. AFD5062LL, AFD5064F, AFD 5065B2F; AFD seed is available in various varieties with integrated technology, such as, for example, the Bollgard ®, Bollgard II, Roundup Ready, Roundup Ready Flex, and LibertyLink ® technologies | |
| E-12 | Bollgard II ® | *Gossypium hirsutum* L. (cotton) | Monsanto Company | MON 15985 event: Cry2(A)b1; Cry1A(c) | |
| E-13 | Bollgard ® | *Gossypium hirsutum* L. (sugar beet) | Monsanto Company | Cry 1Ac | |
| E-14 | FiberMax ® | *Gossypium hirsutum* L. (cotton) | Bayer CropScience | | |
| E-15 | Liberty Link ® | *Gossypium hirsutum* L. (cotton) | Bayer CropScience | Phosphinotricin tolerance | |
| E-16 | Nucotn 33B | *Gossypium hirsutum* L. (cotton) | Delta Pine and Land | Bt toxin in the lines from Delta Pine: Cry1Ac | |
| E-17 | Nucotn 35B | *Gossypium hirsutum* L. (cotton) | Delta Pine and Land | Bt toxin in lines from Delta Pine: Cry1Ac | |
| E-18 | Nucotn ® | *Gossypium hirsutum* L. (cotton) | Delta Pine and Land | Bt toxin in lines from Delta Pine | |
| E-19 | PhytoGen ™ | *Gossypium hirsutum* L. (cotton) | PhytoGen Seed Company, Dow AgroSciences LLC | Encompasses varieties which contain, for example, Roundup Ready flex, Widestrike | |
| E-20 | Roundup Ready Flex ® | *Gossypium hirsutum* L. (cotton) | Monsanto Company | Glyphosate tolerance | |
| E-21 | Roundup Ready ® | *Gossypium hirsutum* L. (cotton) | Monsanto Company | Glyphosate tolerance | |
| E-22 | Widestrike ™ | *Gossypium hirsutum* L. (cotton) | Dow AgroSciences LLC | Cry1F and Cry1Ac | Monsanto/Dow |
| E-23 | YIELD GARD ® | *Gossypium hirsutum* L. (cotton) | Monsanto Company | | http://www.garstseed.com/ GarstClient/Technology/agrisure.aspx |
| E-24 | Roundup Ready ® | *Medicago sativa* (alfalfa) | Monsanto Company | Glyphosate tolerance | |
| E-25 | Clearfield ® | *Oryza sativa* (rice) | BASF Corporation | non-GMO, imazamox tolerance | |
| E-26 | NewLeaf ® | *Solanum tuberosum* L. (potatoes) | Monsanto Company | Resistance to infection by potato leaf roll virus (PLRV) and feeding damage caused by the potato beetle *Leptinotarsa decemlineata* | |

TABLE E-continued

Non-exhaustive list of transgenic events and traits and associated trade names.

| No. | Trade name | Plant | Company | Genetically modified traits | Additional information |
|---|---|---|---|---|---|
| E-27 | NewLeaf ® plus | *Solanum tuberosum* L. (potatoes) | Monsanto Company | Resistance to infection by potato leaf roll virus (PLRV) and feeding damage caused by the potato beetle *Leptinotarsa decemlineata* | http://www.dowagro.com/ phytogen/index.htm |
| E-28 | Protecta ® | *Solanum tuberosum* L. (potatoes) | | | |
| E-29 | Clearfield ® | Sunflower | BASF Corporation | non-GMO, imazamox tolerance | |
| E-30 | Roundup Ready ® | *Triticum aestivum* (wheat) | Monsanto Company | Tolerance to glyphosate, NK603 | |
| E-31 | Clearfield ® | Wheat | BASF Corporation | non-GMO, imazamox tolerance | |
| E-32 | Agrisure ® (family) | *Zea mays* L. (maize) | Syngenta Seeds, Inc. | Including Agrisure CB/LL (BT 11 event plus tolerance to phosphinotricin through GA21 event); Agrisure CB/LL/RW (Bt 11event, modified synthetic Cry3A gene, tolerance to phosphinotricin through GA21 event); Agrisure GT (glyphosate tolerance); Agrisure GT/CB/LL(tolerance to glyphosate and to phosphinotricin through GA21 event, Bt 11 event); Agrisure 3000GT (CB/LL/RW/GT: tolerance to glyphosate and against phosphinotricin through GA21 event, Bt 11 event, modified synthetic Cry3A gene); Agrisure GT/RW (tolerance to glyphosate, modified synthetic Cry3A gene); Agrisure RW (modified synthetic Cry3A-Gen); future traits | |
| E-33 | BiteGard ® | *Zea mays* L. (maize) | Novartis Seeds | cry1A(b) gene. | |
| E-34 | Bt-Xtra ® | *Zea mays* L. (maize) | DEKALB Genetics Corporation | cry1Ac gene. | |
| E-35 | Clearfield ® | *Zea mays* L. (maize) | BASF Corporation | non-GMO, imazamox tolerance | |
| E-36 | Herculex ® (family) | *Zea mays* L. (maize) | Dow AgroSciences LLC | | |
| E-37 | IMI ® | *Zea mays* L. (maize) | DuPont | Tolerance to imidazolinones | |
| E-38 | KnockOut ® | *Zea mays* L. (v) | Syngenta Seeds, Inc. | SYN-EV176-9: cry1A(b) gene. | |
| E-39 | Mavera ® | *Zea mays* L. (maize) | Renessen LLC | lysine-rich | http://www.dowagro.com/widestrike/ |
| E-40 | NatureGard ® | *Zea mays* L. (maize) | Mycogen | cry1A(b) gene. | |
| E-41 | Roundup Ready ® | *Zea mays* L. (maize) | Monsanto Company | Glyphosate tolerance | http:/www.starlinkcorn.com/ starlinkcorn.htm |
| E-42 | Roundup Ready ® 2 | *Zea mays* L. ( maize) | Monsanto Company | Glyphosate tolerance | |
| E-43 | SmartStax | *Zea mays* L. (maize) | Monsanto Company | Combination of eight genes | |
| E-44 | StarLink ® | *Zea mays* L. (maize) | Aventis CropScience –> Bayer CropScience | Cry9c gene. | |
| E-45 | STS ® | *Zea mays* L. (maize) | DuPont | Tolerance to sulfonylureas | |
| E-46 | YIELD GARD ® | *Zea mays* L. (maize) | Monsanto Company | Mon810, Cry1Ab1; resistance against the European maize borer | http://www.dowagro.com/herculex/ about/herculexfamily/ |

TABLE E-continued

Non-exhaustive list of transgenic events and traits and associated trade names.

| No. | Trade name | Plant | Company | Genetically modified traits | Additional information |
|---|---|---|---|---|---|
| E-47 | YieldGard ® Plus | Zea mays L. (maize) | Monsanto Company | Mon810 × Mon863, dual combination, resistance against European corn borer and corn root worm | |
| E-48 | YieldGard ® Rootworm | Zea mays L. (maize) | Monsanto Company | Mon863, Cry3Bb1, resistance against corn root worm | |
| E-49 | YieldGard ® VT | Zea mays L. (maize) | Monsanto Company | Trait combination | |
| E-50 | YieldMaker ™ | Zea mays L. (maize) | DEKALB Genetics Corporation | Contains Roundup Ready 2 technology, YieldGard VT, YieldGard Corn Borer, YieldGard Rootworm and YieldGard Plus | |

In one embodiment, the plants which encompass a transgenic event as per E-1 to E-50 from Table E or express such a trait, in whole or in part, or propagation material of these plants, are or is treated or contacted with the active ingredient combinations of the invention or with the mixture/beneficial species combinations of the invention.

The plants listed may be treated with particular advantage in accordance with the invention with the active ingredient combinations or mixture/beneficial species combinations of the invention. The preference ranges indicated above for the combinations apply also in respect of the treatment of these plants. Particular emphasis may be given to plant treatment with the active ingredient combinations and mixture/beneficial species combinations set out specifically in the present text.

The active ingredient combinations and mixture/beneficial species combinations can be converted into the typical formulations, such as solutions, emulsions, wettable powders, suspensions, powders, dusts, pastes, soluble powders, granules, suspension emulsion concentrates, active ingredient-impregnated natural and synthetic materials, and microencapsulations in polymeric substances.

These formulations are prepared in a known way, as for example by mixing the active ingredient with extenders, i.e. liquid solvents and/or solid carriers, optionally with the use of surface-active agents, i.e. emulsifiers and/or dispersants and/or foam formers.

Examples of suitable extenders include water, polar and apolar organic chemical liquids, for example from the classes of the aromatic and non-aromatic hydrocarbons (such as paraffins, alkylbenzenes, alkylnaphthalenes, chlorobenzenes), the alcohols and polyols (which optionally may also be substituted, etherified and/or esterified), the ketones (such as acetone, cyclohexanone), esters (including fats and oils) and (poly)ethers, the simple and substituted amines, amides, lactams (such as N-alkylpyrrolidones) and lactones, the sulphones and sulphoxides (such as dimethyl sulphoxide).

Where water is used as an extender it is also possible, for example, to use organic solvents as co-solvents. Liquid solvents contemplated include essentially the following: aromatics, such as xylene, toluene, or alkyl-naphthalenes, chlorinated aromatics and chlorinated aliphatic hydrocarbons, such as chlorobenzenes, chloroethylenes or methylene chloride, aliphatic hydrocarbons, such as cyclohexane or paraffins, for example mineral oil fractions, mineral and vegetable oils, alcohols, such as butanol or glycol and also their ethers and esters, ketones such as acetone, methyl ethyl ketone, methyl isobutyl ketone or cyclohexanone, strongly polar solvents, such as dimethylformamide and dimethyl sulphoxide, and water.

Solid carriers contemplated include the following:
e.g. ammonium salts and natural finely ground minerals, such as kaolins, argillaceous earths, talc, chalk, quartz, attapulgite, montmorillonite or diatomaceous earth, and synthetic finely ground minerals, such as highly disperse silica, aluminium oxide and silicates; solid carriers contemplated for granules include the following: e.g. crushed and fractionated natural minerals such as calcite, marble, pumice, sepiolite, dolomite, and synthetic granules of organic and inorganic meals, and also granules of organic material such as paper, sawdust, coconut shells, maize cobs and tobacco stalks; emulsifiers and/or foam formers that are contemplated include the following: e.g. nonionic and anionic emulsifiers, such as polyoxymethylene fatty acid esters, polyoxymethylene fatty alcohol ethers, e.g. alkylaryl polyglycol ethers, alkylsulphonates, alkyl sulphates, arylsulphonates and protein hydrolysates; dispersants contemplated include nonionic and/or anionic compounds, from the classes, for example, of the alcohol POE and/or POP ethers, acid esters and/or POP-POE esters, alkyl aryl esters and/or POP POE ethers, fatty adducts and/or POP POE adducts, POE- and/or POP-polyol derivatives, POE- and/or POP-sorbitan or -sugar adducts, alkyl or aryl sulphates, sulphonates and phosphates, or the corresponding PO ether adducts. Additionally, suitable oligomers and polymers, based for example on vinylic monomers, on acrylic acid, comprising EO and/or PO alone or in conjunction with, for example, (poly)alcohols or (poly)amines. Use may also be made of lignin and its sulphonic acid derivatives, simple and modified celluloses, aromatic and/or aliphatic sulphonic acids, and the adducts thereof with formaldehyde.

In the formulations there may be adhesives used such as carboxymethylcellulose, natural and synthetic polymers in powder, granule or latex form, such as gum arabic, polyvinyl alcohol, polyvinyl acetate, and also natural phospholipids, such as cephalins and lecithins and synthetic phospholipids. Further possible additives include mineral and vegetable oils.

It is possible to use colorants such as inorganic pigments, e.g. iron oxide, titanium oxide, Prussian blue, and organic dyes, such as alizarin dyes, azo dyes and metal phthalocyanine dyes, and trace nutrients such as salts of iron, manganese, boron, copper, cobalt, molybdenum and zinc.

The formulations generally contain between 0.1% and 95% by weight of active ingredient, preferably between 0.5% and 90%, and in addition preferably extenders and/or surface-active agents.

The active ingredient content of the use forms prepared from the commercial formulations may vary within wide ranges. The active ingredient concentration of the use forms may be from 0.0000001% up to 95% by weight active ingredient, preferably between 0.0001% and 1% by weight.

Application takes place in a conventional way adapted to the use forms.

The good insecticidal and/or acaricidal activity of the active ingredient combinations is evident from the examples below. While the individual active ingredients have weaknesses in their activity, the combinations display an activity which exceeds a simple summation of activities.

A synergistic effect with insecticides/acaricides is present whenever the activity of the active ingredient combinations is greater than the sum of the activities of the active ingredients when applied individually.

The activity which can be expected for a given combination of two active ingredients can be calculated by the method of S. R. Colby, Weeds 15 (1967), 20-22), as follows:

if
X is the degree of destruction expressed in % of the untreated control when active ingredient A is employed at an application rate of m g/ha or in a concentration of m ppm,
Y is the degree of destruction expressed in % of the untreated control when active ingredient B is employed at an application rate of n g/ha or in a concentration of n ppm, and
E is the degree of destruction expressed in % of the untreated control when the active ingredients A and B are employed at application rates of m and n g/ha or in a concentration of m and n ppm,
then $$E = X + Y - \frac{X \cdot Y}{100}$$

If the actual degree of insecticidal destruction is greater than calculated, then the combination is superadditive in its destruction—in other words, there is a synergistic effect. In this case, the degree of destruction actually observed must be greater than the figure for the expected degree of destruction (E) as calculated from the formula given above.

Particularly preferred are animal pests from the order of the mites (Acari), in particular from the families of the gall mites (Eriophyidae), thread-footed mites (Tarsonemidae) and spider mites (Tetranychidae).

Gall Mites (Eriophyidae)

Especially preferred is the control of the following species from the family of the gall mites (Eriophyidae) in the following crops:

| | |
|---|---|
| Aculops lycopersici | in vegetables such as, for example, tomatoes, aubergines, in |
| Aculops pelekassi | citrus such as, for example, oranges, grapefruits, s tangerine |
| Aculus schlechtendali | in pome fruit such as, for example, apples, in stone fruit |
| Aculus fokeui, Aculus berochensis Aculus conutus | such as, for example, quetsch, peaches |
| Aceria sheldoni | in citrus such as, for example, oranges, clementines, limes, in |
| Aceria tulipai | vegetables such as, for example, onions, cereals such as, for example, wheat |
| Epitrimerus pyri | in pome fruit such as, for example, pears, in grapevines |
| Epitrimerus vitis | |

-continued

| | |
|---|---|
| Eriophyes avellanae | in nuts, such as, for example, hazelnuts, in conifers, in |
| Eriophyes guerreronis | tropical crops such as, for example, coconuts, lychees, in |
| Eriophyes litchii | pome fruit such as, for example, pears, in soft fruits such as, |
| Eriophyes piri Eriophyes ribis Eriophyes theae Eriophyes vitis | for example, currants, in tea, in grapevines |
| Phyllocoptrutua oleivora | in citrus, such as, for example, oranges, grapefruits, tangerines |

Thread-Footed Mites (Tarsonemidae)

Especially preferred is the control of the following species from the family of the thread-footed mites (Tarsonemidae) in the following crops:

| | |
|---|---|
| Hemitarsonemus latus | in ornamentals, in soybeans, in cotton, in vegetables such as chilies, bell peppers, tea, conifers |

Spider Mites (Tetranychidae)

Especially preferred is the control of the following species from the family of the spider mites (Tetranychidae) in the following crops:

| | |
|---|---|
| Brevipalpus lewisi | in citrus such as, for example, oranges, lemons, grapefruits, |
| Brevipalpus obovatus | tangerines, in ornamentals, for example Solanaceae, in coffee, |
| Brevipalpus oudemansi | in tropical fruits such as, for example, mangoes, passion fruit, |
| Brevipalpus phoenicis | papayas, in grapevines, in tea, in pome, fruit such as for example, apples and pears, in nuts, for example walnuts |
| Eotetranychus carpirii | in grapevines, in nuts such as, for example, pecan nuts, in |
| Eotetranychus willamelti | citrus such as, for example, limes, clementines, grapefruits, |
| Eotetranychus hicoriae Eotetranychus yumensis | pome fruit, for example apples |
| Panonychus citri | in grapevines, in pome fruit, for example apples, pears, in |
| Panonychus ulmi | stone fruit, for example peaches, cherries, quetsch, plums, in citrus such as, for example, oranges, tangerines, grapefruits, limes, in soft fruit such as, for example, currants, in nuts such as, for example, almonds, walnuts |
| Tetranychus canadensis | in pome fruit such as, for example, apples, pears, in stone |
| Tetranychus urtricae | fruit such as, for example, plums, peaches, cherries, in soft |
| Tetranychus parcificus | fruit such as, for example, strawberries, gooseberries, |
| Tetranychus cinnabarinus | raspberries, in vegetables such as, for example, tomatoes, |
| Tetranychus turkestani | cucumber, aubergines, bell pepper, chilies, in ornamentals |
| Tetranychus viennensis | such as, for example, roses, orchids, flower maple, in conifers, in |
| Tetranychus kanzawai | woody species, in grapevines, in nuts such as, for example,almonds, pistachios, in soybeans, in cotton, in tea, in hops |
| Oligonychus coffeae | in coffee, in maize, in tropical fruits such as, for example, |
| Oligonychus ilicis | avocados, persimmon, in stone fruit such as, for example, |
| Oligonychus mexicanus Oligonychus persea Oligonychus punicae | plums, in grapevines |

EXAMPLE 1

In plots measuring approximately 14 m², aubergines (around 11 weeks after planting out) of the cultivar "Heilongchangqie" are treated in three replications against *Tetranychus urticae*. Application takes place using a sprayer. In this example, the mixture of the active ingredients Oberon, Example (I), and abamectin, Example (VI), is tested against the commercial standards abamectin (018 EC) and Oberon (240 SC) at the stated application rates and in the stated mixing ratios. The water application rate is 450 l/ha.

Evaluation is made 1 day and 55 days after treatment, by scoring the destruction of the eggs on the leaves.

| Active ingredient | Application rate g a.i./ha | Destruction (% Abbott) 1 day | 55 days |
|---|---|---|---|
| Abamectin (VI) | 10 | 19.8 | 0 |
| Oberon (I) | 120 | 26.7 | 0 |
| Oberon (I) + Abamectin (VI) | 120 + 6 | 65.1* (41.2)** | 42.0* (0)** |

*activity found
**activity calculated by Colby formula

A further evaluation is made 45 and 55 days after treatment, by scoring the destruction of the nymphs on the leaves.

| Active ingredient | Application rate g a.i./ha | Destruction (% Abbott) 45 days | 55 days |
|---|---|---|---|
| Abamectin (VI) | 10 | 0 | 0 |
| Oberon (I) | 120 | 14.8 | 24.1 |
| Oberon (I) + Abamectin (VI) | 120 + 6 | 57.2* (14.8)** | 61.4* (24.1)** |

*activity found
**activity calculated by Colby formula

EXAMPLE 2

In plots measuring approximately 6 m², roses of the cultivar "Blizard" with an age of approximately 3 years are treated in three replications against *Tetranychus urticae*. Application takes place using a back-mounted spray (3.5 bar). In this example, the mixture of the active ingredients Oberon, Example (I), and abamectin, Example (VI), is tested against the commercial standards abamectin (018 EC) and Oberon (240 SC) at the stated application rates and in the stated mixing ratios. The water application rate is 1320 l/ha.

Evaluation is made 3 days after treatment, by counting the adults on the leaves/square inch. Subsequently, the activity is calculated as a percentage by the method of Henderson and Tilton.

| Active ingredient | Application rate g a.i./ha | Activity (% H. + T.) 3 days |
|---|---|---|
| Abamectin (VI) | 21 | 0 |
| Oberon (I) | 210 | 40.7 |
| Oberon (I) + Abamectin (VI) | 210 + 21 | 72.2* (40.7)** |

*activity found, calculated by Henderson and Tilton method
**activity calculated by method of Colby

| Active ingredient | Application rate g a.i./ha | Activity (% H. + T.) 3 days |
|---|---|---|
| Abamectin (VI) | 10.5 | 0 |
| Oberon (I) | 105 | 32.2 |
| Oberon (I) + Abamectin (VI) | 105 + 10.5 | 52.7* (32.2)** |

*activity found, calculated by Henderson and Tilton method
**activity calculated by method of Colby

EXAMPLE 3

In plots measuring approximately 6 m², tomatoes of the cultivar "Leader" are treated in three replications against *Tetranychus urticae*. Application takes place using a back-mounted spray (4.5 bar). In this example, the mixture of the active ingredients Oberon, Example (I), and abamectin, Example (VI), is tested against the commercial standards abamectin (018 EC) and Oberon (480 SC) at the stated application rates and in the stated mixing ratios. The water application rate is 1000 l/ha.

Evaluation is made 3 days after treatment, by scoring the destruction of the adults on the leaves.

| Active ingredient | Application rate g a.i./ha | Destruction (% Abbott) 3 days |
|---|---|---|
| Abamectin (VI) | 10 | 45.8 |
| Oberon (I) | 120 | 25.0 |
| Oberon (I) + Abamectin (VI) | 120 + 6 | 75* (59.4)** |

*activity found
**activity calculated by Colby formula

EXAMPLE 4

In plots measuring approximately 15 m², cotton plants of the cultivar "BRS Aroeira" with a height of approximately 80 cm are treated in three replications against *Tetranychus urticae*. Application takes place using a spray at 2.5 bar. In this example, the mixture of the active ingredients Oberon, Example (I), and abamectin, Example (VI), is tested against the commercial standards abamectin (018 EC) and Oberon (240 SC) at the stated application rates and in the stated mixing ratios. The water application rate is 200 l/ha.

Evaluation is made 13 days after treatment, by scoring the destruction of the population on the leaves.

| Active ingredient | Application rate g a.i./ha | Destruction (% Abbott) 13 days |
|---|---|---|
| Abamectin (VI) | 7.2 | 16.5 |
| Oberon (I) | 120 | 58.5 |
| Oberon (I) + Abamectin (VI) | 120 + 7.2 | 70.0* (65.3)** |

*activity found
**activity calculated by Colby formula

EXAMPLE 5

In plots measuring approximately 14 m², roses (growth stage 46) of the cultivar "Freedom" in double rows are treated in three replications against *Tetranychus urticae*. Application takes place using a back-mounted spray. In this example, the mixture of the active ingredients Oberon, Example (I), and abamectin, Example (VI), is tested against the commercial standards abamectin (018 EC) and Oberon (240 SC) at the stated application rates and in the stated mixing ratios. The water application rate is 1000 l/ha.

Evaluation is made 1 day after treatment, by scoring the destruction of the population on the leaves.

| Active ingredient | Application rate g a.i./ha | Activity (% Abbott) 1 day |
|---|---|---|
| Abamectin (VI) | 6 | 27 |
| Oberon (I) | 120 | 32.4 |
| Oberon (I) + Abamectin (VI) | 120 + 6 | 59.5* (50.7)** |

*activity found
**activity calculated by Colby formula

EXAMPLE 6

In plots measuring approximately 8 m², aubergines (growth stage 15) of the cultivar "Suqi qie" are treated in three replications against *Tetranychus urticae*. Application takes place using a back-mounted sprayer. In this example, a ready-prepared mixture (ratio 20:1) of the active ingredients Oberon, Example (I), and abamectin, Example (VI) as SC 240, is tested against the commercial standards abamectin (018 EC) and Oberon (240 SC) at the stated application rates. The water application rate is 450 l/ha.

Evaluation is made 1 day after treatment, by scoring the destruction of the males on the leaves.

| Active ingredient | Application rate g a.i./ha | Destruction (% Abbott) 1 day |
|---|---|---|
| Abamectin (VI) | 10 | 33.3 |
| Oberon (I) | 120 | 0 |
| Oberon (I) + Abamectin (VI) | 120 + 6 | 73.3* (33.3)** |

*activity found
**activity calculated by Colby formula

A further evaluation is made 21 days after treatment, by scoring the destruction of the eggs, the destruction of the males, and the total population on the leaves.

| Active ingredient | Application rate g a.i./ha | Destruction (% Abbott) 21 days (eggs) | 21 days (males) | 21 days (population) |
|---|---|---|---|---|
| Abamectin (VI) | 10 | 0 | 45 | 47.6 |
| Oberon (I) | 120 | 0 | 5 | 1.9 |
| Oberon (I) + Abamectin (VI) | 120 + 6 | 25* (0)** | 80.0* (47.8)** | 77.7* (40.5)** |

*activity found
**activity calculated by Colby formula

EXAMPLE 7

In plots measuring approximately 6 m², bell peppers of the cultivar "California Wonder" (growth stage 75) are treated in three replications against Hemitarsonemus latus. Application takes place using a sprayer at 2.5 bar pressure. In this example, a ready-prepared mixture (ratio 20:1) of the active ingredients Oberon, Example (I), and abamectin, Example (VI) as SC 240, is tested against the commercial standards abamectin (018 EC) and Oberon (240 SC) at the stated application rates and in the stated mixing ratios. The water application rate is 300 l/ha.

Evaluation is made 2 days after treatment, by scoring the destruction of the adults on the leaves.

| Active ingredient | Application rate g a.i./ha | Destruction (% Abbott) 2 days |
|---|---|---|
| Abamectin (VI) | 10 | 0 |
| Oberon (I) | 120 | 50 |
| Oberon (I) + Abamectin (VI) | 120 + 6 | 92.9* (50)** |

*activity found
**activity calculated by Colby formula

EXAMPLE 8

*Tetranychus urticae*—Test on Cotton

Solvent: 7 parts by weight of dimethylformamide
Emulsifier: 2 parts by weight of alkylaryl polyglycol ether An appropriate preparation of active ingredient is prepared by mixing 1 part by weight of active ingredient with the stated amounts of solvent and emulsifier and diluting the concentrate with emulsifier-containing water to the desired concentration.

Cotton plants (*Gossypium hirsutum*) infected with the two-spotted spider mite (*Tetranychus urticae*) are treated by being sprayed with the preparation of active ingredient in the desired concentration.

After the desired time, a determination is made of the destruction in %. 100% here means that all of the mites have been killed; 0% means that no mites have been killed. The destruction figures ascertained are calculated by the Colby formula.

In this test, the following active ingredient combination of the present specification exhibits a synergistically boosted activity in comparison to the compounds employed individually:

TABLE

*Tetranychus urticae* - test on cotton

| Active ingredient | Concentration g ai/ha | Destruction in % after $3^d$ | |
|---|---|---|---|
| Abamectin (VI) | 4 | 10 | |
| Spiromesifen (I) | 100 | 30 | |
| | | fnd.* | calc.** |
| Abamectin + Spiromesifen (1:25) inventive | 4 + 100 | 75 | 37 |

*fnd. = activity found
**calc. = activity calculated by the Colby formula

Thripse (Thripidae)

Additionally especially preferred is the control of the following species from the family of the Thripse (Thripidae) in the following crops:

| | |
|---|---|
| *Frankliniella occidentalis* | in vegetables such as, for example, bell peppers, tomatoes, cucumbers, brassicas, for example broccoli, beans lettuce, |
| *Frankliniella schultzei* | aubergines, courgettes, pumpkins, in soft fruit, for example |
| *Frankliniella furca* | strawberries, in melons, for example water melons, musk melons, cantaloupe melons, in ornamentals such as roses, hibiscus, chrysanthemums and also in potatoes and in tropical crops such as, for example, papayas, avocado, cotton, tobacco, conifers |
| *Thrips palmi* | in cotton, in vegetables such as, for example, bell peppers, tomatoes, cucumbers, beans, cucurbits, aubergines, courgettes, cabbage, leek, |
| *Thrips tabaci* | onions, spring onions, in soft fruit, in melons, for example water |
| *Thrips hawaiiensis* | melons, musk melons cantaloupe melons, in ornamentals such as for example, roses, hibiscus, in tropical crops such as, for example, papayas, pineapples, bananas, potatoes, grape vines, cotton, rice, nuts |
| *Heliothrips haemorrhoidalis* | in vegetables such as, for example, tomatoes, bell peppers, beans, cucumbers, pumpkins, aubergines, in melons and also in ornamentals such as, for example, roses, hibiscus, azaleas, tropical crops such as guava, citrus such as, for example, lemons, oranges, grape vines, nuts such as, for example, macadamia nuts |
| *Hercinothrips femoralis* | in tropical crops such as, for example, bananas, ornamentals, vegetables such as, for example, beans |
| *Hercinothrips bicinctus* | |
| *Hercinothrips phaseoli* | |
| *Caliothrips phaseoli* | in vegetables, such as, for example, beans, courgettes, in tropical fruits such as, for example, avocados |
| *Baliothrips biformis* | in rice |
| *Anaphothrips obscurus* | in maize, brassicas, such as, for example white cabbage, cereals such as, for example, wheat |
| *Scirthothrips aurantii* | in citrus such as, for example, oranges, lemons, grapefruits, tangerines, ornamentals, vegetables such as, for example, |
| *Scirthothrips dorsalis* | cucumbers, tomatoes, beans, aubergines, pumpkins; melons such as |
| *Scirthothrips citri* | water melons, cantaloupe melons, spices such as chili; tea |
| *Kakothrips pisivora* | in vegetables such as, for example, peas, beans |

EXAMPLE 9

In plots measuring approximately 10 m², bell peppers of the cultivar "Italiano verde" are treated in three replications against *Frankliniella occidentalis*. Application is made using a back-mounted spray (10 bar). The mixture of the active ingredients Oberon, Example (I), and abamectin, Example (VI), is tested against the commercial standards abamectin (018 EC) and Oberon (240 SC) at the stated application rates and in the stated mixing ratios. The water application rate is 750 l/ha. Two applications are carried out, at an interval of 7 days.

Evaluation is made 7 days after the second treatment, by scoring the destruction of the adults in the flowers.

| Active ingredient | Application rate g a.i./ha | Destruction (% Abbott) 7 days |
|---|---|---|
| Abamectin (VI) | 10.5 | 0 |
| Oberon (I) | 105 | 3.3 |
| Oberon (I) + Abamectin (VI) | 105 + 10.5 | 27.8* (3.3)** |

*activity found
**activity calculated by Colby formula

Evaluation is made 14 days after the second treatment, by scoring the destruction of the mixed population in the flowers.

| Active ingredient | Application rate g a.i./ha | Destruction (% Abbott) 14 days | Applicaton rate g a.i./ha | Destruction (% Abbott) 14 days |
|---|---|---|---|---|
| Abamectin (VI) | 21 | 2.0 | 10.5 | 0 |
| Oberon (I) | 210 | 0 | 105 | 0 |
| Oberon (I) + Abamectin (VI) | 210 + 21 | 26.1* (2.0)** | 105 + 10.5 | 16.7* (0)** |

*activity found
**activity calculated by Colby formula

White Fly (Aleyrodidae)

Further especially preferred is the control of the following species from the family of the white fly (Aleyrodidae) in the following crops:

*Bemisia tabaci* in vegetables such as bell peppers, tomatoes, cucumbers, brassicas, for example broccoli, beans, lettuce, aubergines, courgettes, pumpkins, in soft fruits, in melons, for example water melons, musk melons, cantaloupe melons, in ornamentals such as roses, hibiscus, in citrus such as oranges, tangerines, grapefruits, and also in potatoes, in tobacco, in soybeans, in cotton and in tropical crops, such as, for example, papayas, bananas,

*Bemisia argentifolii* in cotton, in vegetables such as bell peppers, tomatoes, cucumbers, beans, soybeans, cucurbits, aubergines, courgettes, cabbage, in soft fruits, in melons, for example water melons, musk melons, cantaloupe melons, in ornamentals such as, for example, roses, hibiscus, in tropical crops such as, for example, papayas, bananas, in soybean, in cotton

*Trialeurodes vaporariorum* in vegetables such as tomatoes, bell peppers, beans, cucumbers, pumpkins, aubergines, in soft fruits, in melons and also in ornamentals such as, for example, roses, hibiscus,

*Aleurothrixus floccosus* in citrus such as oranges, tangerines, lemons, dessert oranges

*Aleurodes citri* in citrus such as oranges, tangerines, lemons, grapefruits, limes, cumquats

*Aleurodes fragriae* in soft fruits, such as, for example, strawberries

*Aleurodes azaleae* in ornamentals, such as, for example, azaleas

EXAMPLE 10

*Bemisia tabaci*—Test on Cotton
Solvent: 7 parts by weight of dimethylformamide
Emulsifer: 2 parts by weight of alkylaryl polyglycol ether An appropriate preparation of active ingredient is prepared by mixing 1 part by weight of active ingredient with the stated amounts of solvent and emulsifier and diluting the concentrate with emulsifier-containing water to the desired concentration.

Cotton plants (*Gossypium hirsutum*) infested with whitefly (*Bemisia tabaci*) are treated by being sprayed with the preparation of active ingredient at the desired concentration.

After the desired time, the destruction is determined in %. 100% here means that all of the whitefly have been killed; 0% means that no whitefly have been killed. The destruction figures ascertained are calculated by the Colby formula.

In this test, the following active ingredient combination in accordance with the present specification exhibits a synergistically boosted activity in comparison to the compounds when applied individually:

TABLE

*Bemisia tabaci* - test on cotton

| Active ingredient | Concentration g ai/ha | Destruction in % after $7^d$ | |
|---|---|---|---|
| | | fnd.* | calc.** |
| Abamectin (VI) | 6 | 0 | |
| Spiromesifen (I) | 120 | 70 | |
| Abamectin & Spiromesifen (1:20) inventive | 6 + 120 | 90 | 70 |

*fnd. = activity found
**calc. = activity calculated by the Colby formula

EXAMPLE 11

*Bemisia tabaci*—Test on Cabbage
Solvent: 7 parts by weight of dimethylformamide
Emulsifer: 2 parts by weight of alkylaryl polyglycol ether An appropriate preparation of active ingredient is prepared by mixing 1 part by weight of active ingredient with the stated amounts of solvent and emulsifier and diluting the concentrate with emulsifier-containing water to the desired concentration.

Cabbage plants (*Brassica oleracea*) infested with whitefly (*Bemisia tabaci*) are treated by being sprayed with the preparation of active ingredient at the desired concentration.

After the desired time, the destruction is determined in %. 100% here means that all of the whitefly have been killed; 0% means that no whitefly have been killed. The destruction figures ascertained are calculated by the Colby formula.

In this test, the following active ingredient combination in accordance with the present specification exhibits a synergistically boosted activity in comparison to the compounds when applied individually:

TABLE

*Bemisia tabaci* - test on cabbage

| Active ingredient | Concentration g ai/ha | Destruction in % after $9^d$ | |
|---|---|---|---|
| | | fnd.* | calc.** |
| Abamectin (VI) | 15 | 0 | |
| | 6 | 0 | |
| Spiromesifen (I) | 150 | 55 | |
| Abamectin + Spiromesifen (1:10) (1:25) inventive | 15 + 150 | 85 | 55 |
| | 6 + 150 | 65 | 55 |

*fnd. = activity found
**calc. = activity calculated by the Colby formula

Leaf-Mining Flies (Agromyzidae)

Additionally especially preferred is the control of the following species from the family of the leaf-mining flies (Agromyzidae) in the following crops:

| | |
|---|---|
| *Liriomyza brassicae* | in vegetables such as bell peppers, tomatoes, cucumbers, cabbage, beans, lettuce, aubergines, courgettes, pumpkins, in melons, for |
| *Liriomyza bryoniae* | example water melons, musk melons, cantaloupe melons, in |
| *Liriomyza cepae* | ornamentals such as roses, hibiscus, and in potatoes, beet, |
| *Liriomyza chilensis* | |
| *Liriomyza hunidobrensis* | |
| *Liriomyza sativae* | |
| *Liriomyza trifolie* | |
| *Liriomyza quadrata* | |
| *Pegomya hyoscyami* | in beet, in vegetables and cereals, for example wheat |
| *Pegomya spinaciae* | |

Jumping Lice (Psyllidae)

Especially preferred is the control of the following species from the family of the jumping lice (Psyllidae):

| | |
|---|---|
| Psylla pyricola | in pome fruit such as, for example, pears, applies, in stone fruit such as, for example, cherries, plums, quetsch, peaches, nectarines |
| Psylla piri | in pome fruit such as, for example, pears |
| Psylla pyrisuga | in pome fruit such as, for example, pears |
| Psylla costalis | in pome fruit such as, for example, apples |
| Paratrioza cockerelli | in fruit vegetables such as, for example, tomatoes, bell peppers, chilies, in root vegetables such as, for example, carrots, in potatoes |
| Tenalaphara malayensis | in tropical crops such as, for example, durians (stink fruits), |
| Diaphorina citri | in citrus such as, for example, oranges, nectarines, lemons, grapefruits, |
| Trioza erythrae | in citrus such as, for example, oranges, grapefruits |

The good preservation of beneficial species and/or good insecticidal and/or acaricidal activity of the mixture/beneficial species combinations of the invention is evident from the examples below.

The activity which can be expected for a given combination of two active ingredients can be calculated by the method of S. R. Colby, Weeds 15 (1967), pages 20-22, as follows:

if

X is the degree of destruction expressed in % of the untreated control when active ingredient A is employed at an application rate of m g/ha or in a concentration of m ppm, Y is the degree of destruction expressed in % of the untreated control when active ingredient B is employed at an application rate of n g/ha or in a concentration of n ppm, and E is the degree of destruction expressed in % of the untreated control when the active ingredients A and B are employed at application rates of m and n g/ha or in a concentration of m and n ppm, then $$E = X + Y - \frac{X \cdot Y}{100}$$

If the actual degree of insecticidal or acaricidal destruction is less than calculated, then the combination is non-additive in its destruction—in other words, there is an antagonistic effect, and the population of beneficial species is preserved. In this case, the degree of destruction actually observed must be less than the figure for the expected degree of destruction (E) as calculated from the formula given above.

EXAMPLE 12

*Amblyseius swirskii*—Test on Plums

An appropriate solution for application is prepared by diluting the respective formulation to the desired concentration.

Plum leaves colonized by a mixed population of the predatory mite (*Amblyseius swirskii*) are treated by being sprayed with the application solution at the desired concentration.

After the desired time, a determination is made of the number of active stages, in %. 100% here means that all of the predatory mites have been killed; 0% means that no predatory mites have been killed. The destruction figures ascertained are calculated by the Colby formula.

In this test it is found that the active ingredient combination in various concentration ranges is more preserving of beneficial species in comparison to at least one compound when applied individually.

TABLE

*Amblyseius swirskii* - test on plums

| Active ingredient | Concentration g ai/ha | Destruction in % after 1$^d$ | | Destruction in % after 4$^d$ | |
|---|---|---|---|---|---|
| Abamectin (VI) EC 018 | 6 | 62 | | 68 | |
| Spiromesifen (I) SC 240 | 120 | 28 | | 32 | |
| | | fnd.* | calc.** | fnd.* | calc.** |
| Abamectin EC 018 + Spiromesifen SC 240 (1:20) inventive | 6 + 120 | 41 | 78.64 | 44 | 78.24 |
| Abamectin (VI) EC 018 | 3 | 38 | | 44 | |
| Spiromesifen (I) SC 240 | 60 | 17 | | 20 | |
| | | fnd.* | ber.** | fnd.* | calc.** |
| Abamectin EC 018 + Spiromesifen SC 240 (1:20) inventive | 3 + 60 | 21 | 48.54 | 24 | 55.2 |

*fnd. = activity found
**calc. = activity calculated by the Colby formula

EXAMPLE 13

*Coccinella septempunctata*/Larvae—Test on Plums

An appropriate solution for application is prepared by diluting the respective formulation to the desired concentration.

Plum leaves colonized by larvae of the seven-spotted ladybird (*Coccinella septempunctata*) are treated by being sprayed with the application solution at the desired concentration.

After the desired time, the destruction is determined in %. 100% here means that all of the ladybird larvae have been killed; 0% means that no ladybird larvae have been killed. The destruction figures ascertained are calculated by the Colby formula.

In this test it is found that the active ingredient combination in various concentration ranges is more preserving of beneficial species in comparison to at least one compound when applied individually.

TABLE

*Coccinella septempunctata* larvae - test on plums

| Active ingredient | Concentration g ai/ha | Destruction in % after 3$^d$ | |
|---|---|---|---|
| Abamectin (VI) EC 018 | 6 | 100 | |
| Spiromesifen (I) SC 240 | 120 | 10 | |
| | | fnd.* | calc.** |
| Abamectin EC 018 + Spiromesifen SC 240 (1:20) inventive | 6 + 120 | 73 | 100 |
| Abamectin (VI) EC 018 | 3 | 63 | |
| Spiromesifen (I) SC 240 | 60 | 3 | |
| | | fnd.* | calc.** |
| Abamectin EC 018 + Spiromesifen SC 240 (1:20) inventive | 3 + 60 | 33 | 64.11 |

*fnd. = activity found
**calc. = activity calculated by the Colby formula

The invention claimed is:

1. A composition comprising the compound of the formula (I)

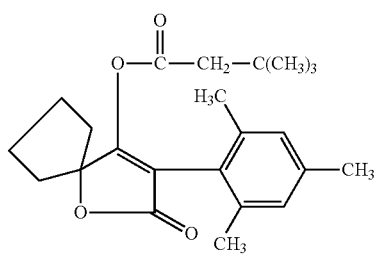

and abamectin, wherein the ratio the compound of formula (1) to abamectin is 20:1.

2. A method of controlling an insect or acarid comprising applying the composition according to claim 1 to said insect or acarid and/or a habitat thereof wherein said insect or acarid is from the order of the mites (Acari), from the family of the thrips, from the family of the Aleyrodidae, or from the family of the Psyllidae.

3. The method according to claim 2 wherein the insect or acarid is of the order of the mites (Acari).

4. The method according to claim 2 wherein the insect or acarid is of the family of the thrips.

5. The method according to claim 2 wherein the insect or acarid is of the family of the Aleyrodidae.

6. The method according to claim 2 wherein the insect or acarid is of the family of the Psyllidae.

7. The method according to claim 2 wherein the insect or acarid is of the family of the spider mites.

8. The method according to claim 2 wherein the insect or acarid is selected from the group consisting of Tetranychus urticae, Hemitarsonemus latus, Frankliniella occidentalis and Bemisia tabaci.

9. The method according to claim 2 wherein the habitat comprises vegetables.

10. The method according to claim 2 wherein the habitat comprises ornamental plants.

11. The method according to claim 2 wherein the habitat comprises cotton.

12. The method according to claim 2 wherein the habitat is selected from the group consisting of fruit, maize and soybeans.

13. The method according to claim 2 further comprising applying to the insect or acarid and/or the habitat a beneficial species selected from the group consisting of Araneae, Acari, Dermaptera, Hymenoptera, Coleoptera, Neuroptera, Tysanoptera, Heteroptera, Diptera, Hemiptera, Dermaptera and Parasitiformes.

14. The method according to claim 13 wherein the composition and beneficial species are applied successively.

15. A kit comprising the composition according to claim 1 and a beneficial species selected from the group consisting of Araneae, Acari, Dermaptera, Hymenoptera, Coleoptera, Neuroptera, Tysanoptera, Heteroptera, Diptera, Hemiptera, Dermaptera and Parasitiformes.

16. A method of controlling an insect or acarid comprising allowing the composition and the beneficial species of the kit according to claim 15 to act on said insect or acarid and/or a habitat thereof.

17. A method of reducing the number of per-season spray applications of the composition of claim 1 for control of an insect or acarid, comprising applying the composition and the beneficial species of the kit according to claim 15 to said insect or acarid and/or to a habitat thereof.

18. A method of reducing insecticide and/or acaricide residues of the composition of claim 1 on harvested produce comprising applying the composition and the beneficial species of the kit according to claim 15 to a plant or plant part on which the composition is utilized to control unwanted insects and/or acarids, whereby reduced insecticide and/or acaricide residues are on said harvested produce.

19. A method for improving production potential of a transgenic plant by controlling insects or acarids thereof and/or by improving said transgenic plant health and/or by improving abiotic stress resistance in said transgenic plant comprising applying the composition and the beneficial species of the kit according to claim 15 to said transgenic plant or a plant part thereof.

20. The method according to claim 19 wherein said transgenic plant is a soybean plant, cotton plant or maize plant.

* * * * *